A1

United States Patent
Aronowtiz et al.

(10) Patent No.: US 6,503,198 B1
(45) Date of Patent: Jan. 7, 2003

(54) NONINVASIVE TRANSDERMAL SYSTEMS FOR DETECTING AN ANALYTE OBTAINED FROM OR UNDERNEATH SKIN AND METHODS

(76) Inventors: Jack L. Aronowtiz, 6591 Skyline Dr., Del Ray Beach, FL (US) 33446; Joel R. Mitchen, 3040 Ocean Blvd., Fort Lauderdale, FL (US) 33308

( * ) Notice: Subject to any disclaimer, the term of this patent is extended or adjusted under 35 U.S.C. 154(b) by 0 days.

(21) Appl. No.: 08/929,262

(22) Filed: Sep. 11, 1997

(51) Int. Cl.[7] .................................................. A61B 5/00
(52) U.S. Cl. ........................ 600/365; 600/309; 600/367; 600/584
(58) Field of Search ................................ 600/309, 362, 600/364, 365, 367, 573, 584

(56) References Cited

U.S. PATENT DOCUMENTS

| | | | |
|---|---|---|---|
| 4,595,011 A | * 6/1986 | Phillips | 600/362 |
| 4,960,467 A | * 10/1990 | Peck | 600/362 |
| 5,462,064 A | * 10/1995 | D'Angelo et al. | 600/584 |
| 5,465,713 A | * 11/1995 | Schoendorfer | 600/362 |

* cited by examiner

Primary Examiner—Eric F. Winakur
(74) Attorney, Agent, or Firm—Saliwanchik, Lloyd & Saliwanchik

(57) ABSTRACT

The present invention relates to noninvasive transdermal systems and methods for analyte extraction from a biological fluid within or beneath the skin, such as interstitial fluid, and detection of the analyte. More particularly, the present invention relates to noninvasive transdermal patches comprised of a wet chemistry component and a dry chemistry component. The wet chemistry component is a liquid transfer medium in the form of a gel layer for the extraction and liquid bridge transfer of the analyte of interest from the biological fluid within or beneath the skin to the dry chemistry component. The dry chemistry component is a super sensitive or conditioned membrane carrying a reagent system for interacting with the analyte of interest to generate an indicator molecule, e.g., color change, to confirm detection of the analyte, and methods of use thereof. The indicator molecule may be visually observed by the individual user or observed by an electronic interpretation component, such as a reflectance spectrophotometer for detection. A particular analyte of interest which may be detected accurately, reliably and quantitatively in accordance with the present invention is glucose. The noninvasive transdermal systems of the present invention are low in-cost and suitable for convenient use by non-medical personnel.

54 Claims, 29 Drawing Sheets

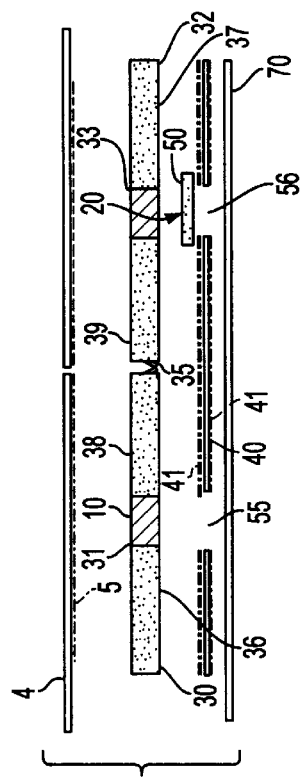
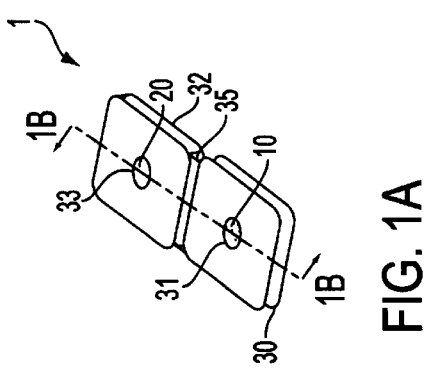
FIG. 1B
FIG. 1A
FIG. 1C

| [GLUCOSE] mg/dl | REFLECTANCE # |
|---|---|
| 0.0 | 2,025 |
| 12.5 | 1,932 |
| 25.0 | 2,387 |
| 50.0 | 2,508 |
| 100.0 | 2,770 |
| 200.0 | 2,928 |
| 300.0 | 3,137 |

AVG. OF NINE DETERMINATIONS FOR EACH SAMPLE
4%c.v
r=0.99

FIG. 15A

| TIME (MIN.) POSTPRANDIAL | BLOOD GLUCOSE STANDARD METHOD | NONINVASIVE GLUCOSE TEST KIT CALCULATED* | REFLECTANCE# NONINVASIVE TEST |
|---|---|---|---|
| 0 | 78 | 80 | 2,559 |
| 15 | 94 | 78 | 2,544 |
| 25 | 120 | 130 | 2,680 |
| 32 | 117 | 110 | 2,599 |
| 68 | 92 | 95 | 2,547 |
| 11 | 92 | 95 | 2,546 |
| 150 | 76 | 75 | 2,434 |
| 180 | 73 | 85 | 2,520 |

AVG. OF TWO DETERMINATIONS PER TIME POINT
MALE AGE 53 FASTED 12 HOURS
THEN DRANK 100 GRAMS D-GLUCOSE
*r=0.94

FIG. 15B

FIVE MINUTES SKIN CONTACT TIME

FIVE MINUTES SKIN CONTACT TIME

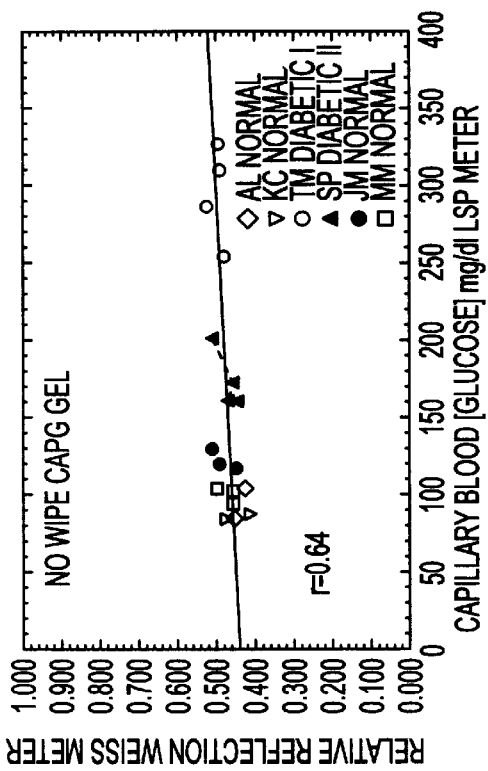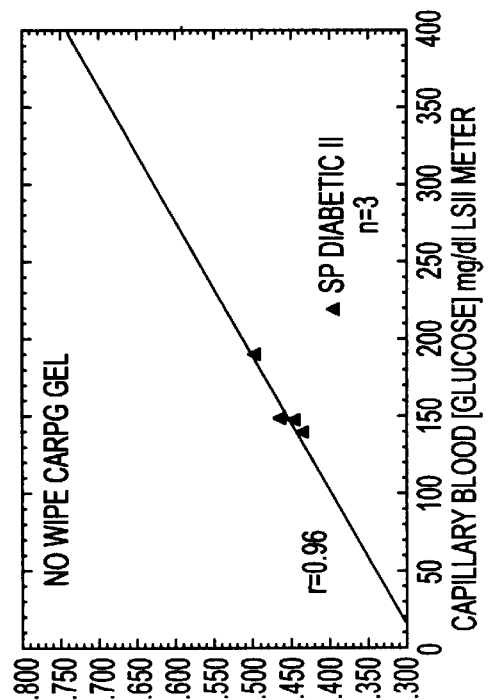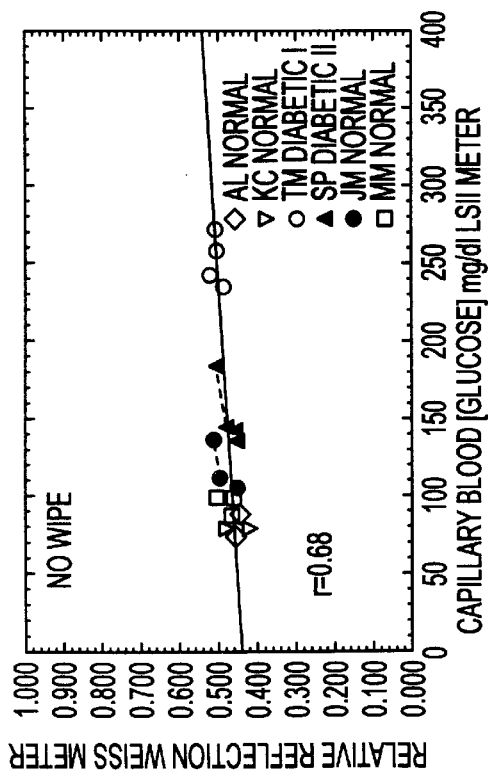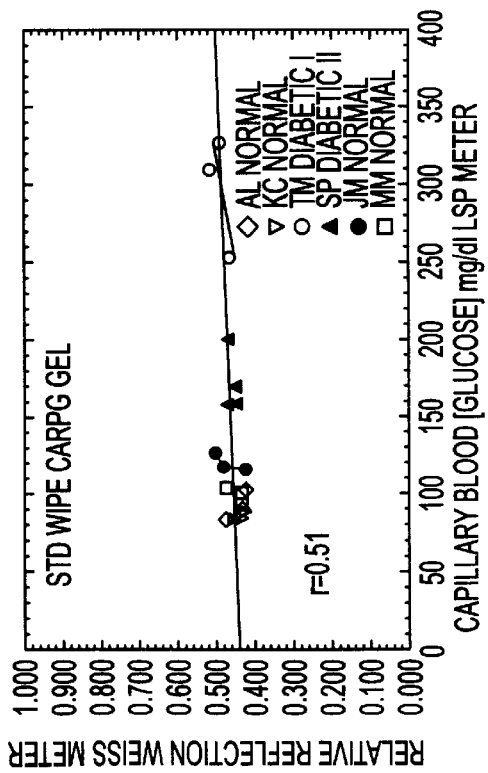

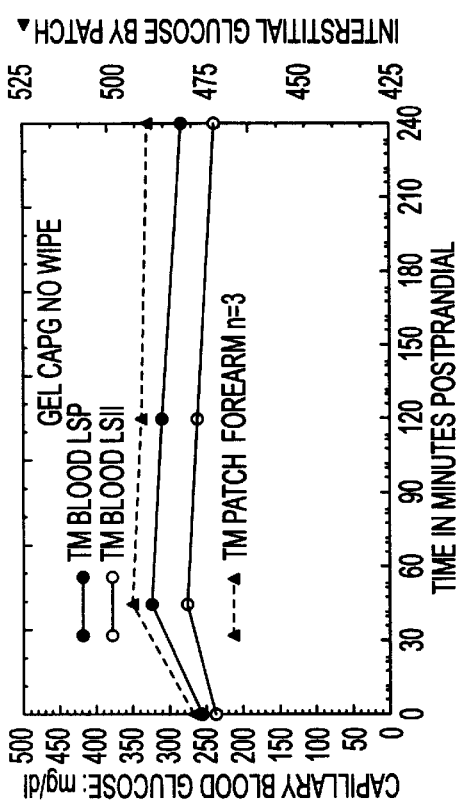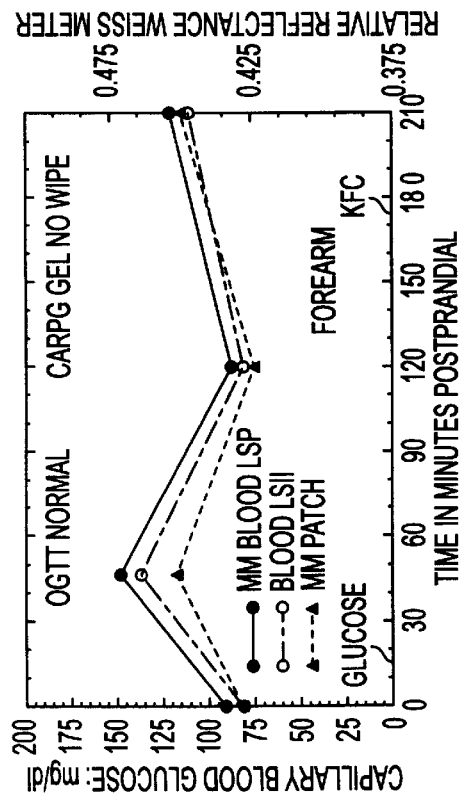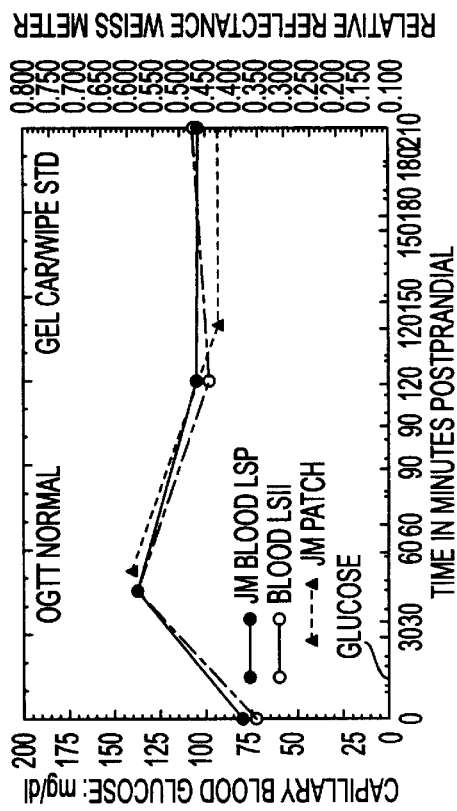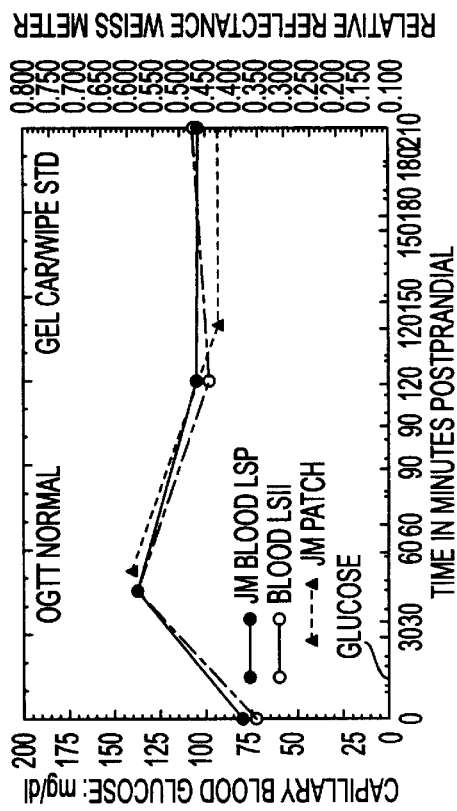

NONINVASIVE TRANSDERMAL SYSTEMS FOR DETECTING AN ANALYTE OBTAINED FROM OR UNDERNEATH SKIN AND METHODS

FIELD OF THE INVENTION

The present invention concerns noninvasive transdermal systems and methods for analyte extraction from a biological fluid within or beneath the skin, such as interstitial fluid, and detection of the analyte. More particularly, the present invention relates to noninvasive transdermal patches comprised of a wet chemistry component for extraction of the analyte of interest from a biological fluid within or beneath the skin and presentation to a dry chemistry component which interacts with the analyte for indicator molecule formation to confirm detection of the analyte, and methods of use thereof.

BACKGROUND

The determination of an individual's physiological status is frequently assisted by chemical analysis for the existence and/or concentration level of an analyte in a body fluid. This practice is common in the diagnosis of diabetes and in the management of this disease. Blood sugar levels can generally fluctuate with the time of day and with the period since the individual's last consumption of food. Management of diabetes often, thus, requires the frequent sampling and analysis of the diabetic's blood for determination of its relative glucose level. The management of this disease by the diabetic will typically involve the sampling of his/her own blood, the self-analysis of the sample for its relative glucose content and the administration of insulin, or the ingestion of sugar, depending upon the indicated glucose level.

To determine blood glucose concentrations, blood is presently drawn several times per day by the diabetic. Unfortunately, the current methods of monitoring blood glucose levels has many drawbacks. The current methods generally rely upon finger lancing to monitor blood glucose levels, which is not easy for anyone, especially young children and the elderly. Moreover, because blood is involved, there is always the risk of infection and of transmission of blood borne diseases, such as AIDS. Still further, special procedures and systems for handling and disposing of the blood are required. If the blood glucose concentrations in such individuals are not properly maintained, the individuals become susceptible to numerous physiological problems, such as blindness, circulatory disorders, coronary artery disease, and renal failure. For these reasons, there is a great unmet need for a noninvasive method for monitoring blood glucose levels. A substantial improvement in the quality of life of persons suffering from various maladies, such as diabetes mellitus, could be attained if the concentrations of species in body fluids are noninvasively determined.

There are a number of devices on the market to assist the diabetic in the self-testing of the blood sugar level. One such device, developed by Audiobionics (now Garid, Inc.) and described in U.S. Pat. No. 4,627,445, issued Dec. 9, 1986, involves the use of a fixture containing a multi-layered element for the collection of the whole blood sample, the transport of the sample from the point of application on the element to a porous membrane, and the analysis of the blood sample for its glucose contents by a dry chemistry reagent system which is present within the porous membrane.

Other such devices described in U.S. Pat. Nos. 5,462,064 and 5,443,080 and issued to J. P. D'Angelo et al. involve the use of a multi-part system to collect and analyze constituents of body fluid. In D'Angelo et al., the systems rely upon, among other things, a multilayered gel matrix which includes a separate activation gel layer and a separate collection gel layer disposed below the activation gel layer, an osmotic flow enhancer, such as ethyl ether, to facilitate the collection of an analyte fluid, and a chemistry detection methodology to aid in the visual or electronic determination of an analyte under investigation. Ethyl ether, however, is a known skin irritant which is flammable and explosive.

Another such device described in U.S. Pat. No. 5,203,327 and issued to D. W. Schoendorfer et al., involves a method and apparatus for the non-invasive determination of one or more preselected analytes in perspiration. In D. W. Schoendorfer, et al., the fluid is collected in a dermal concentration patch and concentrated by driving off a portion of the substantial water fraction under the influence of body heat, and the analyte is optimally complexed with an immobilized specific binding partner and an indicium of the presence of the analyte is usually experienced.

Other such devices are described in U.S. Pat. Nos. 4,960,467; 4,909,256; 4,821,733; 4,819,645; and 4,706,676 and issued to Peck. According to these patents, the Peck devices involve a dermal substance collection device (DSCD) which provides for the non-invasive, instantaneous and continuous monitoring of chemical substances which are present in detectable amounts in either or both interstitial fluid or sweat or which are on or in the skin. More particularly, the Peck transdermal substance collection devices are comprised of three essential components: (1) a substance binding reservoir, wettable by (2) a liquid transfer medium which allows for liquid bridge transfer of a soluble substance from the skin surface to the biding reservoir by virtue of its wettability by the liquid, and (3) an occlusive cover.

Exemplary of other systems have been previously proposed to monitor glucose in blood, as is necessary, for example, to control diabetic patients. This is represented, for example, by Kaiser, U.S. Pat. No. 4,169,676, Muller, U.S. Pat. No. 4,427,889, and Dahne et al., European Patent Publication No. 0 160 768, and Bauer et al., *Analytica Chimica Acta* 197 (1987) pp. 295–301.

In Kaiser, glucose in blood is determined by irradiating a sample of the blood with a carbon dioxide laser source emitting a coherent beam, at a single frequency, in the mid-infrared region. An infrared beam derived from the laser source is coupled to the sample by way of an attenuated total reflectance crystal for the purpose of contacting the blood sample. The apparatus uses double beam instrumentation to examine the difference in absorption at the single frequency in the presence and absence of a sample.

Muller discloses a system for quantifying glucose in blood by irradiating a sample of the blood with energy in a single beam from a laser operating at two frequencies in the mid-infrared region. The infrared radiation is either transmitted directly to the sample or by way of an attenuated total reflectance crystal for in vitro sampling. One frequency that irradiates the sample is in the 10.53–10.6 micrometer range, while the other irradiating frequency is in the 9.13–9.17 micrometer range. The radiation at the first frequency establishes a baseline absorption by the sample, while glucose absorption by the sample is determined from the intensity reduction caused by the sample at the second wavelength. The absorption ratio by the sample at the first and second frequencies quantifies the glucose of the sample.

Dahne et al. employ near-infrared spectroscopy for noninvasively transmitting optical energy in the near infrared spectrum through a finger or earlobe of a subject. Also discussed is the use of near-infrared energy diffusely reflected from deep within the tissue. Responses are derived at two different wavelengths to quantify glucose in the subject. One of the wavelengths is used to determine background absorption, while the other wavelength is used to determine glucose absorption. The ratio of the derived intensity at the two different wavelengths determines the quantity of glucose in the analyte biological fluid sample.

Bauer et al. disclose monitoring glucose through the use of Fourier-transform infrared spectrometry wherein several absorbance versus wavelength curves are illustrated. A glucose concentration versus absorbance calibration curve, is constructed from several samples having known concentrations, in response to the intensity of the infrared energy absorbed by the samples at one wavelength, indicated as preferably 1035 $cm^{-1}$.

Notwithstanding the above, the most frequently employed systems for determining the concentration of molecular substances in biological fluids have used enzymatic, chemical and/or immunological methods. However, these techniques generally require invasive methods to draw a blood sample from a subject; typically, blood must be drawn several times a day by a finger prick, such as presently employed by a diabetic and externally determining the glucose level, generally by chemical reaction followed by colorimetric comparative testing. For example, in the determination of glucose by diabetics, such invasive techniques must be performed using present technology.

Because the prior art invasive techniques are painful, individuals frequently avoid having blood glucose measured. For diabetics, the failure to measure blood glucose on a prescribed basis can be very dangerous. Also, the invasive techniques, which rely upon lancing blood vessels, create an enhanced risk for disease transmission and infection.

Thus, there remains a need in many diverse applications for a system for the noninvasive, painless determination of a preselected analyte in a body fluid, such as interstitial fluid, which can be utilized to detect the presence of the preselected analyte. Clearly, in the case of diabetics, it would be highly desirable to provide a less invasive system for analyzing glucose concentrations in the control of diabetes mellitus. The system should be low-cost and suitable for convenient use by non-medical personnel.

SUMMARY OF THE INVENTION

In brief, the present invention overcomes certain of the above-mentioned drawbacks and shortcomings through the discovery of a novel transdermal system for detecting an analyte of interest in a biological fluid and methods concerning same, without resort to prior standard invasive, painful techniques. In accordance with the present invention, the novel noninvasive transdermal systems provide for sample collection and detection in the form of a simple, easy-to-use, integrated system which is low-cost and suitable for convenient use by non-medical personnel. Moreover, because the novel transdermal systems of the present invention are noninvasive and painless, as compared to the invasive techniques generally utilized heretofore, e.g, a finger prick or finger lance, individual compliance should be enhanced, and the risk of disease transmission and infection should be reduced.

With the foregoing in mind and other objects in view, there is provided, in accordance with the present invention, a noninvasive transdermal system for collecting and detecting an analyte of interest in a biological fluid within or underneath the skin. Generally speaking, the noninvasive transdermal systems of this invention are comprised of two essential components (1) a dry chemistry component; and (2) a wet chemistry component. The dry chemistry component comprises a super sensitive or conditioned membrane containing a compliment of chemical reagents which are specific for reacting with one or more analytes of interest. The interaction of the analyte(s) and such chemical reagents is manifest by the release or formation of indicator molecules, e.g., color change, which is indicative of the presence of the analyte(s) in the biological fluid. The surface of the super sensitive or conditioned membrane, which is receptive of and exposed to the analyte of interest, is relatively dense, thereby being generally free of cells, particles and/or other micromolecules which can potentially interfere with reaction of the analyte and the chemical reagents and/or the detection of a reporter molecule. In contrast, the opposing surface of the super sensitive or conditioned membrane is substantially less dense (more porous), thereby allowing for infusion of the reagent system during manufacture, and the formation, diffusion and visualization of reporter or indicator molecules, which are indicative of the presence of the analyte of interest and its level of concentration in the body fluid. The super sensitive or conditioned membrane of the present invention have the unique ability to detect analytes in very small sample volumes, e.g., about 25 mcl, in very small concentrations which are at least as low as about 20 mcg/dl or 1 mcg/5 ml or 0.005 mcg/25 mcl.

The wet chemistry component of the present invention comprises a generally liquid transfer medium which allows for liquid bridge transfer or extraction of an analyte of interest from the biological fluid within or underneath the skin to the super sensitive or conditioned membrane for reaction with the reagents to release or form the reporter or indicator molecule, which is indicative of the presence of the analyte in the biological fluid.

More specifically, and in accordance with the present invention, the compliment of reagents, with which the membrane is conditioned, includes a chemical reactant and a color developer specifically provided for an analyte of interest. Also in accordance with the present invention, the liquid transfer medium is in the form of a gel layer or gel matrix which permits for liquid transfer or extraction of the soluble analyte under investigation from the biological fluid within or underneath the skin to the site of reaction at the super sensitive or conditioned membrane. Preferably, the gel layer is a hydrophobic gel which is inert, nonflammable and nonirritating to the skin. An especially preferred hydrophobic gel in accordance with the present invention is a gel formulated with carboxy polymethylene, marketed or sold under the brand name Carbopol®, and deionized water (18 meg ohm) in a concentration of from about 0.5% to about 2.0%, and preferably in a concentration of about 1%.

In accordance with a further feature of the present invention, the gel includes a permeation skin enhancer selected for the analyte to be detected for enhancing the liquid bridge transfer or extraction of the analyte from the biological fluid within or underneath the skin to the super sensitive or conditioned membrane for reaction and detection. Preferred skin permeation enhancers contemplated by the present invention are those which are nonflammable, nonexplosive and nonirritating to the skin, and which do not interfere with the analyte under investigation, its transfer to the super sensitive or conditioned membrane and its interaction with the chemical reagents. In accordance with the present invention, a preferred skin permeation enhancer is propylene glycol elegantly admixed in the gel in a concentration of from about 5% to about 20%, and especially admixed in the gel in a concentration of about 10%. Thus, an especially preferred gel in accordance with the present invention comprises about 1% carboxy polymethylene, e.g., Carbopol®, and about 10% propylene glycol in deionized water (18 meg ohm).

Alternatively, and also in accordance with the present invention, a skin permeation enhancer may be first directly applied to the targeted skin area to which the transfer medium or gel is applied. While the present invention contemplates the use of a permeation enhancer separate from or in addition to the transfer medium gel, it has been surprisingly discovered that, when a skin permeation enhancer is incorporated into the transfer medium or gel, it is not necessary to apply a skin permeation enhancer directly to the skin before applying the novel noninvasive transdermal systems of the present invention.

Also in accordance with the present invention, the novel noninvasive transdermal systems can be configured as a component of a noninvasive transdermal patch for collection and detection of an analyte in a biological fluid within or underneath the skin. When configured into a noninvasive transdermal patch, it is contemplated that the dry chemistry component and the wet chemistry component are maintained separately prior to use and that, upon use, the super conditioned membrane and the transfer medium shall be the exclusive means of access of the analyte under investigation to the chemical reagents infused onto and/or within the membrane.

In a preferred embodiment in accordance with the present invention, the body fluid from which an analyte may be transdermally extracted is interstitial fluid.

In yet a further feature of the present invention, an electronic interpretation component may be utilized for detecting the reporter or indicator molecules, e.g., color change, generated from the presence of the analyte. in the biological fluid and its reaction with the chemical reagents. The electronic interpretation components should include a light source for illuminating the indicator molecule, a photosensor sensing a reflecting intensity from the indicator molecules and a system for interpreting the measured reflectance intensity and providing information regarding a result of the interpretations.

It should nevertheless be understood that, while any commercial reflectometer capable of reading a color change in a wavelength range of, for example, about 500 nm to about 930 nm at an angle of reflection in the range of about 30° to about 90° with a voltage of from about 200 to about 1 with a sensitivity of about ±0.1 mV, may be used in accordance with the novel noninvasive transdermal systems of the present invention, the reading head of such reflectometers should preferably be configured so as to interface precisely with the recess or through aperture leading to the dry chemistry component of the novel noninvasive transdermal systems. Preferably, the reading head of a reflectometer should have a matching sensor and LED which can read reflectance from color in a wavelength range of from about 650 nm to about 670 nm at an angle of reflectance in the range of about 35° to about 45° with such sensitivity. FIG. 9 depicts an exemplary reflectometer in accordance with the present invention having a reading head which is configured for precise interface with a recess or through aperture that leads to the dry chemistry component or membrane. The reflectometer depicted in FIG. 9 further includes a visual display for communicating the results detected by the reflectometer. FIG. 10 illustrates a cross section of a reflectometer depicted in FIG. 9 for interfacing with a transdermal patch of the present invention at a 40° angle of reflectance for reading color intensity for analyte detection.

With the above-listed objects in view, there is provided, in accordance with the present invention, a collection and indication apparatus for biological fluid constituent analysis, which comprises a collector component for noninvasively and transdermally collecting a body fluid analyte from an individual or subject in the form of a dry chemistry component including a compliment of chemical reagents for reacting with the analyte for indicating its presence and a wet chemistry component for extracting and transferring the analyte from the body fluid within or underneath the skin to the chemical reagents; and a configuration specifically designed for keeping the dry chemistry component and the wet chemistry component intact and separate from one another during non-use, but which allows them to intimately engage one another during testing, so that the dry chemistry component is continuously an d uniformly wetted during testing by the wet chemistry component and the analyte under investigation can be extracted and transferred from the biological fluid within or underneath the skin to the super sensitive or concentrated membrane for interaction with the chemical reagents to generate the reporter or indicator molecules, e.g., color change, to confirm analyte presence. Preferably, the body fluid is interstitial fluid from which the analyte is transdermally and noninvasively extracted and collected.

In other words, the novel noninvasive, transdermal systems of the present invention include three major operational components. The first is the wet chemistry component which functions as the liquid bridge for transferring the analyte of interest from the biological fluid within or underneath the skin to the dry chemistry component, the second component is the dry chemistry component infused with a chemical reaction system specifically for interacting with the analyte of interest to detect its presence, and the third component is a support or housing for the systems which are configured to ensure that the wet and dry chemistry components remain separate during nonuse, but are in direct and continuous contact when the systems are in use and which enables the individual users to physically hold the systems and review the generated data in a rapid and meaningful way. In addition, the novel noninvasive transdermal systems of the present invention contemplate the use of a permeation skin enhancer admixed into the wet chemistry component and/or at the targeted skin areas prior to application of the novel noninvasive transdermal systems to such skin areas. Still further, the novel noninvasive transdermal systems of the present invention contemplate an electronic interpretation component especially configured for precise interfacing with the dry chemistry component, so that the reading head can read changes in color intensity in a preferred wavelength range of about 650 nm +10 nm at an angle of reflectance of about 40° with a sensitivity precision of about ±0.1 mV. In other words, the electronic interpretation component of the system is configured so as to read the patch component in the event of a visual impairment, or if a more precise numerical value is required, it will give a report in that format.

A novel method of combining test chemistries known to those in the healing arts with the interstitial fluid collection medium in such a manner as to cause to be noninvasively and transdermally extracted from or through the skin, a quantity of analyte of interest sufficient for the chemical test to proceed and then to have the ability to read and record the results in a very short period of time, e.g., a few minutes, is described. This is one of the major objects of this invention.

In a preferred embodiment, the present invention contemplates small disposable transdermal patches for use with a reflectometer to detect an analyte such as glucose. In accordance with the present invention, the small disposable transdermal patches measure blood glucose levels noninvasively. In actuality, the small disposable transdermal patches of the present invention have the unique ability to detect the levels of glucose in interstitial fluid which directly correlate to those levels in the blood. Briefly, and not to be limited, the process is believed to occur as follows. A small disposable transdermal patch of the present invention, which is strategically placed on the targeted skin area, painlessly draws glucose from the interstitial fluid through the skin. The glucose is transported by the skin permeation enhancer combined with a gel capable of transporting glucose through the stratum corneum (upper level of the epidermis). The glucose in the interstitial fluid then undergoes a glucose-specific biochemical reaction at the site of the dry chemistry membrane, the biochemical reaction of which are contained within the dry chemistry membrane in the patch. This biochemical reaction results in a color formation which is then measured by a reflectometer and directly correlated to the blood glucose levels. It is believed that the membrane based technology of the present invention is at least 100, if not 400–500, times more sensitive for detection of very small concentrations of an analyte, e.g., about 20 mcg/dl or 1 mcg/5 ml or 0.005 mcg/25 mcl in a very small volume of fluid, e.g., about 25 mcl, than what is being currently used with finger stick or finger lancing technology. Thus, and in accordance with the present invention, the extraction and detection process only requires a small patch and a small hand held reflectometer. And, because blood is not at all involved, pain and the risk of infection and disease transmission generally associated with glucose monitoring have been eliminated. Moreover, special handling procedures or disposable systems are no longer required.

The noninvasive transdermal systems of the present invention analyze analytes in interstitial fluid rather than blood. Interstitial fluid is the nutrient fluid between the cells within the body tissues. The volume of interstitial fluid in the body is more than three time the blood volumes, and the concentrations of various constituents of the interstitial fluid are generally in equilibrium with the concentrations of those same constituents in blood. In accordance with the present invention, it is believed that small quantities of analyte in the interstitial fluid diffuse into the novel noninvasive transdermal systems with the aid of the gel in combination with a skin permeation enhancer. Once inside the systems of the present invention, the analyte from the interstitial fluid undergoes an enzymatic reaction which leads to the formation of colored indicator material. The color produced is believed to be proportional to the concentration of the analyte in the interstitial fluid, which in turn is proportional to the analyte concentration in the blood. This color is measured by surface reflectance via a fixed-wavelength optical meter, and is then compared to onboard calibration values. The result is typically displayed in units of mg/dl.

An integral component of the invention is the transdermal patch which allows the system to work as a non-invasive skin test for clinical analytes. Additionally, what is shown and described are various configurations, all of which work together as a new and novel system to evaluate chemical analytes from noninvasively and transdermally extracted biological fluids.

Other features which are considered as characteristic for the invention are set forth in the appended claims.

Although the present invention is illustrated and described herein as embodied in an integrated noninvasive and transdermal system for biological fluid constituent analysis, it is nevertheless not intended to be limited to the details shown, since various modifications and structural changes may be made therein without departing from the spirit of the invention and within the scope and range of equivalents of the claims.

The construction of the invention, however, together with additional objects and advantages thereof will be best understood from the following description of specific embodiments when read in connection with the accompanying FIGS. and examples.

The above features and advantages of the present invention will be better understood with reference to the following detailed description and examples. It should also be understood that the particular methods and formulations illustrating the present invention are exemplary only and not to be regarded as limitations of the present invention.

BRIEF DESCRIPTION OF THE FIGS.

Reference is now made to the accompanying Figs. in which are shown characteristics corresponding to the present invention from which certain of its novel features and advantages will be apparent:

FIG. 1A is a perspective view of a noninvasive transdermal patch according to one embodiment of the present invention.

FIG. 1B is a cross-sectional view along the line 1A—1A of the noninvasive transdermal patch of FIG. 1A.

FIG. 1C is a perspective of a noninvasive transdermal patch illustrated in FIG. 1A but in a closed position.

FIG. 15A is a table depicting the data of the calibration curve of FIG. 14.

FIG. 15B is a table of data corresponding to FIG. 11.

Figure 26:
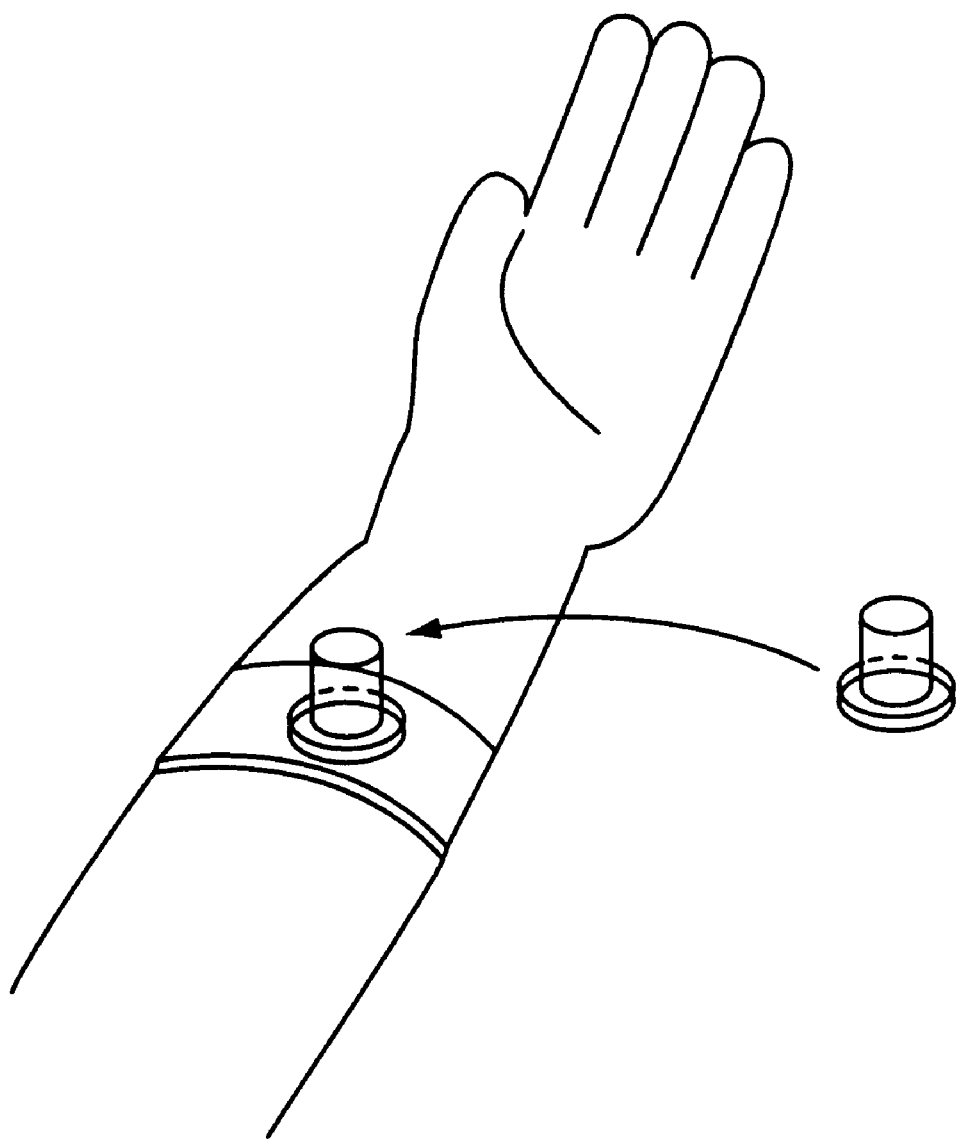
Figure 28B:
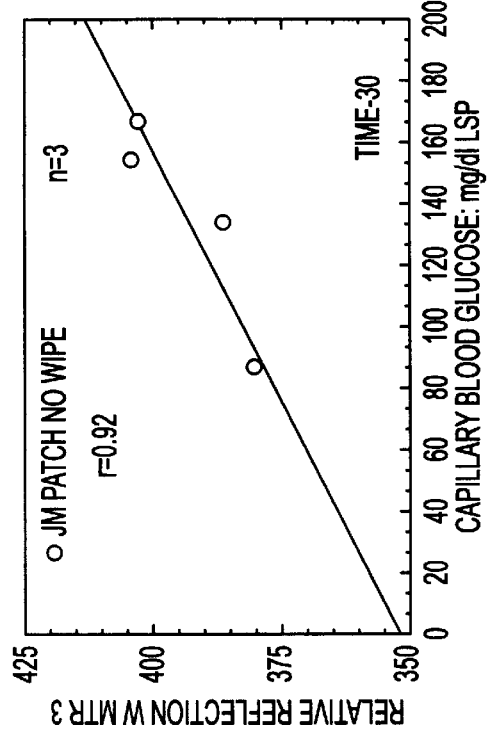
Figure 28D:
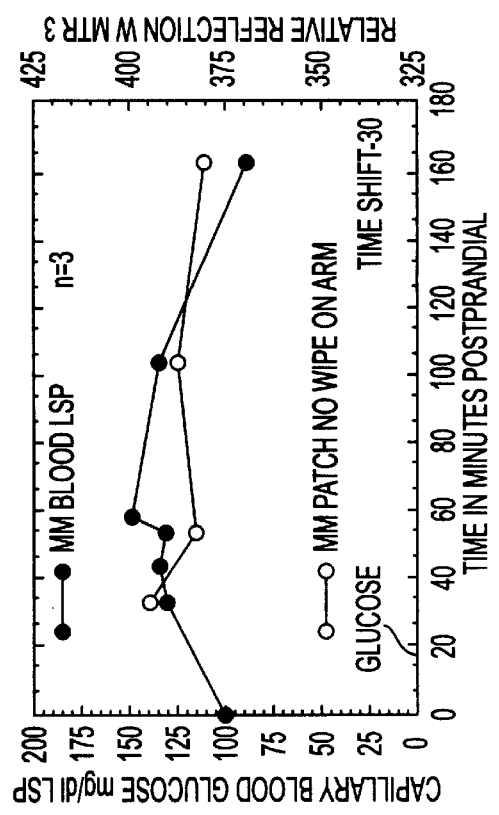
Figure 28A:
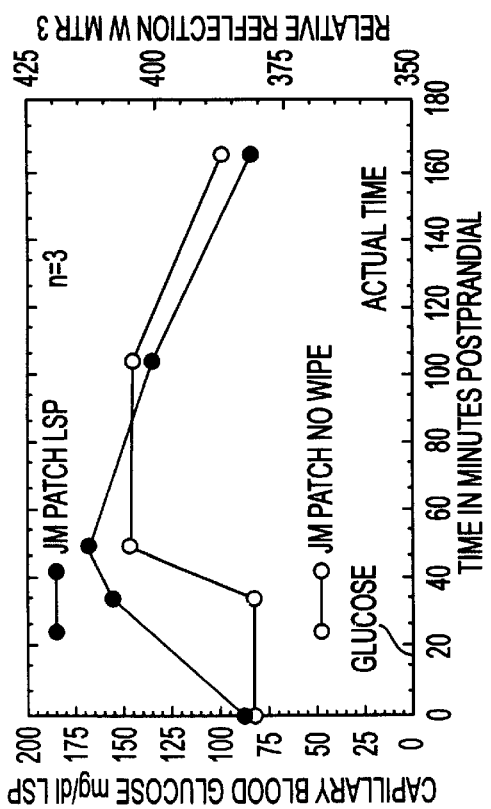
Figure 28C:
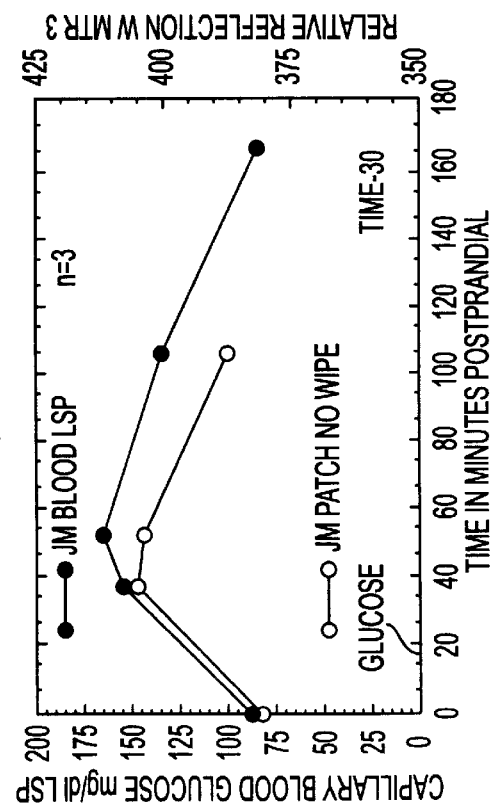

FIG. 26 describes generally a method of testing the permeation enhancing power of the skin permeation enhancer in accordance with the present invention.

FIG. 27 is a plot of data which compares the results obtained from a noninvasive transdermal patch of the present invention with results obtained from capillary blood glucose utilizing standard LSII methods.

FIG. 28 is a plot of data which compares the results obtained from a noninvasive transdermal patch of the present invention with results obtained from capillary blood glucose utilizing standard LSII methods.

Figure 29:
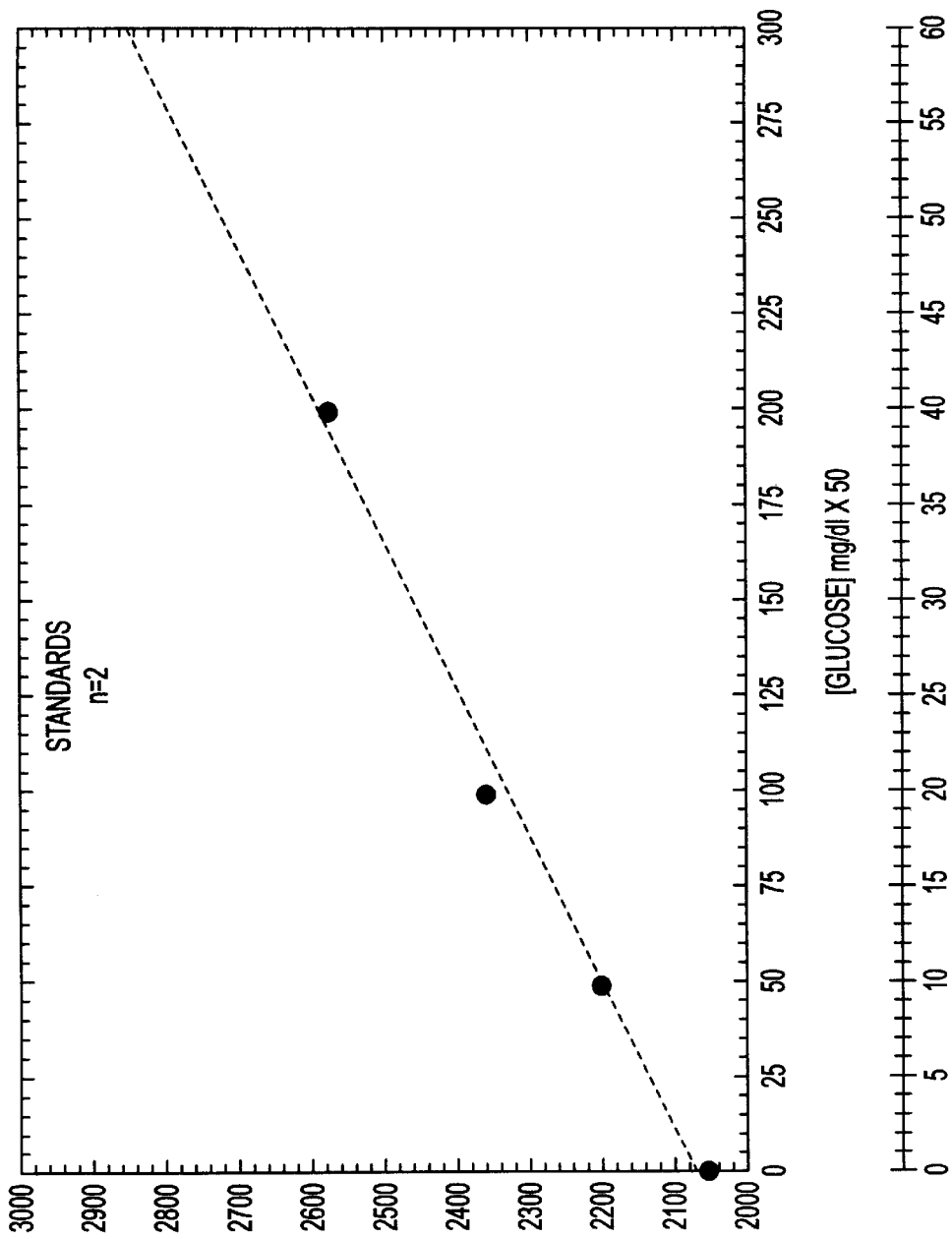

FIG. 29 is a plot of data showing the sensitivity of a noninvasive transdermal glucose patch of the present invention.

Figure 30:
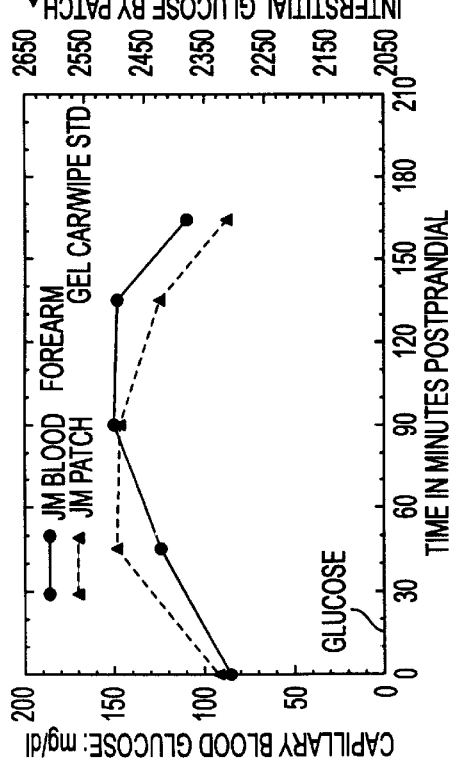

FIG. 30 is a plot of data comparing results obtained from a noninvasive transdermal patch of the present invention with results obtained from blood glucose by standard method.

Figure 31:
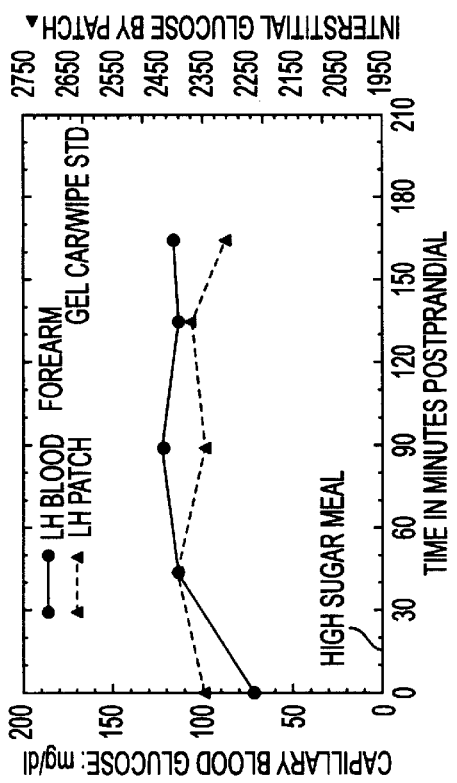

FIG. 31 is a plot of data comparing results obtained from a noninvasive transdermal patch of the present invention with results obtained from blood glucose by standard method.

Figure 32:
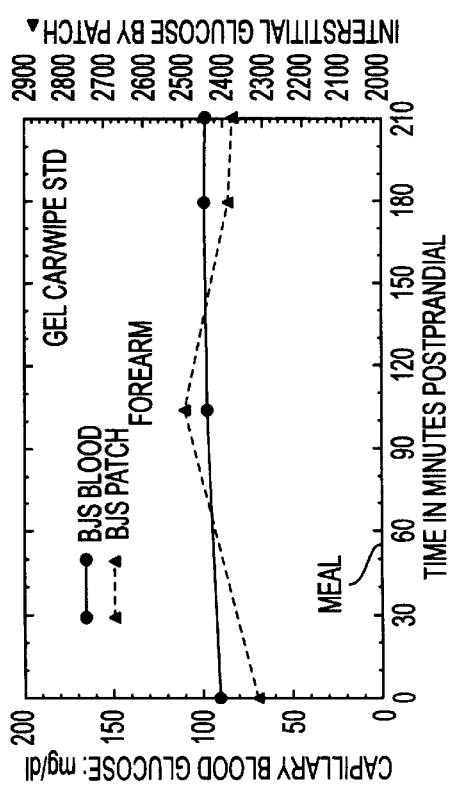

FIG. 32 is a plot of data comparing results obtained from a noninvasive transdermal patch of the present invention with results obtained from blood glucose by standard method.

Figure 33:
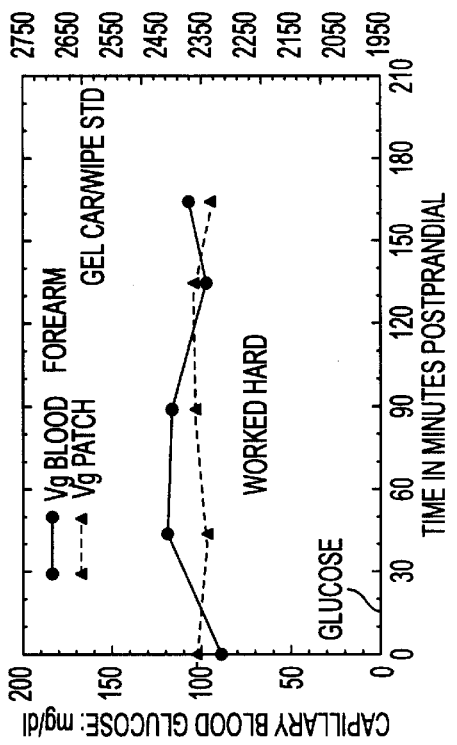

FIG. 33 is a plot of data comparing results obtained from a noninvasive transdermal patch of the present invention with results obtained from blood glucose by standard method.

FIG. 34 is a plot of data which compares the results obtained from a noninvasive transdermal patch of the present invention with results obtained from capillary blood glucose utilizing standard method.

FIG. 35 is a plot of data which compares the results obtained from a noninvasive transdermal patch of the present invention with results obtained from capillary blood glucose utilizing standard method.

FIG. 36 is a plot of data which compares the results obtained from a noninvasive transdermal patch of the present invention with results obtained from capillary blood glucose utilizing standard method.

FIG. 37 is a plot of data which compares the results obtained from a noninvasive transdermal patch of the present invention with results obtained from capillary blood glucose utilizing standard method.

Figure 38:
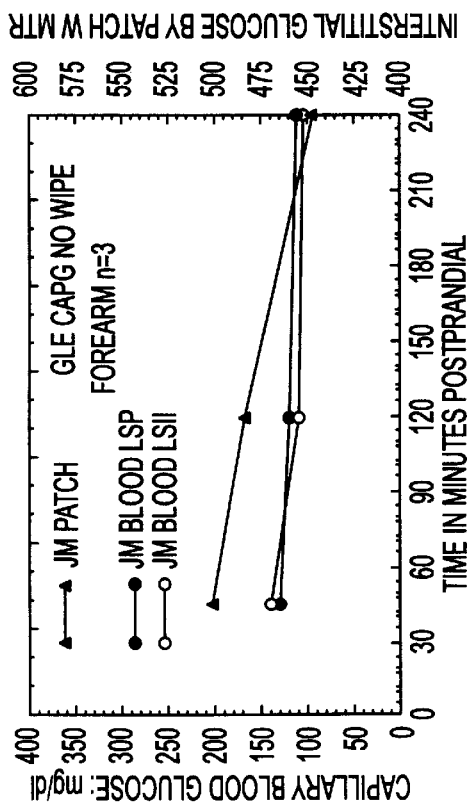

FIG. 38 is a plot of data which compares the results obtained from a noninvasive transdermal patch of the present invention with results obtained from capillary blood glucose utilizing standard method.

Figure 39:
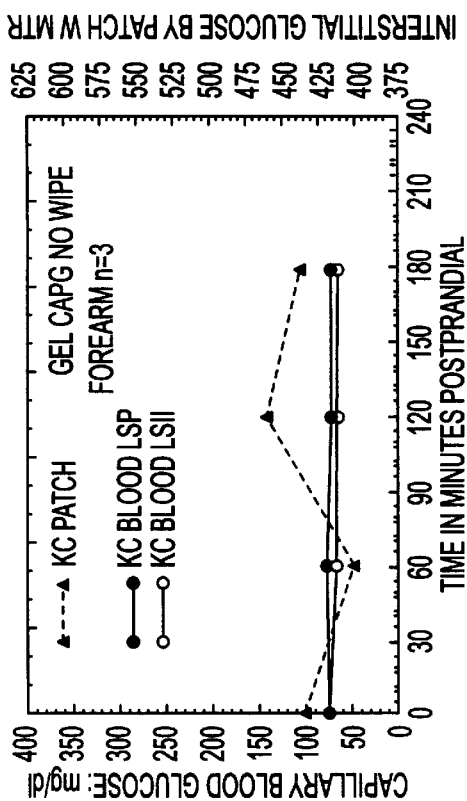

FIG. 39 is a plot of data which compares the results obtained from a noninvasive transdermal patch of the present invention with results obtained from capillary blood glucose utilizing standard method.

Figure 40:
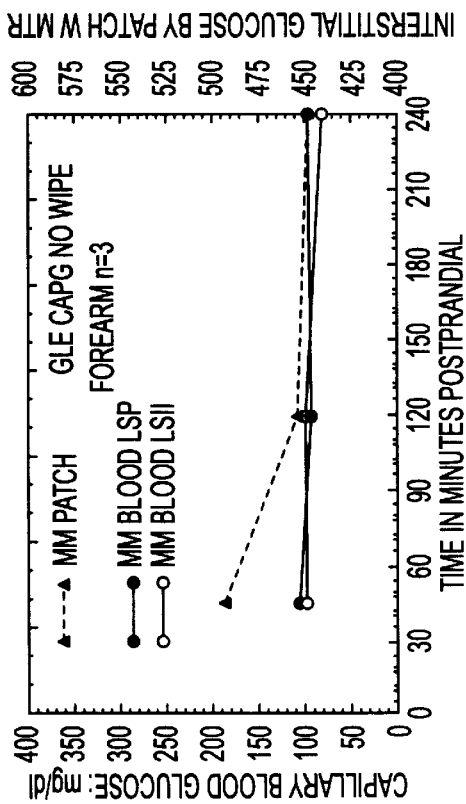

FIG. 40 is a plot of data which compares the results obtained from a noninvasive transdermal patch of the present invention with results obtained from capillary blood glucose utilizing standard method.

Figure 41:
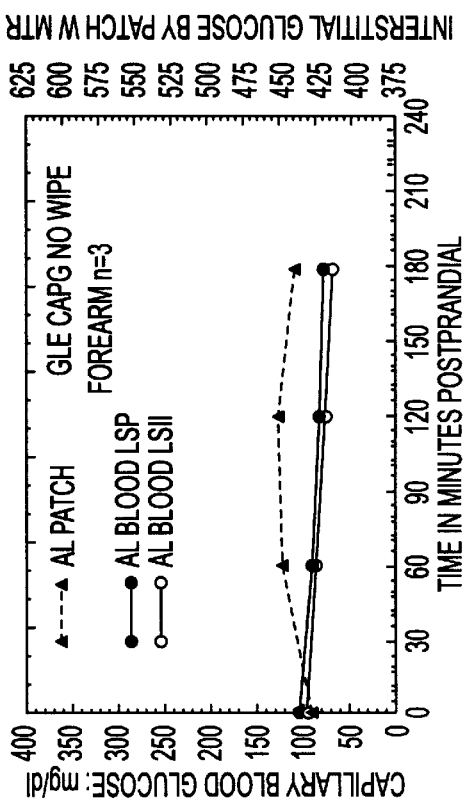

FIG. 41 is a plot of data which compares the results obtained from a noninvasive transdermal patch of the present invention with results obtained from capillary blood glucose utilizing standard method.

Figure 42:
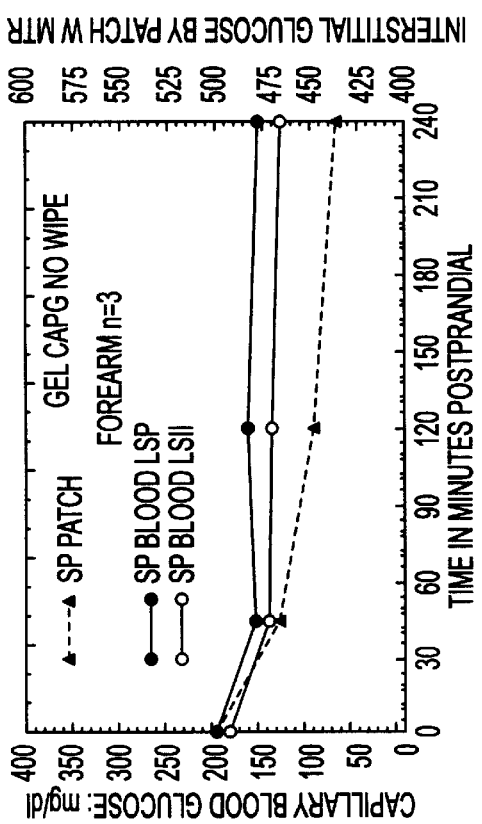

FIG. 42 is a plot of data which compares the results obtained from a noninvasive transdermal patch of the present invention with results obtained from capillary blood glucose utilizing standard method.

Figure 43:
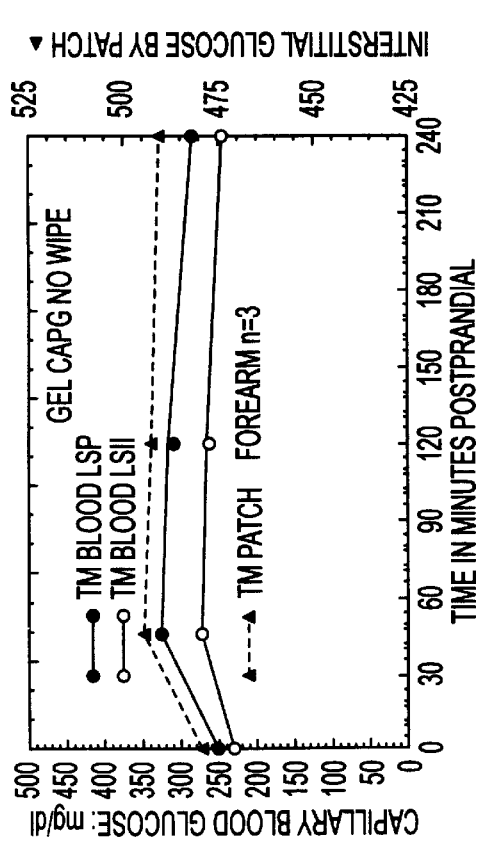

FIG. 43 is a plot of data which compares the results obtained from a noninvasive transdermal patch of the present invention with results obtained from capillary blood glucose utilizing standard method.

Figure 44:
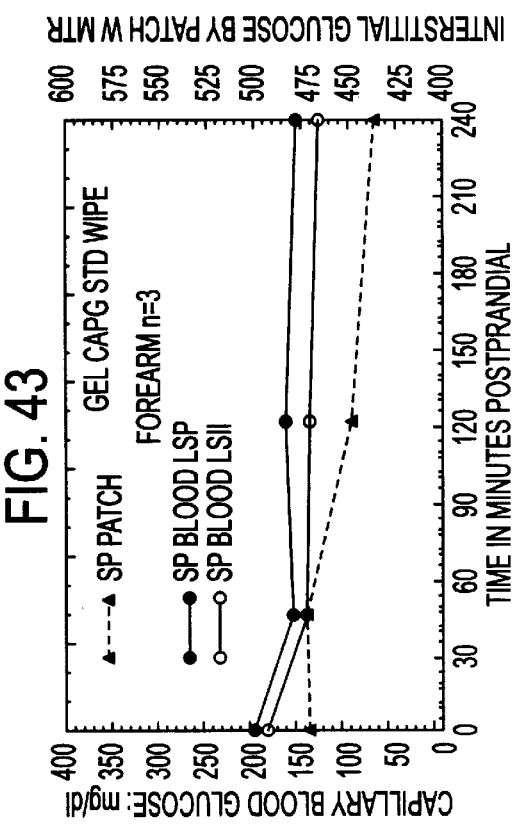

FIG. 44 is a plot of data which compares the results obtained from a noninvasive transdermal patch of the present invention with results obtained from capillary blood glucose utilizing standard method.

Figure 45:
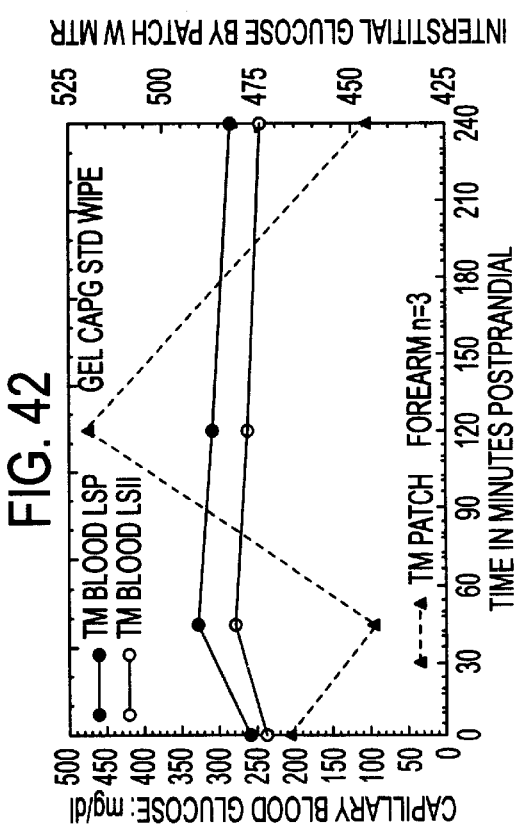

FIG. 45 is a plot of data which compares the results obtained from a noninvasive transdermal patch of the present invention with results obtained from capillary blood glucose utilizing standard method.

Figure 46:
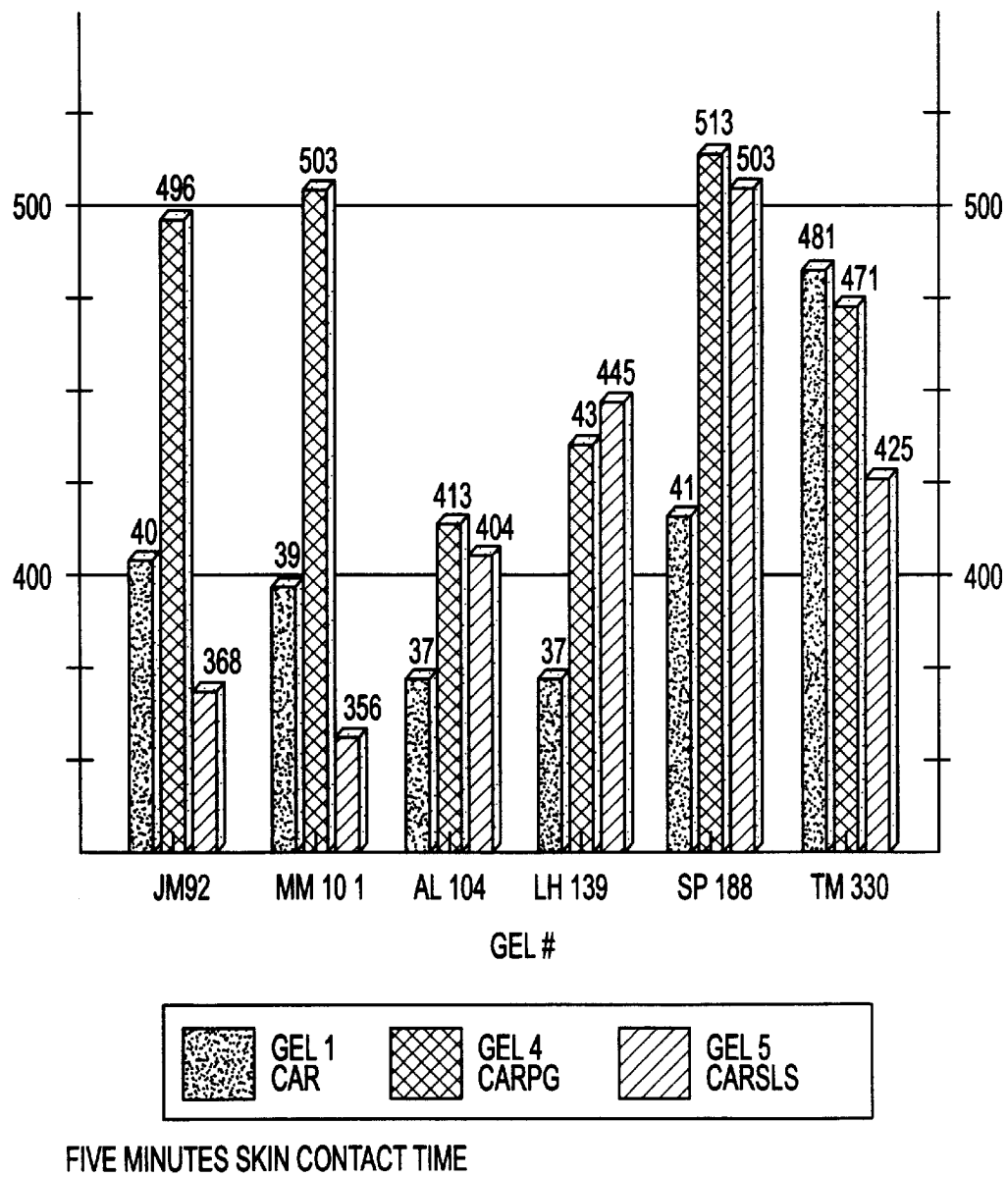

FIG. 46 is a bar graph of data showing the effectiveness of different gels without the use of wipes in noninvasive transdermal glucose patches of the present invention.

DETAILED DESCRIPTION OF THE INVENTION

By way of illustrating and providing a more complete appreciation of the present invention and many of the attendant advantages thereof, the following detailed description and examples are given concerning the novel methods, formulations and configurations.

Figure 2:
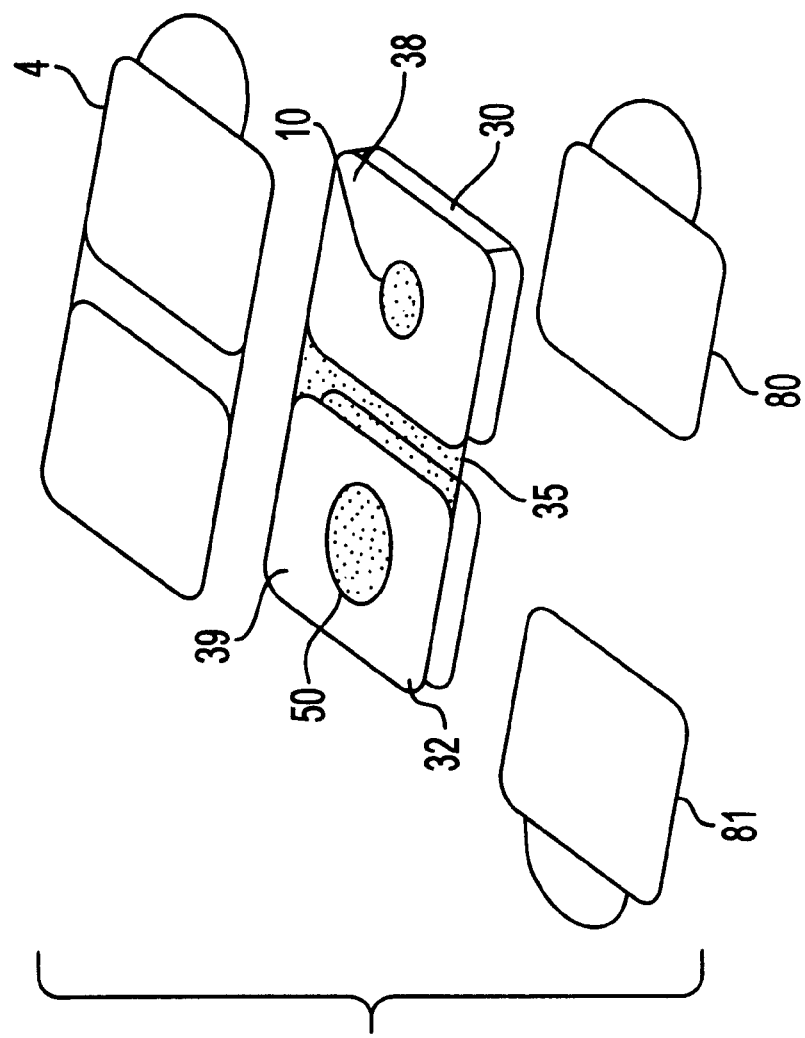
FIG. 2 is an exploded elevational view of an alternative noninvasive transdermal patch of FIG. 1A in accordance with the present invention.

Referring now to the FIGS. in detail and first, particularly to FIGS. 1A, 1B, 1C and 2 thereof, there is depicted an exemplary noninvasive transdermal patch of a multi-layer composite construction in accordance with the present invention, designated generally as 1, which is in a rounded rectangle clam shell shape. The noninvasive transdermal patch 1 includes two separate housing 30, 32 and an outer pulltab layer 4 on the frontal side of device 1. Therefore, patches of similar shapes, such as rectangular-shaped patches with square corners, are likewise contemplated by the present invention. The outer pulltab layer 4 and separate housing 30 and 32 function to keep the wet chemistry component 10 and the dry chemistry component 20 separate from one another, dry and uncontaminated during non-use. The outer pulltab layer 4 also functions on the upper-outer most protective layer to which a pressure sensitive adhesive layer 5 is affixed. The outer pulltab layer 4 may be formed of an air, moisture and light barrier material, such as a pink foil supplied by 3M Pharm. under the name Scotch Pak, product number 1006 KG90008, which is about 0.010 inches thick. The adhesive layer 5 may be a pressure sensitive adhesive, such as a double coated Medium tape on liner, product number 3M 1522796A and obtained from Sunshine Tape, which is approximately 0.005 inches in thickness. Adhered to the outer pulltab layer 4 are two separate housings 30, 32, each connected by hinge 35. Housing 30 contains a through aperture 31 for receiving and maintaining the wet chemistry component 10, whereas housing 32 includes a through aperture 33 for visualizing the dry chemistry component 20 as depicted in FIG. 1B and FIG. 2. As indicated above, aperture 33 should be of such a dimension and the reading head should be so configured that they interface precisely during use to maximize the reflectometer's ability to read the color intensity to detect the analyte. In addition to receiving wet chemistry 10 in through aperture 31 of housing 30, housing 30 functions to maintain the wet chemistry component 10 in aperture 31, so that the wet chemistry component 10 remains in contact with the dry chemistry component 20 during use. In this regard, it should be appreciated that the gels of the present invention should be formulated with a gel consistency sufficient to keep the gel in the aperture 31 during storage and use and to permit the analyte to pass through to the dry membrane for detection. Thus, if the gels of the present invention are too viscous, they will interfere with detection. On the other hand, if the gels are not sufficiently viscous, they will simply leak out of and away from the patch during testing, thereby preventing detection of the analyte.

The function of through aperture 33 in housing 32 is to permit visualization of the chemical reaction based on the differential colorimetric chemistry employed for a given analyte. In addition, through aperture 33 of housing 32 functions to receive the electronic interpretation component, such as a reflectance spectrophotometer, for visualizing the test reaction based upon the differential colorimetric chemistry electronically, as indicated above. While the dimensions of through apertures 31 and 33 may be of any suitable size, an exemplary size in accordance with the present invention is about 3/16 to about 4/16 inches in diameter. Preferably, housings 30 and 32 are manufactured with a cross-linked closed cell sponge impervious to moisture. More particularly, the cross-link closed cell sponge is a polyethylene foam, 12 lb density, type A, product number GL-187 acrylic psa, supplied by 3M Pharm. Alternatively, housings 30, 32 can be made of any other suitable materials such as nylon, rubber, etc.

Affixed to each housing 30, 32 is a continuous white mylar sheet 40 via adhesive 41. A suitable white mylar sheet is Dermaflex PM 500 supplied by Flexcon Co., Inc. The Dermaflex PM 500 is a white mylar sheet coated with TC200 to make it more printable and adhesive #525. Sandwiched between white mylar sheet 40 and housing 32 is a dry chemistry membrane 20. Adjacent the surface of white mylar membrane 40 and in contact with the dry chemistry membrane 20 is adhesive #525 of the Dermaflex PM 500 mylar sheet material. The Dermaflex PM 500 white nylon sheet is also coated on both sides with adhesive #525. White mylar sheet 40 is of a thickness of about 0.05 inches including the 50K6 liner. The white mylar sheet 40 is equipped with through apertures 55 and 56. Through apertures 55 and 56 permit the wet chemistry component 10 to be in continuous contact with the dry chemistry membrane 20 when housings 30 and 32 are folded together at hinge 35, as depicted in FIG. 3A. Affixed to the dorsal side 41 of white mylar sheet 40 is a bottom pull cover 70. Bottom pull cover 70, like outer pulltab layer 4, is formed of a similar pink foil which also functions as an air, moisture and light barrier.

To use the noninvasive transdermal patch 1, as depicted in FIGS. 1A, 1B and 1C, the subject preferably first cleans the area of skin to which the test patch device is to be applied. The skin may be cleansed with, for example, deionized water by rinsing. Once the area of skin is properly and thoroughly cleansed and dried, a skin permeation enhancer may be directly applied to the cleansed area. As indicated hereinabove, however, if a skin permeation enhancer is embodied in the wet chemistry component 10, it is not necessary to also apply a skin penetrator to the skin. Before applying the noninvasive transdermal patch 1 to the cleansed skin area, both outer pulltab 4 and bottom pulltab cover 70 are removed. Once outer pulltab 4 and bottom pulltab cover 70 are removed, housings 30 and 32 are folded along hinge 35, so that dorsal surfaces 36, 37 of housings 30, 32, respectively, are brought into direct contact with one another, so that the wet chemistry component 10 is now in contact with the dry chemistry membrane 20, as depicted in FIG. 1C, to ensure continuous and uniform wetting of the dry chemistry component or super sensitive or conditioned membrane 20. In other words, through aperture 31 of housing 30 and through aperture 33 of housing 32 are now in perfect alignment. Frontal surface 38 of housing 30 is then directly applied to the cleansed skin area, so that the wet chemistry component 10 is in constant contact with the cleansed skin area during testing for transferring the analyte from the biological fluid within or underneath the skin, such as the interstitial fluid, to the dry chemistry membrane 20 for chemical reaction indicator molecular formation and analyte detection. While depicted in FIGS. 1A, 1B or 1C, frontal surface 38 may include a pressure sensitive adhesive for adhering the patch to the skin during testing.

Exemplary dimensions of the noninvasive transdermal patch 1, when in a folded operable condition as depicted in FIG. 1C, are as follows. The width is approximately 0.750 inches and the length is about 0.75 inches, the diameter of the through apertures 31, 33 is between about 0.1875 and 0.25 inches, and the height or thickness is about 0.125 inches.

Alternatively, the rounded rectangle clam shell shaped noninvasive transdermal patch I may further include bottom and top pulltabs 80, 81, respectively, sandwiched between the outer pulltab layer 4 and frontal surface 38 of housing 30 and frontal surface 39 of housing 32 as depicted in FIG. 2. When such top and bottom pulltabs 80, 81 are utilized, the sequence of events during use is as follows. Following skin cleaning, the outer pulltab layer 4 and the bottom pulltab cover 70 are removed as before. However, the bottom pulltab 80 is then removed and frontal surface 38 of housing 30 is applied to the cleansed skin area. After a period of time of about 3 to about 15 minutes, top pulltab 81 is removed and the formal indicator molecule (color change) is observed either visually by the user or by an electronic detector component to confirm the presence of the analyte, as described herein before. The bottom and top pulltabs 80, 81 may also be made of a similar white mylar sheet material as membrane 40 referenced above.

While the patches depicted in FIGS. 1A, 1B and 1C are rectangular in shape with rounded corners, the patch of FIGS. 1A, 1B and 1C is exemplary of patches contemplated by the present invention.

While there is no set length of time which the noninvasive transdermal test patch devices of the present invention must be applied, it is generally believed that a time of about 3 to about 15 minutes, and preferably from about 4 to 6 minutes, and most preferably about 5 minutes is believed to be sufficient to develop proper analyte transfer and reaction for reliable detection and quantification. Moreover, while the noninvasive transdermal patches of the present invention can be applied to any suitable skin area from which an analyte of interest can be extracted from a biological fluid within or underneath the skin, such as the arms, under arms, behind ears, legs, inside portions of legs, fingertips, torso, etc., it is preferable to place the noninvasive transdermal patches on an area of skin free of hair, such as on the forearms and, in particular, the right or left volar portions of the forearm.

Figure 3:
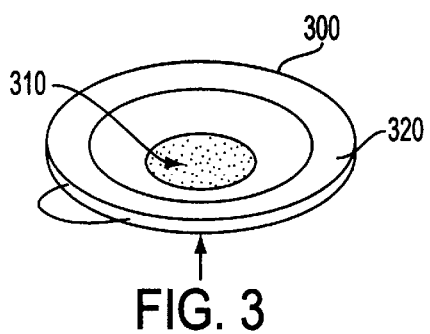
FIG. 3 is a perspective view of a noninvasive transdermal patch according to yet another embodiment of the present invention.

Configurations depicted in FIGS. 2–8 constitute further alternative embodiments of noninvasive transdermal patches of the present invention. For example, FIG. 3 depicts a round-shaped flat patch comprising an outer shell 300 comprised of a dry chemistry membrane 310 shown in the center of housing 320. The dry chemistry component 310 is a membrane saturated with a chemical reagent system for interaction and detection of an analyte of interest. In use, the targeted skin area is precleansed and then optionally treated with a skin permeation enhancer. Flat patch 300 is then removed from its foil packaging with desiccant (not shown) and a selected wet chemistry gel component (not shown) is applied on the back of membrane 310, which is then applied to the pretreated skin area for a sufficient period of time to enhance analyte transfer from the biological fluid within or beneath the skin to the dry chemistry membrane 310 for analyte detection.

Figure 4:
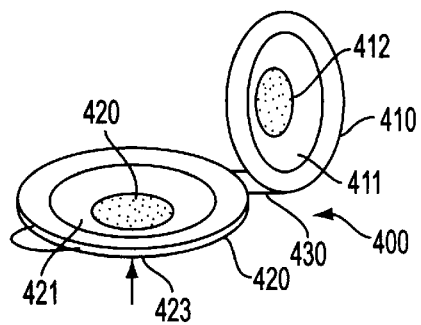
FIG. 4 is a perspective view of a noninvasive transdermal patch according to another embodiment of the present invention.

FIG. 4 depicts yet another example of a noninvasive transdermal patch in accordance with the present invention. In FIG. 4, a clam shell patch 400 is disclosed which includes a top housing 410 and a bottom housing 420. Top housing 410 contains the dry chemistry membrane 412 and bottom housing 420 contains the wet chemistry component or gel 422. Housings 410 and 420 are preferably connected by hinge 430 and each includes a concave interior surface 411 and 421, respectively, which complement one another. In use, the targeted skin area is precleansed and optionally treated with a skin permeation enhancer. Following skin pretreatment, the cover (not shown) is removed from the clam shell patch 400 and it is closed, so that the dry chemistry membrane 412 is in now contact with the wet chemistry component or gel 422 to ensure continuous and uniform wetting of the dry chemistry membrane 411. The bottom 423 of wet chemistry component or gel 422 is then applied to the pretreated skin area for sufficient time to permit interaction between the analyte under investigation and the chemical reagent system saturated on the dry chemistry membrane 412 for analyte detection.

Figure 5:
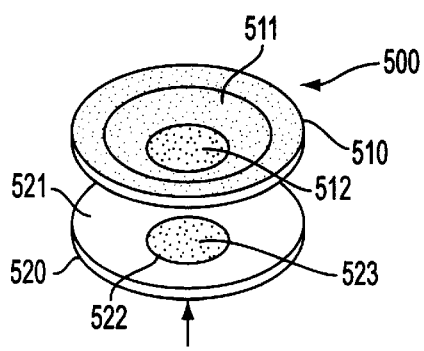
FIG. 5 is an exploded elevational view of a noninvasive transdermal patch according to yet another embodiment of the present invention.

Turning now to FIG. 5, it discloses a squeezer patch 500 in accordance with the present invention, which comprises two separate housings 510 and 520. Both housings 510 and 520 are circular in shape and have concave interior surfaces 511 and 521, respectively, which complement one another. Housing 510 includes the dry chemistry membrane 512 and housing 520 contains the wet chemistry component 522. In addition, the wet chemistry component or gel 522 includes a small hole 523 which activates the chemistry when it is squeezed. In use, the targeted skin area is precleansed and optimally treated with a skin permeation enhancer. The squeezer device 500 is removed from its foil packet with desiccant (not shown), and housing 510 is inserted into housing 520 so that the dry chemistry component 512 and the wet chemistry component or gel 522 are in contact with one another. The two housings 510 and 520 are squeezed to activate the chemistry and to continuously and uniformly wet the dry chemistry membrane 512. The bottom of the wet chemistry component or gel 512 is applied to the pretreated skin area for a sufficient time to permit analyte transfer from the biological fluid within or underneath the skin to the dry chemistry membrane 512 for analyte detection.

Figure 6:
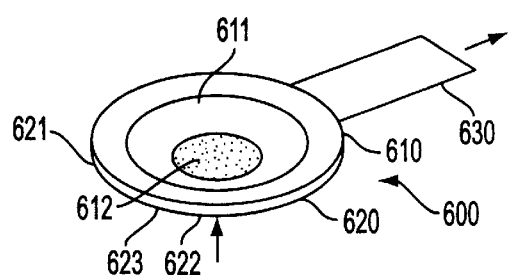
FIG. 6 is a perspective view of a noninvasive transdermal patch according to another embodiment of the present invention.

FIG. 6 depicts, as a further alternative, a slider patch 600. In accordance with the present invention, slider patch 610 comprises top housing 610 and bottom housing 620. Pulltab 630 is sandwiched between top and bottom housings 610 and 620, respectively. Housing 610 includes the dry chemistry membrane 612 and bottom housing 610 contains the wet chemistry component or gel 622. Pulltab 630 can be made of any suitable material which maintains an impenetrable barrier between dry chemistry membrane 612 and wet chemistry agents or gel 622 during nonuse. Preferably the interior surfaces 611 and 621 of housings 610 and 620, respectively, are concave in shape and match one another, so that when pulltab 630 is removed, the dry chemistry component 612 and the wet chemistry component 622 are in constant contact for continuously and uniformly wetting the dry chemistry component 612. To use, the targeted skin area is precleansed and pretreated with a skin permeation enhancer, if necessary. The slider patch 600 is then removed from the foil packet with desiccant (not shown) and pulltab 630 is removed to activate the chemistry between the dry and wet components 612 and 622, respectively. The bottom of the wet chemistry component 623 is then applied to the pretreated skin area for a sufficient amount of time for analyte detection of an analyte in a biological fluid located within or beneath the skin.

Figure 7:
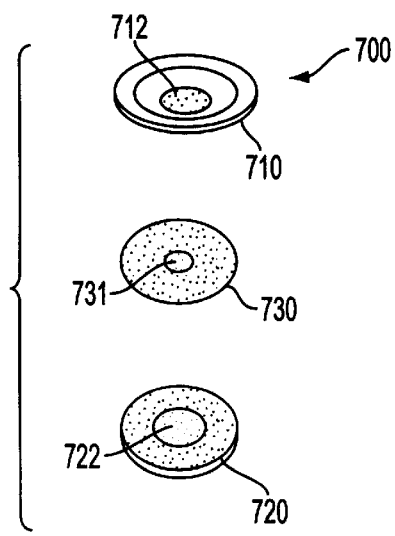
FIG. 7 is an exploded elevational view of a noninvasive transdermal patch according to yet another embodiment of the present invention.

In FIG. 7, a piercer patch 700 in accordance with the present invention is illustrated. The piercer patch 700 comprises housings 710 and 720 and piercer disk 730. Housing 710 includes a dry chemistry membrane 712 and 720 contains the wet chemistry component or gel 722. Piercer disk 730 includes sharp points 731 for nicking foil, into which the wet chemistry component 722 is packed and stored (not shown), to release the wet chemistry component 722 to continuously and uniformly wet the dry chemistry membrane 712. The piercer disk 730 and sharp points 731 can be made of any suitable material, such as metal or plastic. In use, piercer patch 700 is removed from the foil packet with desiccant (not shown) and the targeted skin area is precleansed and, optionally, pretreated with a skin permeation enhancer. The piercer patch 700 is activated by pressing housings 710 and 720 together so that the sharp points pierce the foil (not shown) between housings 710 and 720 to release the wet chemistry components in contact with one another. The bottom surface of the wet chemistry component 722 is then applied to the skin area for a sufficient period of time for analyte detection.

Figure 8:
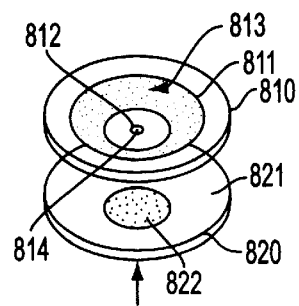
FIG. 8 is an exploded elevational view of a noninvasive transdermal patch according to yet another embodiment of the present invention.
Figure 9:
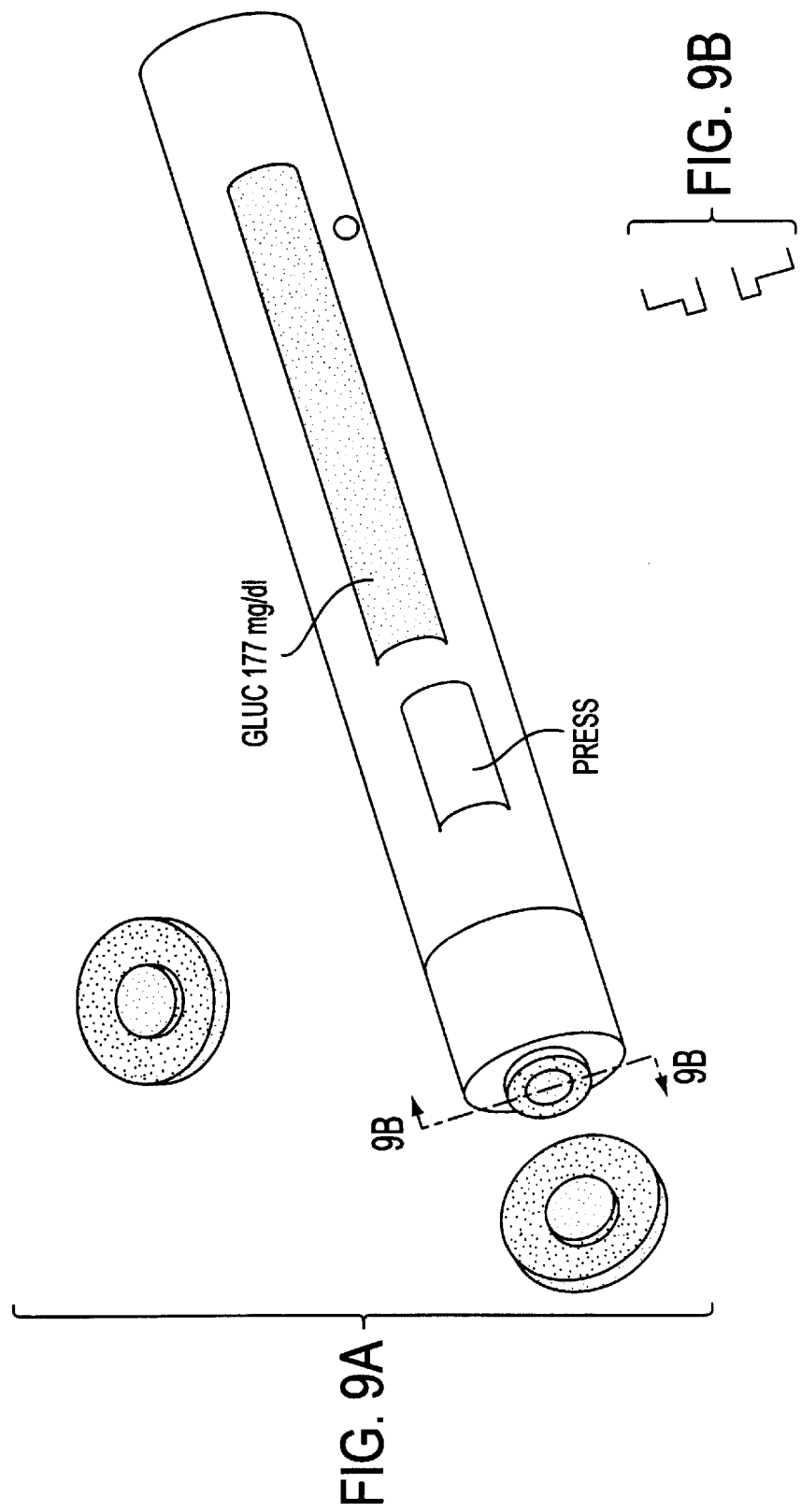
FIG. 9 is a perspective view of a reflectometer in accordance with the present invention.
Figure 10:
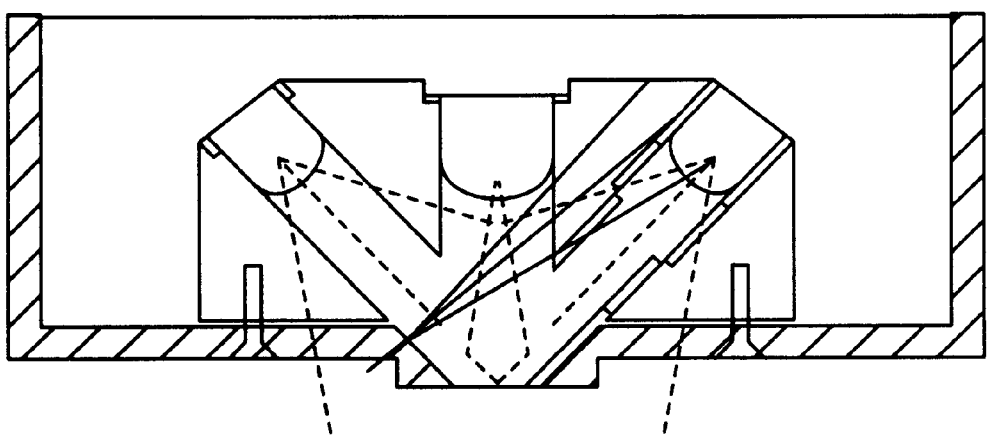
FIG. 10 is a cross-sectional view of the reading head of the reflectometer of FIG. 9.

Turning now to FIG. 8, it discloses a radial flow immunoassay patch 800 which comprises two separate housing 810 and 820. Both housings 810 and 820 are circular in shape and have concave interior surfaces 811 and 821, respectively, which complement one another. Housing 810 includes the dry chemistry membrane 812 and a donut 813 of absorbent material, such as diagnostic paper number 470 supplied Schleichr and Schull and housing 820 contains the wet chemistry component 822. Wet chemistry component 822 is pre-wet with a conjugate disk monoclonal antibody such as anti-BHCG. In addition, the dry chemistry component or gel 812 includes a small spot of antibody, such as AHCG, thereon for detecting the antigen. In use, the targeted skin area is precleansed and optimally treated with a skin permeation enhancer. The device 800 is removed from its foil packet with desiccant (not shown), and housing 810 is inserted into housing 520 so that the wet chemistry component 812 and the wet chemistry component or gel 822 are in contact with. one another. The two housing 810 and 820 are squeezed together to activate the chemistry component 812. The bottom of the wet chemistry component or gel 812 is applied to the pretreated skin area for a sufficient time to permit analyte transfer from the biological fluid within or underneath the skin to the dry chemistry membrane 812 for analyte detection.

It should be understood to those of skill in the art that the above alternative patches depicted in FIGS. 3–8 represent examples of various patch configurations in accordance with the present invention. It should be further understood that these exemplary patch configurations do not constitute the only patch variations contemplated by the present invention; but rather, the present invention contemplates any patch configuration which accomplishes the objectives of the instant invention. Moreover, it should be understood that the exemplary patch configurations depicted in FIGS. 3–8 can be made from, for example, the materials and chemical reagent systems discussed herein or any other suitable materials within the ambit of those skilled in this field.

As discussed above, the noninvasive transdermal systems of the present invention include a wet chemistry component comprised of a transfer medium which allows for liquid bridge transfer of an analyte of interest from the biological fluid within or beneath the skin to the dry chemistry component for biological reaction with the chemical reagents to release or form a reporter or indicator molecule (color change), which is indicative of the presence of the analyte in the biological fluid. In accordance with the present invention, the wet chemistry component is in the form of gel layer and is present in an amount of about 20 mcls to about 35 mcls, and preferable in an amount of about 25 mcls. In a preferred embodiment, the gel layer is a hydrophobic gel. A preferred hydrophobic gel is one formed with carboxy polymethylene, Carbopol™, in a concentration of from about 0.5% to about 2%. A preferred hydrophobic gel in accordance with the present invention is an about 1% carboxy polymethylene, Carbopol™ gel. It should be appreciated that while a carboxy polymethylene gel matrix is preferred, any other suitable gels prepared from, for example, carboxy methylcellulose, agarose and 10% glycerin 1% carboxy polymethylene in $dH_2O$, 10% polyethylene glycol in 1% carboxy polymethylene in $dH_2O$, and 10% sodium lauryl sulfate and 1% carboxy polymethylene in $dH_2O$, etc., may be utilized so long s they have the proper viscosity and do not interfere with analyte transfer or detection.

In a further feature of the present invention, the wet chemistry component may include a skin permeation enhancer. Examples of skin permeation enhancers that may be included within the wet chemistry component are propylene glycol, distilled water, deionized water, DMSO, isopropyl alcohol, ethyl acetate, ethyl alcohol, polyethylene glycol, carboxy methylcellulose, 1:1-water:acetonitrile, 1:1:1-ethanol:propylene glycol:$dH_2O$, 1:1-ethanol:propylene glycol, 70:25:5-ethanol:$dH_2O$:olcic acid, 70:25:5-ethanol:$dH_2O$:isopropyl palmitate, 1:1-ethanol:water, 75% lactic acid in isopropyl alcohol, 90% lactic acid and 10% Tween 20% salicylic acid in 50% isopropyl alcohol in $dH_2O$, 1:1:1-ethyl acetate:isopropyl alcohol:$dH_2O$, etc.

In preparing the wet chemistry component or gels of the present invention, it is generally preferable when making; for example, a hydrophobic gel to sprinkle the hydrophobic, such as carboxy polymethylene, slowly with slow mixing to avoid bubbles, followed by deaeraltion by vacuum. Autoclave, when appropriate, may be utilized for sterilization.

An especially preferred hydrophobic gel with a skin permeation enhancer incorporated therein comprises about, 1% carboxy polymethylene, Carbopol® and about 10% propylene glycol. Such a preferred hydrophobic gel can be prepared by slowly spinkling and mixing about 1 g of Carbopol™ 1342 (BF Goodrich) in a total of about 100 ml of deionized water containing about 10% propolyene glycol. During mixing, bubbles should be avoided. Following mixing, the gel is deaerated by vacuum.

It should be understood by those of skill in the art that while transfer mediums containing skin permeation enhancers, are preferred, it is not necessary to incorporate skin permeation enhancers into the transfer medium. Alternatively, the present invention envisions the use of transfer mediums, e.g., a hydrophobic gel which is free of a skin permeation enhancer. An example of such a transfer gel is a 1% carboxy polymethylene gel or a 1% carboxy methylcellulose gel as mentioned hereinabove. Nevertheless, it should be understood, that when a skin permeation enhancer is embodied into the transfer medium, the use of a separate skin permeation enhancer on the skin prior to the application of the noninvasive transdermal patch is optional. However, when a transfer medium free of skin permeation enhancer is selected, as the wet chemistry component 10 in accordance with the present invention, the skin is preferably pretreated with a skin permeation enhancer. A preferred skin permeation enhancer contemplated by the present invention is propolyene glycol or a 1:1:1 mixture of isopropyl alcohol, deionized water and ethyl acetate, which can be prepared by simply mixing the three components together. Other skin permeation enhancers that may be used in accordance with the present invention include DMSO, ethyl alcohol, distilled water, deionized water, propylene glycol, isopropyl alcohol, lactic acid, ethyl acetate, carboxyl methylcellulose, etc. Of course, it should be understood that when a skin permeation enhancer is selected, it should be applied to the skin area, which will undergo testing in advance, in a sufficient quantity and for a sufficient period of time prior to the application of the noninvasive transdermal system, so that if the skin permeation enhancer may act in an effective manner to assist in the transfer of the analyte of interest in a biological fluid, such as interstitial fluid, or detection by the dry chemistry component 20 of the present invention. While the quantity and time will vary depending upon the skin penetrant selected, the skin permeation enhancer should be applied in an amount that will permit it to rapidly dry within a short period of time to avoid excess accumulation at the targeted skin site. It should also be appreciated that when a skin permeation enhancer is selected for use in accordance with the present invention, the analyte under investigation should be taken into consideration so that a skin penetrant is not selected which will somehow interfere with the analyte of interest or its detection. For example, a cellulose-type skin permeation enhancer may be incompatible when the analyte under investigation is glucose.

The dry chemistry component 20 of the present invention is comprised of a novel super sensitive or conditioned membrane (a dry chemistry membrane) which, in general, is approximately at least 100 times, and as much as 400–500 times, more sensitive than those dry chemistry membranes currently used to detect an analyte in whole blood. In fact, and quite surprisingly, it has been discovered that, a super sensitive or conditioned membrane has the ability to detect and quantify accurately and quickly the analyte under investigation even though they are in very small concentrations, insufficient at times for detection for HPLC methods. While any suitable material may be utilized as the base material for the super sensitive or conditioned membranes of the present invention, such as mylar materials, like BioDyne A or BioDyne B supplied by Paul Gelman, an especially preferred material is polyether sulfone distributed under the product name Supor 450™ by Gelman Sciences. This particular polyether sulfone material has a thickness of about 0.45 microns. While this particular polyether sulfone material is preferred, it is nevertheless believed that other polyether sulfone materials may be utilized, such as nylon, having a thickness of about 0.8 microns.

A typical super sensitive or conditioned membrane in accordance with the present invention comprises a glucose reactive formulation for a noninvasive transdermal glucose patch. The glucose reactive formulation comprises a base preparation and an enzyme component as follows:

| Glucose Reactive Formulation for Glucose Patch Base preparation. 100 ml | |
|---|---|
| 6.0 gm | Polyvinyl Pyrrolidinone K-30 [mw 40,000] (Sigma Chemical) |
| 1.2 gm | Citric Acid Trisodium Salt (Aldirch) |
| 0.10 gm | Citric Acid Monohydrate |
| 0.028 gm | NaBH4 [Sodium Borohidrate] |
| 0.10 gm | Bovine Serum Albumine [BSA] |
| 0.545 gm | O-Tolidine (Sigma Chemical) adjust pH to 5.9–6.0 |

-continued

| Glucose Reactive Formulation for Glucose Patch Base preparation. 100 ml | |
|---|---|
| | Add 2.0 ml 10% Gantrez S-95,2 Butendonic [10/0 gm/100 ml] (ISP Technologies) adjust pH to 5.9–6.0 with NaOH |
| 4.0 gm/L | 75% Dioctylsulfosuccinate DOSS[0.533 gm] (Sigma Chemical) |
| 121.0 mg | Glucose Oxidase (GOD) 150 u/ml[150 u 100 ml/124 u/mg] (Fynn Sugar) |
| 38.53 mg | Horse Radish Peroxidase (POD) 100 u/ml [100 u 100 ml/259.55 u/mg] (Worthington) |

The glucose reactive formulation can be prepared as follows. First, prepare the base preparation by intimately mixing the ingredients recited above with one another. Second, mix O-Tolidine in deionized water until dissolved. Third, prepare an enzyme solution its follows. Into a clean suitable sized container, measure the calculated enzyme solution. Slowly add the prepared O-Tolidine to the base solution while mixing until solution is clear. While mixing, add the 20% Gantrex and mix for approximately 15–20 minutes. Thereafter add the DOSS while mixing and continue to mix for an additional 15–10 minutes. Adjust the pH using NaOH to 6.8–6.9. At this point, solution should be clear. Thereafter, add GOD to the clear solution while mixing. Once the GOD has been added, stop mixing and add the POD. Once the POD is dissolved, mix for an additional 15–20 minutes. The glucose reactive solution is now ready for use. During preparation, the mixing should be done in such a way to prevent foaming, so as to avoid denaturing the BSA. It should be appreciated by those of skill in the art that because the glucose reactive formulation contains excessive quantities of both the enzymes and chromophore, O-Tolidine, the base preparation is needed in the preparation to dissolve the excessive amounts of the chromopore, O-Tolidine, and enzymes.

A super sensitive or conditioned glucose reactive membrane may be prepared as follows. A sheet of the polyether sulfone or other material is submerged into the glucose reactive solution as prepared above, at an angle of about 45° to drive air out of the membrane material while introducing the glucose reactive solution into the membrane material. Slowly pull the membrane material through the solution to saturate the membrane material. The wet, saturated membrane material is then dried by passing it through a conventional 10 foot-long drier at a temperature of less than about 41° C. at a speed of about 2 feet/minute or for about 5 minutes. Once dried, the top and bottom ends of the super sensitive or conditioned membrane should be removed because of the unevenness of the saturation at the top and bottom ends. The super sensitive or conditioned membrane is now available for use as the dry chemistry membrane 20 of the present invention.

An alternative glucose reactive membrane may be prepared as follows:

Dry chemistry strips are prepared, in accordance with the process of this invention, from the following materials and reagents:

(a) Membrane
   1.) Gelman Sciences, Ann Arbor, MI, Polyethersulfone (Supor) Porosity 0.22–0.8 microns
(b) Indicator about 1% (w/w) aqueous solution deionized water O-Tolidine hydrochloride (c) Glucose Specific Reagent Cocktail
  1.) glucose oxidate 125 IU activity per mil
  2.) peroxidase 50 IU of activity per ml
  3.) albumin 0.2% (w/v) (enzyme stabilizer)
(d) conditioning and flow control agents—polyvinyl pyrolidone 3% (w/v) dioctylsulfosuccinate 0.2% and 2 Butendioic acid polymer (0.35%) all buffered with 0.1 m citrate, (pH 6.4)

Each of the above reagents are prepared fresh from reagent grade chemical and deionized water. They are mixed together as one homogenous solution and the membrane is dipped briefly (about 30 seconds) into it until uniformly wetted. It is then air dried at 37° C. for about 15 minutes. The dried membrane is stored with desiccant protected from moisture and light. This dry chemistry membrane is cut into strips and can be encapsulated, (i.e. glued) within the fold of an adhesive coated mylar that is then affixed within the device. It is believed that when this alternative glucose formulation and process are selected, approximately 5 liters will effectively coat a. membrane, such as a BioDyne A membrane.

It has been surprisingly found that the above described glucose reactive membranes have the unique ability to detect as little as about 1 mcg/5 ml or 0.005 mcg/25 mcl glucose in the wet chemistry component. It can now be readily appreciated by those of skill in this art that the novel noninvasive transdermal patches of the present invention are quite capable of accurately, reliably and quantitatively detecting glucose in a subject. Moreover, the novel noninvasive transdermal patches of the present invention are simple and easy to use by nonmedically trained personnel while eliminating the need for invasive, painful techniques utilized heretofore. Those skilled in this art should therefore readily appreciate that the novel noninvasive transdermal patches of the present invention provide a significant advancement over the prior systems and techniques concerning the body fluid analyte collecting and detection.

While the dry chemistry membrane 20 of the present invention is described herein with particular reference to a certain glucose membrane, it should nevertheless be understood that any other suitable membrane may be employed in accordance with the present invention, such as those described and illustrated in U.S. Pat. No. 4,774,192, which is incorporated herein by reference in its entirety. It should also be understood by those of skill in the art that, while the above-discussed super sensitive or conditioned membranes are prepared with the chromophore, O-Tolidine, any other suitable chromophore, such as tetra-methyl benzidine (TMB), may be employed. It should also be appreciated that other indicator systems, such as fluorphores or polarographic or enzyme electrodes, may be employed to detect the analytes with the noninvasive systems of the present invention, so long as the objectives of the instant invention are not defeated.

Moreover, it should be understood by those of skill in the art, that the above-discussion, with respect to glucose analysis of interstitial fluid, can by analogy be readily extrapolated to the preparation of super sensitive or conditioned membranes and performance of clinical assays for the detection of a wide variety of other analytes typically found in biological fluid samples, such as interstitial fluid. The super sensitive or conditioned membrane systems of this invention are, thus, applicable to clinical analysis of, for example, cholesterol, triglycerides, bilirubin, creatinine, urea, alpha-amylase, L-lactic acid, alanine aminotransferase (ALT/GPT), aspartate aminotransferase (AST/GOT), albumin, uric acid, fructose amine, potassium, sodium, chloride, pyruvate dehydrogenase, phenylalaninehydroxylase, purine nucleotide enzymes and phenylalanine hydroxylase or its substrates, such as phenylalanine, phenyl-pyruvate or phenyl-lactate, to name a few. The assay format can be essentially the same as that described previously for glucose, or optionally involve the combination of a conditioned membrane/reagent system with one or more additional lamina (i.e. spreading layer, radiation blocking layer, semipermeable diffusion layer, etc.).

The preparation of a conditioned membrane, incorporating a dry chemistry reagent system for each of the above analytes, follows essentially the same process as described for preparation of glucose specific dry chemistry reagent systems (e.g. conditioning the membrane with a flow control agent and the absorption of the indicator/reagent cocktail). The conditioning of thee membrane can, thus, occur prior to or concurrent with contact of the membrane with one or more of the constituents of the dry chemistry reagent systems.

Generally speaking, in an alanine aminotransferase (ALT/GPT) assay, the enzyme reacts with alanine and alpha-ketoglutarate to form pyruvate and glutamate. The pyruvate that forms reacts with 2,4-dinitro phenylhydrazine that is colored at 490–520 nm. High levels of alanine aminotransferase are associated with hepatitis and other liver diseases. In an aspartate aminotransferase (AST/GOT) assay, the enzyme reacts with aspartate 1 and 2-oxoglutarate to form oxaloacetate and glutamate. The oxaloacetate that forms reacts with 2,4-dinitro phenylhydrazine that is colored at 490–520 nm. High levels of oxaloacetate are associated with myocardial infarction hepatitis and other liver diseases as well as muscular dystrophy dermatomyositis. In an albumin assay, bromcresol purple binds quantitatively with human serum albumin forming a stable complex with maximum absorbance at 600 nm. Low levels of human serum albumin are associated with liver disease, nephrotic syndrome, malnutrition and protein enteropathies. High levels of human serum albumin are consistent with dehydration. Prealbumin may be of diagnostic value for diabetes and malnutrition. Normal values are 3–5 gm/dl (30–50gm/L). Critical limits for children are lows of 10–25 gm/L or highs of 60–80 gm/L. In a bilirubin assay, diazotized sulfanilic acid reacts quantitatively with conjugated bilirubin forming azobilirubin with maximum absorbance at 560 nm. High levels of bilirubin are associated with biliary obstruction and hepatocellular disease. In the presence of dimethyl sulfoxide (DMSO) both conjugated (direct) and unconjugated (free), bilirubin reacts and is then indicative of hemolytic disorders in adults and newborns. Critical limits for adults are highs of 5–30 mg/dl (86–513 micromol/L) and 86–342 micromol/L for children; normal levels are up to 0.3 mg/dl serum conjugated, but 1–12 mg/dl (96–308 micromol/L) for newborns. Patches in accordance with the present invention, after a few minutes, would read 1/50th of these values. In a chloride assay, mercuric thioisocyanate reacts with chloride ions to give mercuric chloride, the thiocyanate produced reacts with iron to give a reddish brown product. Low levels of chloride ions are associated with gastrointestinal or salt losing nephritis, Addisons disease. High levels are associated with heart failure and Cushing's syndrome. The critical limits are 60–90 mmol/L (1/50th of that is to be expected in a patch of the present invention). Normal levels are 95–103 mEq./L). In a cholesterol, total assay, cholesterol esters are reacted with cholesterol esterase. The total free cholesterol is further reacted with cholesterol oxides which in turn generates peroxide detected with peroxidase coupled to a colored dye O-Tolidine. Increased levels of cholesterol are associated with atherosclerosis, nephrosis, diabetes mellitus, myxedema, and obstructive jaundice. Decreased levels of cholesterol are observed in hyperthyroidism, anemia, malabsorption and wasting syndromes. Normal values are 150–250 mg/dl. (varies with diet and age). Values above 200 mg/dl would suggest consulting a physician. In a fructose amine assay, fructose amine reduces nitrotetrazolium blue at alkaline pH. Fructose amine is useful in the management of diabetes mellitus. Levels are indicative of glucose control. In a lactic acid assay, porcine lactate dehydrogenase (Boehringer Mannehim) reacts with lactate in the presence of nicotinamide adeninine dinucleotide (NAD) to produce NADH (NAD reduced) plus pyruvate. The NADH is then detected by using the enzyme diaphorase (Unitika) to react with a tetrazolium salt producing a colored formazan. The color produced is directly proportional to the lactic acid concentration. Lactic acid is useful in critical care situations, as a measure of the success of supportive therapies to predict the mortality rate. High levels correlate with severity of clinical outcome. Blood lactate has become a prognostic indicator of survival in patients with acute myocardial infarction and is also used as an indicator of severe neonatal asphyxia. Lactic acidosis is also found in patients with diabetes mellitus and hepatic failure. Can be used in sports medicine to evaluate endurance and fitness. Normal values are 5–20 mg/dl in venous blood; lower (3–7 mg/dl) in arterial blood. Critical limits are highs of 20.7–45 mg/dl (2.3–5.0 mmol/L). In a potassium assay, ion specific electrodes have become stable and sensitive enough to be used to detect the levels expected in a patch (critical limits are 1/50th of that found in the blood: i.e., 0.05–0.07 mmol/L) after a few minutes skin contact. Potassium is useful in critical care situations as a measure of the success of supportive therapies to predict the mortality rate. High levels of potassium correlate with severity of clinical outcome. Blood potassium has become a prognostic indicator of survival in patients with acute myocardial infarction. The normal values are 3.8–5.0 mEq./L (same as mmol/L) in plasma; critical limits are low 2.5–3.6 mmol/L or high of 5–8 mmol/L. In a sodium assay, ion specific electrodes have become stable and sensitive enough to be used to detect the levels expected in a patch (critical limits are 1/50th of that found in the blood after a few minutes skin contact. The normal values are 136–142 mEq./L (same as mmol/L) in plasma; critical limits are low of 110–137 mmol/L or heights of 145–170 mmol/L. In a triglycerides assay, triglycerides react with lipoprotein lipase giving glycerol that when phosphorylated produces peroxide in the presence of glycerol phosphate oxidate. This can be detected with a color dye and peroxidase with the noninvasive transdermal systems of the present invention. High levels of triglycerides are involved with nephrotic syndrome, coronary artery disease, diabetes and liver disease. Normal values are 10–190 mg/dl in serum. In an uric acid assay, uric acid reacts with uricase to form allantoic and peroxide that is detected by appropriate means. High levels of uric acid are associated with gout, leukemia, toxemia of pregnancy and sever renal impairment. Normal values are male 2.1–7.8 Mg./gl; female 2.(2.0–6.4 mg/dl. The critical limits are a high of 10–15 mg/dl (595–892 micromol/L).

Such examples of super sensitive or conditioned membranes which can be made in accordance with the present invention are now illustrated.

A super sensitive or conditioned membrane for urea can be prepared by absorption into a conditioned membrane, of appropriate, concentrations of urease, buffer, and an indicator sensitive to changes in pH. When a whole blood sample is brought in contact with the sample receptive surface of the membrane, the serum is taken up by the membrane. The urea present in the serum is digested by the urease enzyme, thereby liberating ammonia in solution. The ammonia can then react with a suitable indicator (i.e., a protonated merocyanide dye). The pH of the membrane is buffered to about 8.0 to keep the equilibrium concentration of the ammonia relatively low. The indicator is monitored at 520 nm. Additional details of this specific reagent system are described in the open literature, see for example Spayd, R. W. et al., *Clin. Chem.*, 24(8):1343.

A super sensitive or conditioned membrane for alphaamylase can be prepared by absorption, into a conditioned membrane, of appropriate concentrations of a derivatized substrate (i.e., starch) and buffer. When the whole blood sample is applied to the sample receptive surface of the test strip, the serum is absorbed into the membrane, thus, initiating digestion of the derivatized. substrate by the alphaamylase in the sample. This digestion of the substrate releases a chromophore or fluorophore which can be monitored in accordance with accepted techniques and readily available equipment. Additional details for this specific reagent system also appear in the Spayd publication, previously referenced herein.

A super sensitive or conditioned membrane for bilirubin can be prepared by absorption, into a conditioned membrane, of appropriate concentrations of certain cationic polymers (i.e., polymeric quaternary salts) and phosphate buffer (pH approximately 7.4). When an interstitial sample is applied to the sample receptive surface of the test strip, the fluid is absorbed into the membrane, thereby initiating interaction of the bilirubin and the cationic polymer. Such interaction results in a shift in the maximum absorption of the bilirubin from 440 to 460 nm with an accompanying substantial increase in absorption at the new peak. Additional details relating to this specific reagent system also appear in the previously referenced Spayd publication.

A super sensitive or conditioned membrane for triglycerides (triaclyglycerols) can be prepared by absorption, into a conditioned membrane, or surfactant, lipase, adenosine triphosphate (ATP), glycerol kinase and L-alpha-glycerol phosphate oxidase, and a triarylimidazole leuco dye. In brief, the surfactant aids in dissociation of the lipoprotein complex so that the lipase can react with the triglycerides for form glycerol and fatty acids. The glycerol is then phosphorylated with the adenosine triphosphate in the presence of the glycerol kinase enzyme. The L-alpha-glycerol phosphate thus produced is then oxidized by the L-alpha-glycerol phosphate oxidase to dihydroxy acetone phosphate and hydrogen peroxide. The hydrogen peroxide oxidizes the lueco dye, producing a colored indicator which has a peak absorption at 640 nm. Additional details relating to this specific reagent system appear in the previously referenced Spayd publication.

An alternative and preferred chemistry reagent system for triglyceride analysis can be prepared by absorption, into a conditioned membrane, of lipase, glycerol dehydrogenase, p-iodonitrotetrozolium violet (INT) and diaphorase. The serum triglycerides initially interact with the chemistry reagent system and are hydrolyzed to free glycerol and fatty acids. The free glycerol is now converted to the dihydroxyacetone by glycerol dehydrogenase, in the presence of NAD. Simultaneous with such conversion, INT (colorless) is reduced by diaphorase, in the presence of NADH, to red dye (maximum gamma=500 nm). The change is absorbance of the test strip at 500 nm is directly proportional to the concentration of serum triglycerides.

A super sensitive or conditioned membrane for determination of total cholesterol in interstitial fluid can be prepared by absorption, into a conditioned membrane, of cholesterol ester hydrolase, cholesterol oxidase, a leuco dye and peroxidase. Upon application of a whole blood sample to the sample receptive surface of the test strop, the serum is absorbed into the membrane, thereby initiating conversion of the cholesterol esters to cholesterol, the oxidation of the cholesterol is accomplished by the cholesterol oxidase enzyme, thereby liberating peroxide. The peroxide and leuco dye then interact in the presence of peroxidase to form a highly colored indicator which can be monitored either visually or through the use of instrumentation. Additional details relating to this specific reagent system appear in the open literature, see Dappen, G. N., et al. Clin. Chem., Vol 28, No. 5(1982), 1159.

Alternatively, a super sensitive membrane for detection of total cholesterol in interstitial fluid can be prepared, in accordance with this invention, from the following materials and reagents:

(a) Membrane
   1) Corning Costar, Cambridge, Mass., Bioblot nylon plus Porosity 0.22–0.8 microns
(b) Indicator about 1% (w/w) aqueous solution deionized water Tetramethylbenzidine
(c) Cholesterol Specific Mixed Reagent Cocktail
   1) Cholesterol oxidase 150 IU activity per ml
   2) Cholesterol esterase 150 IU activity per ml
   3) peroxidase 50 IU of activity per ml
   4) stabilizer for the enzyme-albumin 0.2% (w/v)
(d) conditioning and flow control agents-polyvinyl pyrolidone 3% (w/v) and dioctylsulfosuccinate 0.2% with 2 Butendioic acid polymer (0.35%) all buffered with 0.1 M citrate, (pH 6.4).

Each of the above reagents are prepared fresh from reagent grade chemical and deionized water. They are mixed together as one homogenous solution and the membrane is dipped briefly (about 30 second) into it until uniformly wetted. This is then air dried at about 37° C. for about 15 minutes. This is stored with desiccant protected from moisture and light. This dry chemistry membrane is cut into strips and encapsulated, (i.e. glued) within the fold of an adhesive coated mylar that is then affixed within the device.

In yet another alternative, a super sensitive or conditioned membrane for a cholesterol reactive formulation for cholesterol detection can be prepared from the following erzymatic solution preparation. The enzymatic solution preparation can then be formulated with the base preparation as described earlier hereinabove for the glucose reactive formulation for glucose patch.

| Cholesterol Enzymatic Solution Preparation | | | |
| --- | --- | --- | --- |
| To make 30 ml: | | | |
| O-TOLIDINE 5.45 gm/L | | 163.5 mg | |
| HORSERADISH PEROXIDASE | 14.3 U/mg [259.55] | | 1.65 mg |
| CHOLESTEROL OXIDASE 20.0 U/ml | | [25.1 U/mg] | 23.9 mg |
| CHOLESTEROL ESTERASE | 60.5 U/mg 160.0 U/mg | | 11.34 mg |

Once such a cholesterol reactive formulation is prepared, it can be air dried onto a suitable membrane material, such as a polyether sulfone membrane, Supor 450. supplied by Gelman Sciences or the BioDyne A or BioDyne B membranes supplied by Paul Gelman, and used with a wet chemistry component 10 of the present invention, such as the hydrophobic gel comprising about 1% carboxy polymethylene and about 10% propylene glycol.

A super sensitive or conditioned membrane for lactate detection can be prepared from, for example, the following formula, which is admixed with the base preparation described hereinabove for the glucose reactive formulation for glucose patch, and then saturated into a suitable membrane material such as a polyether sulfane Supor 450 membrane supplied by Gelman Sciences or a BioDyne A or BioDyne B membrane supplied by Paul Gelman.

| Lactate Reactive Formula for Lactate Patch | |
| --- | --- |
| Based on 100 ml | |
| PVP K-30 | 6.0% |
| K-PO$_4$ | 0.15 M |
| BSA | 0.10% |
| LDH (rabbit muscle) | 15000 U (Boehringer Mannehim) |
| NAD | 2.0 mM (Unitika) |
| Diaphorase II | 10000 U (Dojindo) |
| WST4 (tetrazolium) | 1.0 mM |

A super sensitive or conditioned membrane for creatinine can be prepared by absorption into a conditioned membrane of appropriate concentrations of creatinine imino hydrolase and an ammonia indicator (i.e., bromphenol blue). Upon application of an interstitial fluid sample to the receptive surface of the membrane, the interstitial fluid sample is absorbed into the membrane, thereby initiating interaction of the creatinine and the enzyme, creatinine amino hydrolase, resulting in the liberation of ammonia. The ammonia thereby reacts with the indicator and the color development monitored visually or with conventional instrumentation. Additional details relating to this specific reagent appear in the open literature, see for example Toffaietti, J., et al., Clin. Chem., Vol. 29, No. 4 (1983), 684. It is also contemplated that the dry chemistry reagent systems of this invention be utilized in a multiple lamina .test slide of the type developed by Eastman Kodak Company of Rochester, N.Y. (Hereinafter "Kodak format"). Where a permeable material (i.e. spreading layer) is placed in contiguous contact with the sample receptive surface of a treated membrane, such contract will influence (change) the rate and quantity of interstitial fluid transported through the membrane, and consequently the rate and extent of the reaction mediated by the analyte specific components within the membrane. At higher blood analyte levels the transport of sample across the membrane can result in an overabundance of analyte and thus a foreshortening of the usable range of measurement.

Also contemplated by the present invention is the adaption of the membrane to a displacement immunoassay of the type described in Liotta U.S. Pat. No. 4,446,232, which is hereby incorporated by reference in its entirety. In the configurations, the receptive surface of the membrane is coated with an enzyme labeled antigen or antibody (hereinafter "enzyme labeled conjugate"). The method of application of the coating of the receptive surface insures against penetration of the coating material into the matrix of the membrane. The balance of the immunochemistry reagent system, notably, a chromogenic or fluorogenic substrate for the enzyme is incorporated into the conditioned membrane, so as to preserve its physical isolation from the surface coating. The contact of the sample with the coating on the surface of the membrane results in displacement of enzyme labeled material. The displacement of the enzyme labeled conjugate is based upon the dynamic equilibrium which is caused by the presence of an analyte in the sample and the competition with the conjugate for binding to an analyte mimic in the surface coating.

This displaced enzyme labeled conjugate, along with a portion of the fluid fraction of the sample, is absorbed in the matrix of the membrane. The enzyme portion of this conjugate interacts with a substrate specific for the enzyme and thereby produces a discernible change in color or fluorescence which is indicative of the analyte of interest. This change can be observed visually, (in the case of color change) or by instrumentation designed for that purpose.

In practicing the present invention, the targeted skin area for testing should first be thoroughly cleansed. This can be accomplished by washing the area thoroughly with water by rinsing and then permitted to dry. Once cleansed, the skin permeation enhancer, if separately utilized, should be applied to that area of skin in a sufficient quantity and for a sufficient period of time. Typically, there is no set amount or but the amount applied should be generous. The time should be sufficient to permit the skin permeation enhancer to penetrate the skin to assist extraction of the body fluid such as interstitial fluid. This generally takes only a few seconds. Of course, if a skin permeation enhancer is selected, it should not in any way interfere with the analyte under investigation. Thereafter, the noninvasive transdermal system, such as the patch depicted in FIGS. 1A, 1B, 1C and 2, should be immediately applied, so that the wet chemistry component 10 is in direct and continuous contact with the cleansed skin area, which mayor may not have been pretreated with a skin permeation enhancer, and the dry chemistry component 20 is in direct and continuous contact with the wet chemistry component 10. Preferably, such application should be for a period of between about 3 and 15 minutes, preferably between about 4 to about 6, minutes and more preferably, about 5 minutes. Also, immediately prior to skin application, the wet and dry chemistry components 10 and 20, respectively, should be placed in contact with one another for purposes of continuously and uniformly wetting the dry chemistry component 20, so that reliable analyte detection can be made.

While not wishing to be limited to any particular theory or mechanism of action, it is believed that the underlying mechanism of the patch is as follows. First, chemicals in the patch temporarily dissolve the lipid barrier of the skin which seals the dead cells of the uppermost layer of the stratus corneum. This results in a penetration of the stratus corneum by converting it into a semi-permeable membrane through which the interstitial fluid containing glucose is withdrawn. The glucose from the interstitial fluid in combination with the patented transport medium, diffuses through the skin to the site of the chemical reaction on the membrane containing the glucose-specific reactants. After about 3–4 minutes, a biochemical equilibrium is reached resulting in an end point color reaction which is measured optically by a highly sensitive reflectance meter.

Examples of varies embodiments of the present invention will now be further illustrated with reference to the following examples.

Unless otherwise stated in a specific example, the targeted skin area and the dry chemistry membranes are treated and prepared, respectively, as follows.

To make the dry glucose chemistry membrane, a 100 ml base preparation is first prepared. This base preparation contains:

about 60 gm Polyvinyl pyrrolidinone K-30 (mw 40,000)
about 1.2 gm Citric Acid Trisodium Salt
about 0.1 gm Citric Acid Monohydrate
about 0.028 gm $NaBH_4$ (sodium Borohidrate)
about 0.1 gm Bovine Serum Albumin (BSA)

The ingredients for the base solutions are dissolved in and thoroughly mixed. Once the base solution is prepared, the following quantities of conditioning flow and stabilizing agents and indicators are added:

| | |
|---|---|
| about 0.546 gm O-Tolidine | adjust pH to about 5.9 to about 6.0 |
| about 2.0 ml | 10% Ganttrez S-95 (10.0 gm/100 ml) is added and pH is adjusted to about 5.9 to about 6.0 with NaOH. |
| about 4.0 gm/L | 75% DOSS [0.533 gm]. |

The conditioning flow agents, stabilizing agent (BSA) and the indicator (O-Tolidine) is dissolved and mixed well into the base preparation. Once the agents and indicator are blended intimately into the base preparation, the specific enzymes for reaction with glucose are added:

| | |
|---|---|
| about 121.0 mg | Glucose Oxidase (60 D) 150 u/ml [150 u* 100 ml/124 u/mg] |
| about 38.53 mg | Horse Radish Peroxidase (POD) 100 u/ml [100 u* 100 ml/259.55 u/mg]. |

The enzymes are added and stirred throughly.

To prepare the membrane, a Biodyne A membrane (0.45 micron pore size), is dipped briefly for about 30 seconds into the prepared enzymatic cocktail until uniformiy wetted. It is then air dried at about 37° C. for about 15 minutes. The dried membrane is stored with desiccant protected from moisture and light. The dried glucose chemistry membrane can be cut into strips of a size about 0.75 inches with an exposed testing area of about 3/16 inches, and the cut strips can be encapsulated or glued within the fold of an adhesive coated mylar, such as Dermaflex PM 500 within a patch configuration such as illustrated in FIG. 3. It is believed that approximately 5 liters of the enzymatic cocktail will effectively treat 200 sq. Ft. of the Biodyne A membrane.

Before conducting the experiments, the targeted skin area and the hands of the user are treated as follows unless specified otherwise.

First, user cleans his/her hands and the targeted skin area thoroughly with deionized water (18 meg ohm). The targeted skin area and hands may be rinsed with the deionized water or wiped with a non-bleached paper towel that has been wetted with the deionized water. The cleansed skin area and hands are then dried with a non-bleached paper towel. User's should avoid the use of bleached paper towels and chlorinated water.

If the targeted skin area is to be pretreated with a skin permeation enhancer, the cleansed and dry targeted skin area is then wiped one or more times with a KimWipe® which is wetted with about 0.5 ml of a selected permeation enhancer. A suitable size KimWipe® for application of the 0.5 ml skin permeation enhancer is dimension at 5×5 cm. While KimWipes® are used, any other ultra clean, lint-free, non-bleached paper towels may be used. KimWipe® are supplied by Kimberly Clarke.

Once the precleansed targeted skin area is treated with a skin permeation enhancer, the pretreated skin is inspected to ensure that there is not excessive skin permeation enhancers on the skin. If too much has been applied, the patch adhesive may not stick. Thus., any excess skin permeation enhancer should first be removed with, for example, a KimWipe®, before applying the patch.

If an organic solvent type skin permeation enhancer is selected, such as isopropyl alcohol or ethyl acetate, it is preferable to allow the organic solvent to first dry or evaporate before applying te patch to the treated skin area to avoid potential negative interaction between the organic solvent type skin permeation enhancer and the chemical reagents on the membrane. If the skin permeation enhancer selected is not an organic solvent, the patch may be applied immediately following treatment of the skin area with such skin permeation enhancer.

Before the patch is applied, it is removed from its foil envelopes with 1 gram of desiccant. Following removal, the selected transfer medium or gel is loaded into the hole in the bottom of the patch to uniformly and continuously wet the membrane. Once the membrane is wetted with the gel, the test should be conducted by within 5 to 10 minutes thereafter. Also, wetted membrane should not be exposed to bright lights.

Once the patch is positioned on the targeted skin area, it is left thereafter about 5 minutes, at which time the color change is read by a reflectometer to detect the present of glucose.

Also, unless otherwise specified, the wet chemistry gel utilized is about 1% carboxy methylcellulose.

EXAMPLE 1

The following two figures represent data obtained with a glucose patch in accordance with the present invention. The glucose membrane is prepared similar to that described immediately above.

Figure 11:
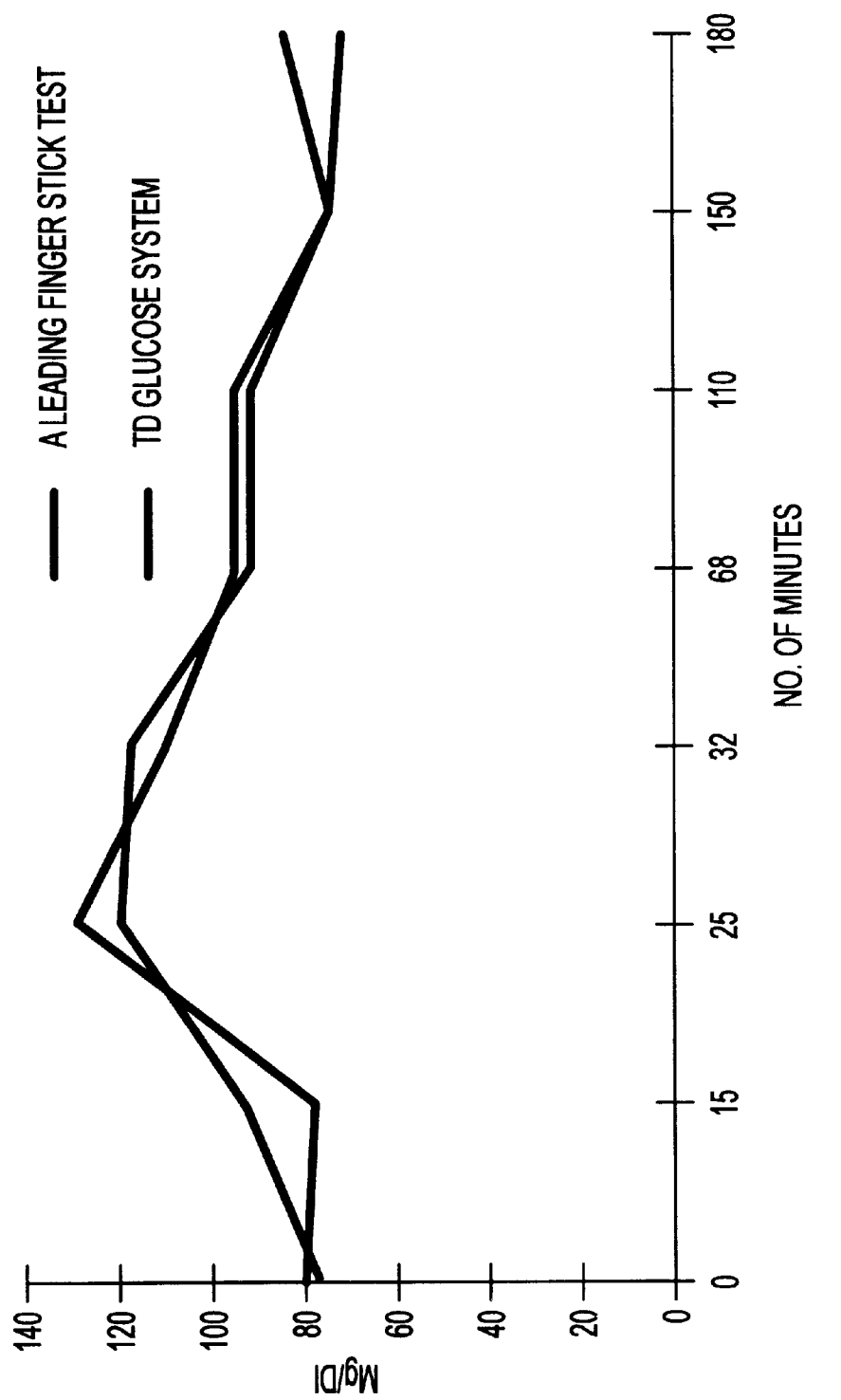
FIG. 11 is a plot of data of an oral glucose tolerance test comparing the results obtained from a noninvasive transdermal patch of the present invention with the results obtained from capillary blood glucose using the APG method.

FIG. 11 shows results of a glucose tolerance test performed on a non-diabetic subject over a three hour period. These results in Figure II show a high correlation between the glucose patch and a current popular finger stick method. In this example, the wipe is propylene glycol.

EXAMPLE 2

Figure 12:
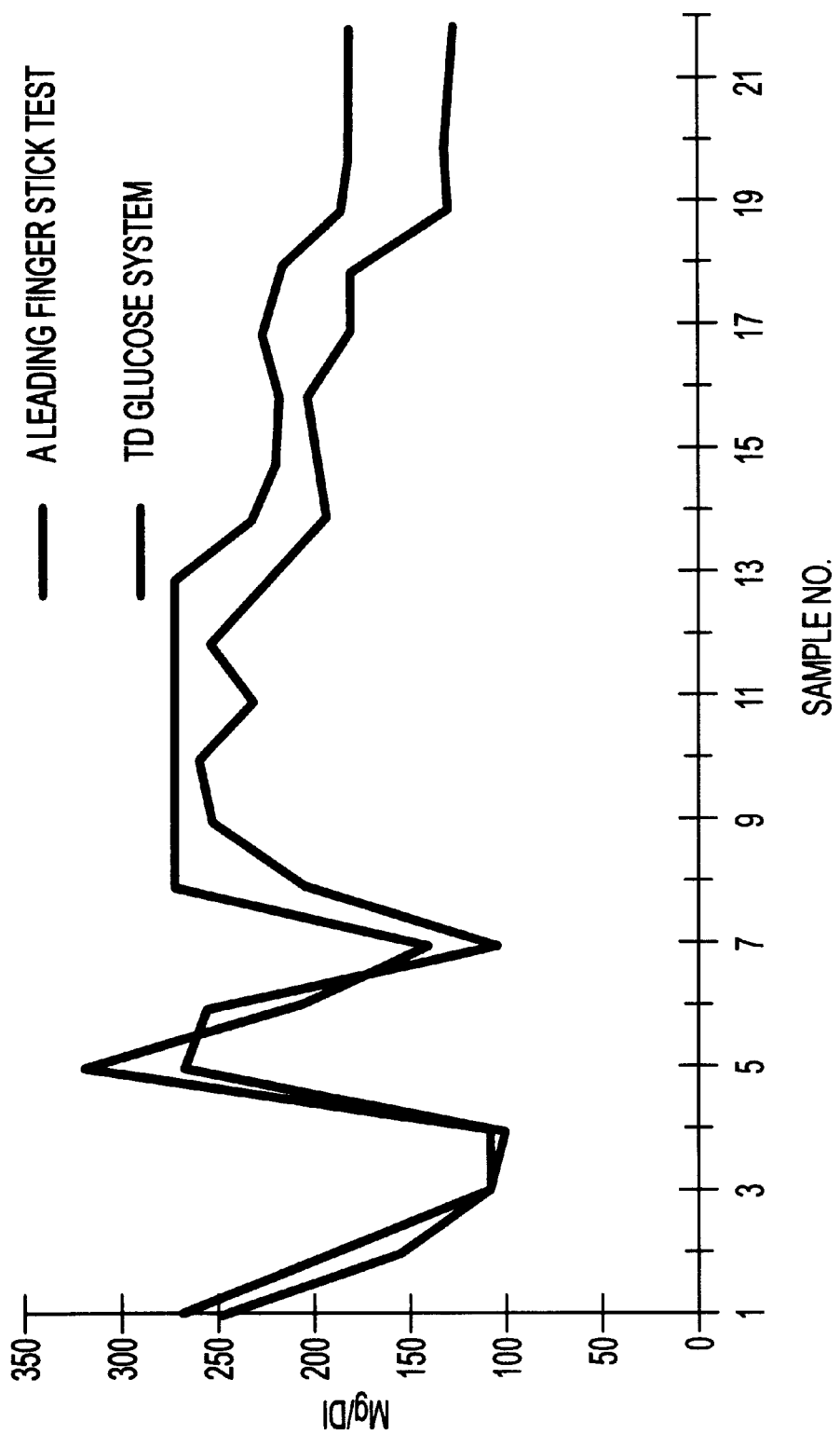
FIG. 12 is a plot of data of an oral glucose tolerance test comparing the results obtained from a noninvasive transdermal patch of the present invention with the results obtained from capillary blood glucose using the APG method.

FIG. 12 shows the results of a series of tests that are performed on a Type I insulin dependent diabetic over a 21 day period. One sample is taken per day in a random manner—with no control over the sampling time of day or relation to the patient's insulin .

EXAMPLE 3

Figure 13:
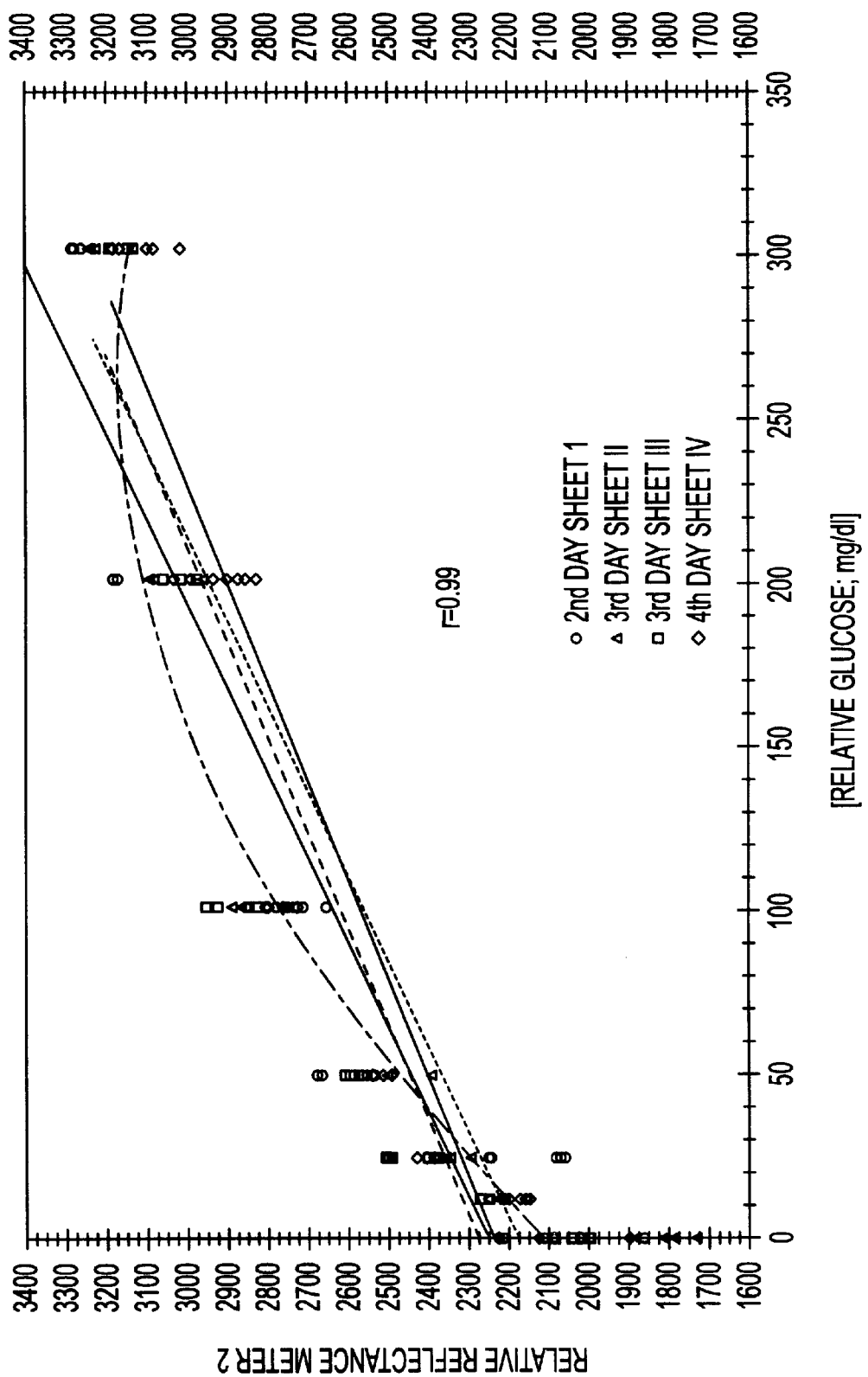
FIG. 13 is a plot of data of the results of testing linearity of glucose patch reaction chemistry in glucose patches of the present invention when increasing concentrations of glucose.

FIG. 13 depicts data from a series of experiments testing the linearity of the glucose patch reaction chemistry to increasing concentrations of glucose. Four glucose determinations are performed daily on a series of standards and the results correlated after four days of tests. These results show that the detection membrane is capable of measuring the minute amounts of glucose.

Figure 14:
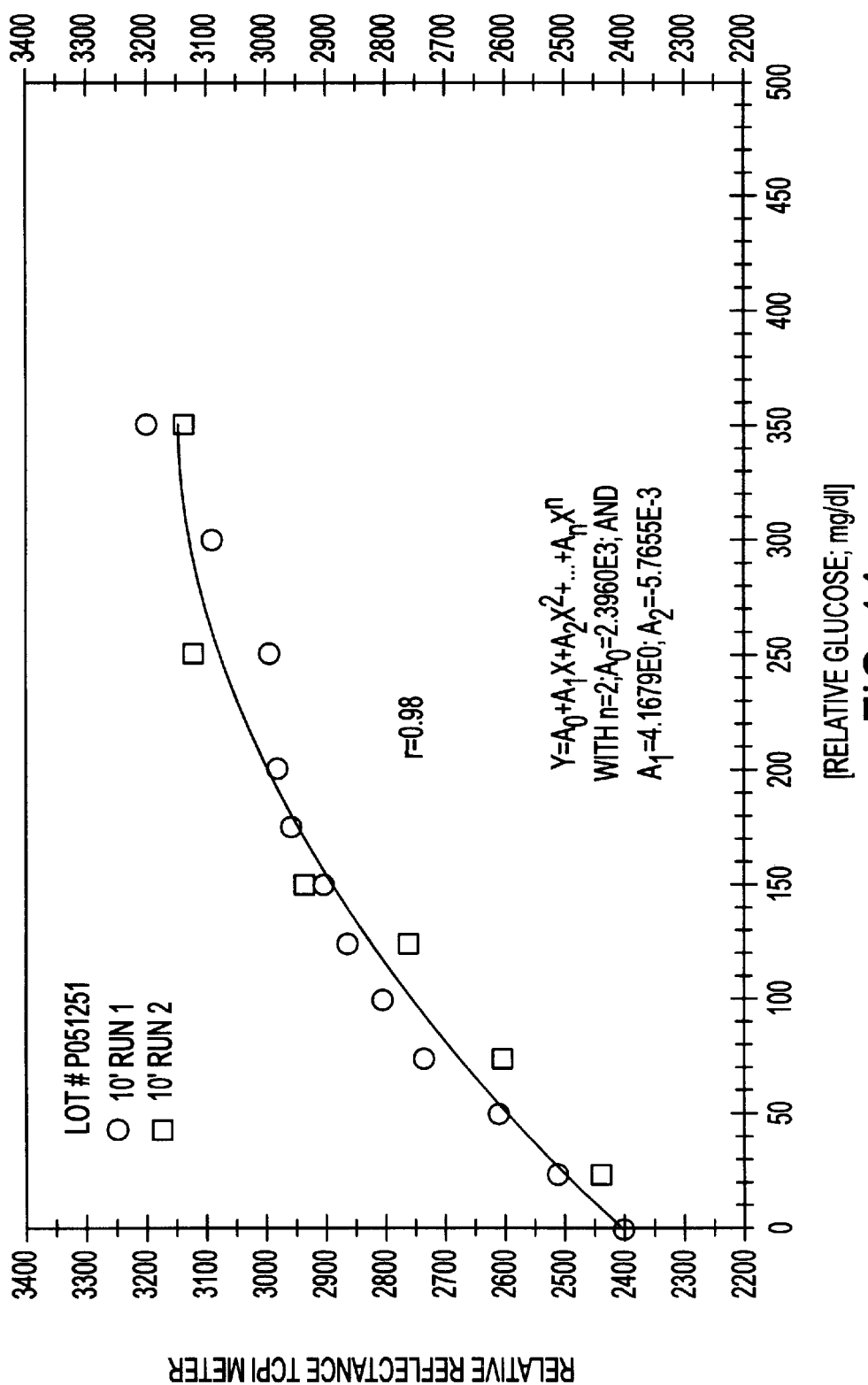
FIG. 14 is a graph of data depicting an actual calibration curve for a noninvasive transdermal glucose patch of the present invention.
Figure 16A:
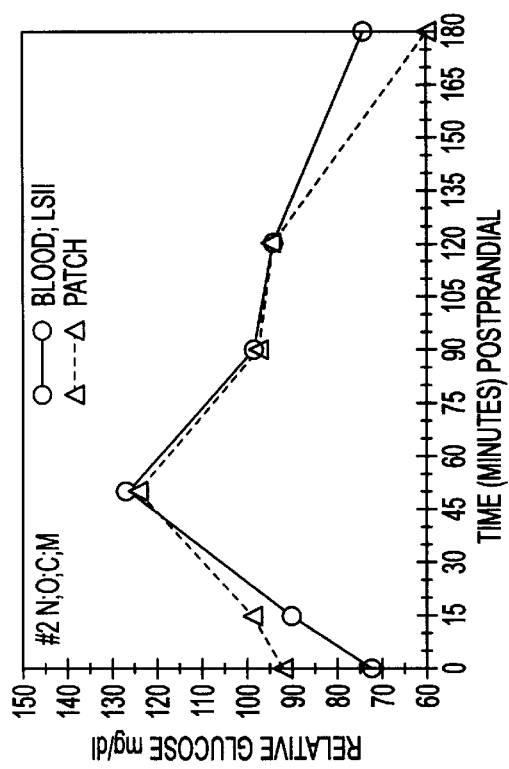
FIG. 16 illustrates plots of data which compares the results obtained from a noninvasive transdermal patch of the present invention with results obtained from capillary blood glucose utilizing standard LSII method.
Figure 16B:
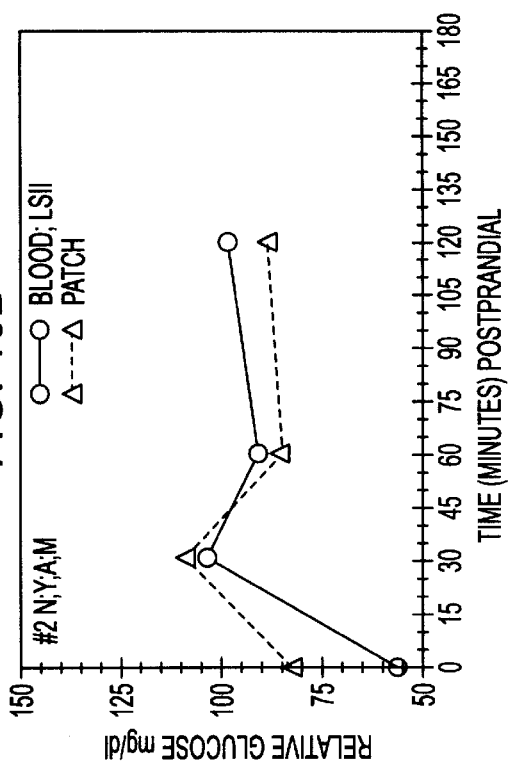
Figure 16C:
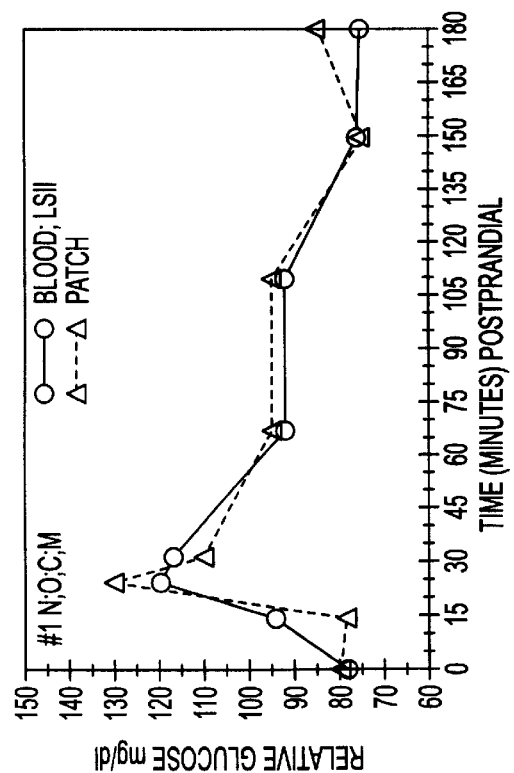
Figure 16D:
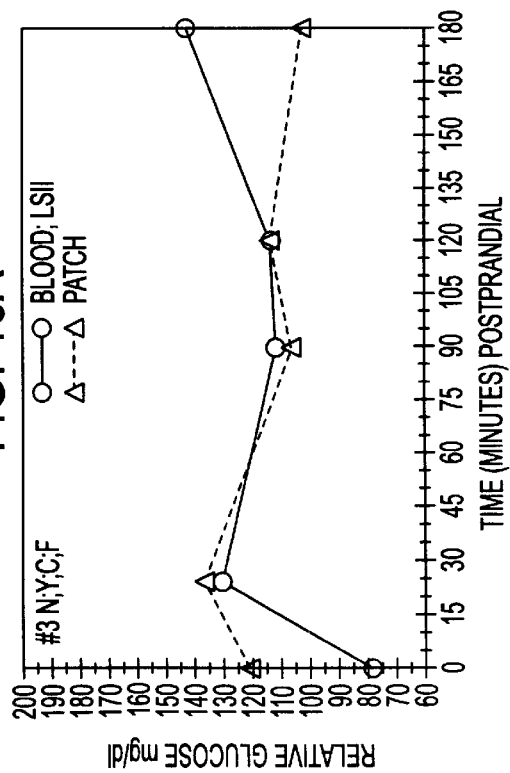
Figure 17A:
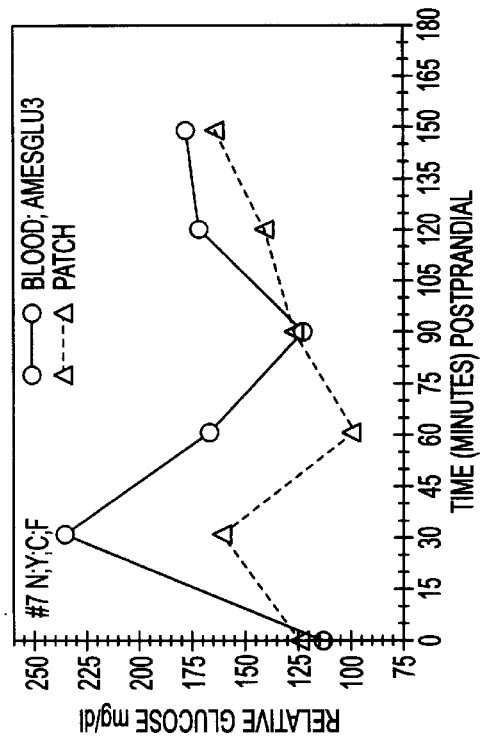
FIG. 17 illustrates plots of data which compares the results obtained from a noninvasive transdermal patch of the present invention with results obtained from capillary blood glucose utilizing standard LSII method.
Figure 17B:
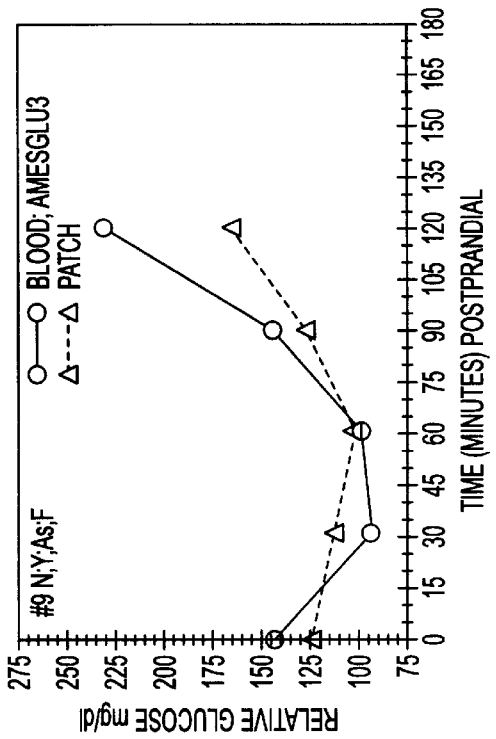
Figure 17C:
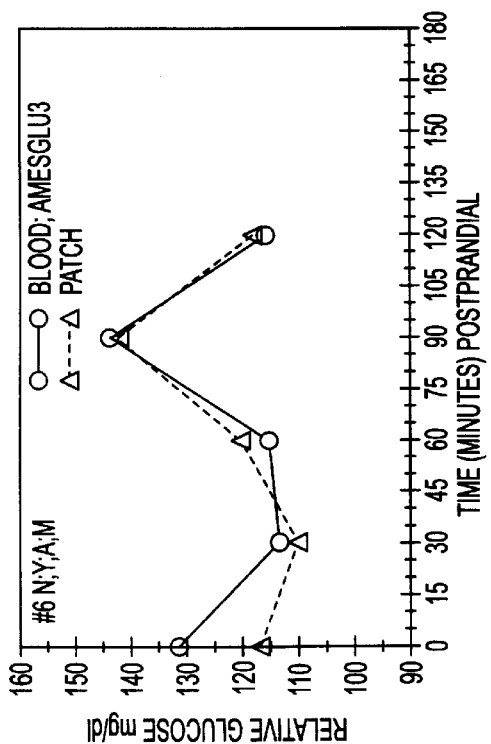
Figure 17D:
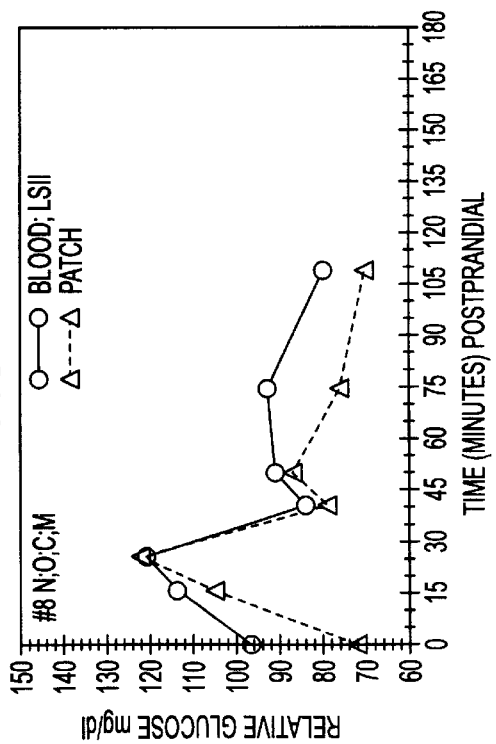

FIG. 14 depicts an actual calibration curve for the glucose patch. The data is depicted in FIG. 15A. A set of these glucose patches are evaluated with calibration standards using nine patches for each standard. The coefficient of variation averaged less than 4% with n r-value of 0.99 for the standard curve after 5 minutes of reaction time.

EXAMPLE 4

The following is data resulting from oral glucose tolerance tests of volunteers. The tests are designed to compare the results obtained with the glucose patch to a "state of the art" capillary blood glucose method from other companies. The patch reflectance data is obtained using a reflectometer as described herein. These people have not eaten for twelve hours prior to the tests. After initial glucose determinations, they drank a solution of 100 grams of glucose within five minutes. The comparative tests are continued over the course of 1.5–3 hours. Note that the capillary blood glucose values rise to a peak level by 30–50 minutes and then return to "normal", as is expected with nondiabetics. The patch reflectance values parallel the capillary blood glucose values and are much easier to obtain.

All blood results are obtained using an FDA "accepted" standard finger stick capillary blood glucose method with the manufacturers electronic meter indicated for each test and strips by the recommended procedure.

Patient 1 is a normal person (older Caucasian male) who is tested at fasting level through postprandial 100 grams glucose for three hours:

| Time (min.) Postprandial | Blood Glucose Life Scan II mg/dl | Patch Glucose TCPI mg/dl |
| --- | --- | --- |
| 0 | 78 | 80 |
| 15 | 94 | 78 |
| 25 | 120 | 130 |
| 32 | 117 | 110 |
| 68 | 92 | 95 |
| 110 | 92 | 95 |
| 150 | 76 | 75 |
| 180 | 73 | 85 |

Patient 2 is a normal (older Caucasian male) person who is tested at fasting level through postprandial 100 grams glucose for three hours:

| Time (min.) Postprandial | Blood Glucose Life Scan II mg/dl | Patch Glucose TCPI mg/dl |
| --- | --- | --- |
| 0 | 73 | 92 |
| 15 | 91 | 99 |
| 50 | 128 | 125 |
| 90 | 99 | 98 |
| 120 | 95 | 95 |
| 180 | 75 | 60 |

Patient 3 is a normal person (young Caucasian female) who is tested after breakfast through lunch, moderate exercise, and a snack, for three hours:

| Time (min.) Postprandial | Blood Glucose Life Scan II mg/dl | Patch Glucose TCPI mg/dl |
| --- | --- | --- |
| 0 | 77 | 120 |
| 24 | 130 | 136 |
| 90 | 111 | 106 |
| 120 | 113 | 113 |
| 180 | 143 | 102 |

Patient 4 is a normal person (young African American male) who is tested fasted for two hours.

| Time (min.) Postprandial | Blood Glucose Life Scan II mg/dl | Patch Glucose TCPI mg/dl |
|---|---|---|
| 0 | 55 | 81 |
| 30 | 103 | 108 |
| 60 | 90 | 85 |
| 120 | 98 | 88 |

Patient 5 is a type I diabetic patient (older Caucasian male) who is tested on twenty two occasions by several different extraction formulations:

| Time (min.) Postprandial | Blood Glucose Life Scan II mg/dl | Patch Glucose TCPI mg/dl |
|---|---|---|
| 1 | 268 | 247 |
| 2 | 196 | 157 |
| 3 | 109 | 110 |
| 4 | 108 | 101 |
| 5 | 314 | 265 |
| 6 | 207 | 251 |
| 7 | 140 | 106 |
| 8 | 267 | 203 |
| 9 | 367 | 248 |
| 10 | 267 | 256 |
| 11 | 267 | 228 |
| 12 | 267 | 251 |
| 13 | 267 | 218 |
| 14 | 227 | 190 |
| 15 | 216 | 196 |
| 16 | 213 | 200 |
| 17 | 222 | 180 |
| 18 | 214 | 181 |
| 19 | 183 | 127 |
| 20 | 179 | 130 |
| 21 | 180 | 127 |
| 22 | 178 | 125 |

Patient 6 is a normal person (young African American male) who is tested over the course of two hours.

| Time (min.) Postprandial | Blood Glucose Life Scan II mg/dl | Patch Glucose TCPI mg/dl |
|---|---|---|
| 0 | 132 | 116 |
| 30 | 113 | 110 |
| 60 | 115 | 120 |
| 90 | 144 | 142 |
| 120 | 116 | 118 |

Patient 7 is a normal person (young Caucasian female) who is tested after breakfast through lunch, moderate exercise, and a snack, for two and ½ hours:

| Time (min.) Postprandial | Blood Glucose Life Scan II mg/dl | Patch Glucose TCPI mg/dl |
|---|---|---|
| 0 | 111 | 120 |
| 30 | 237 | 160 |
| 60 | 167 | 98 |
| 90 | 121 | 125 |
| 120 | 173 | 140 |
| 150 | 180 | 165 |

Patient 8 is a normal person (older Caucasian male) who is tested after fasting level through postprandial 100 grams glucose for two hours:

| Time (min.) Postprandial | Blood Glucose Life Scan II mg/dl | Patch Glucose TCPI mg/dl |
|---|---|---|
| 0 | 95 | 70 |
| 15 | 113 | 104 |
| 25 | 120 | 122 |
| 40 | 83 | 78 |
| 50 | 90 | 86 |
| 75 | 92 | 75 |
| 110 | 79 | 69 |

Patient 9 is a normal person (young Asian female) who is tested after breakfast through lunch, and a snack, for two hours:

| Time (min.) Postprandial | Blood Glucose Life Scan II mg/dl | Patch Glucose TCPI mg/dl |
|---|---|---|
| 0 | 141 | 120 |
| 30 | 91 | 110 |
| 60 | 97 | 100 |
| 90 | 144 | 126 |
| 120 | 233 | 165 |

Patient 10 is a normal person (young Caucasian male) who is tested after breakfast then glucose load for two hours:

| Time (min.) Postprandial | Blood Glucose Life Scan II mg/dl | Patch Glucose TCPI mg/dl |
|---|---|---|
| 0 | 89 | 105 |
| 30 | 125 | 123 |
| 60 | 97 | 105 |
| 120 | 105 | 120 |

Figure 18A:
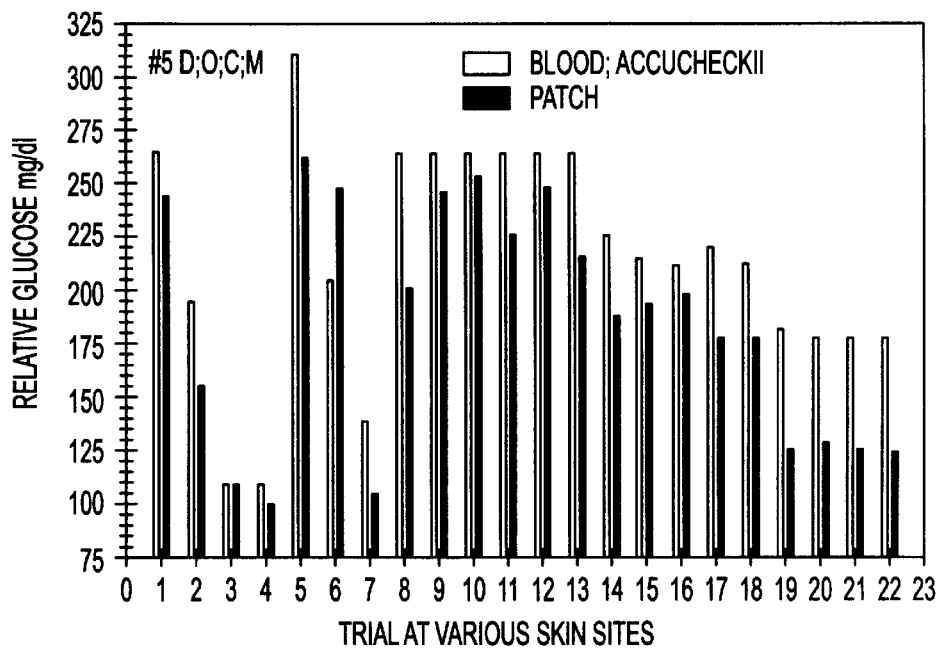
FIG. 18 illustrates plots of data which compares the results of a noninvasive transdermal patch of the present invention with the results obtained from capillary blood glucose utilizing standard LSII method.
Figure 18B:
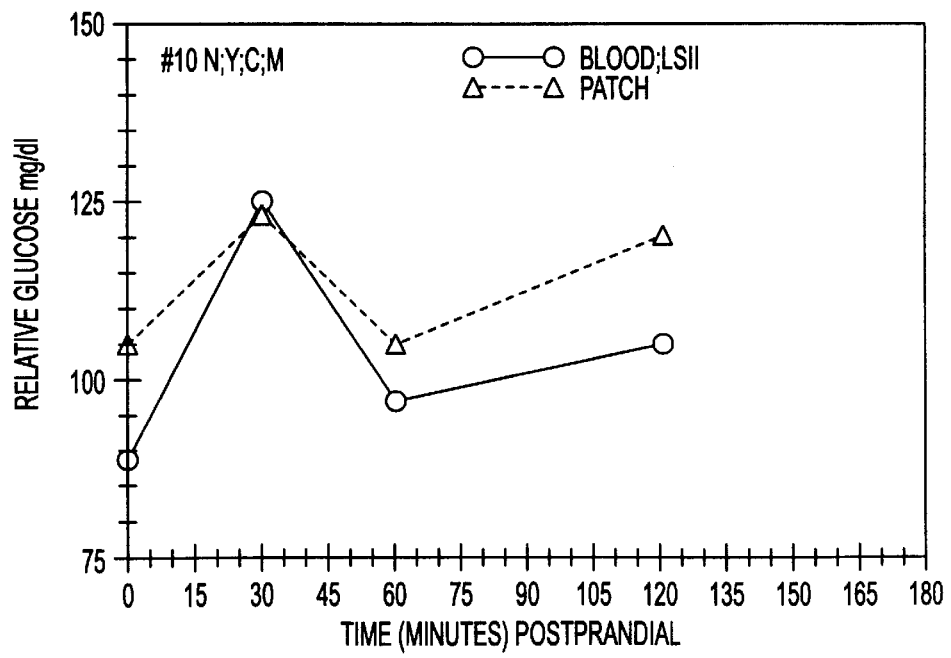

PATIENT KEYS
N = Normal
D = DIABETIC TYPE 1;
O = OLDER
= MIDDLE AGE (NONE TESTED)
Y = YOUNGER
C = CAUCASIAN
A = AFRICAN AMERICAN
AS = ASIAN
M = MALE
F = FEMALE The results of the comparison of a standard finger stick method with glucose patch subjects undergoing glucose tolerance tests are depicted in FIGS. 16, 17 and 18. One type I diabetic subject (#5) is included. For comparison, two different "NO WIPE" finger stick method are also used.

Subject #9 (see FIG. 11) engages in some extensive manual labor between testing,, and as depicted, despite the glucose load she receives, her glucose level decreases. She also begins the glucose tolerance test late and eats lunch before the end of the test period.

Subject 5 (See FIG. 18, top graph) is a diabetic subject who subsequently performs 22 assays at various skin sites. Instead of receiving a glucose load as with the other 9 patients, this diabetic delays insulin administration then tests both before and after insulin for two separate, four test periods. Comparison #8–22 in FIG. 18, top graph, reflect one series of tests a day consisting of 6 simultaneous patches using different skin sites, which are performed before administering insulin, and which are followed by 5 simultaneous patches on the same sites which are performed later in the day after eating, but before diabetic's injection and finally 4 simultaneous patches at different sites after giving sufficient time for the insulin to lower the diabetic's glucose levels.

EXAMPLE 5

Figure 19:
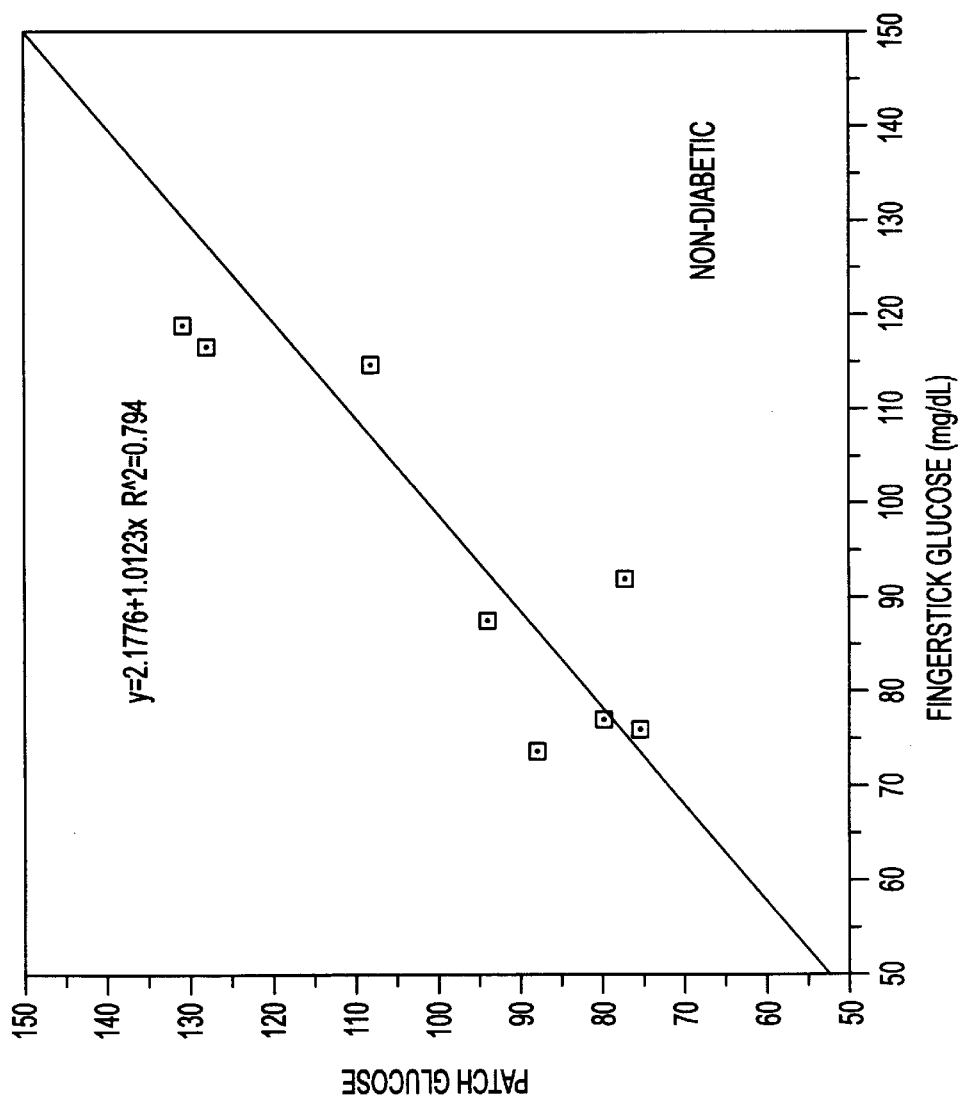
FIG. 19 is a plot of data which shows the correlation of results between a noninvasive transdermal patch of the present invention with results obtained from capillary blood glucose utilizing a standard method.

FIG. 19 illustrates the results of the comparison of blood glucose levels in eight (8) non-diabetics using patches vs. finger stick. It confirms that the correlation between finger stick tests and plasma glucose in the range of from $r^2=0.53-0.93$ comparing different finger stick tests using both name brand and generic strips.

EXAMPLE 6

Figure 20:
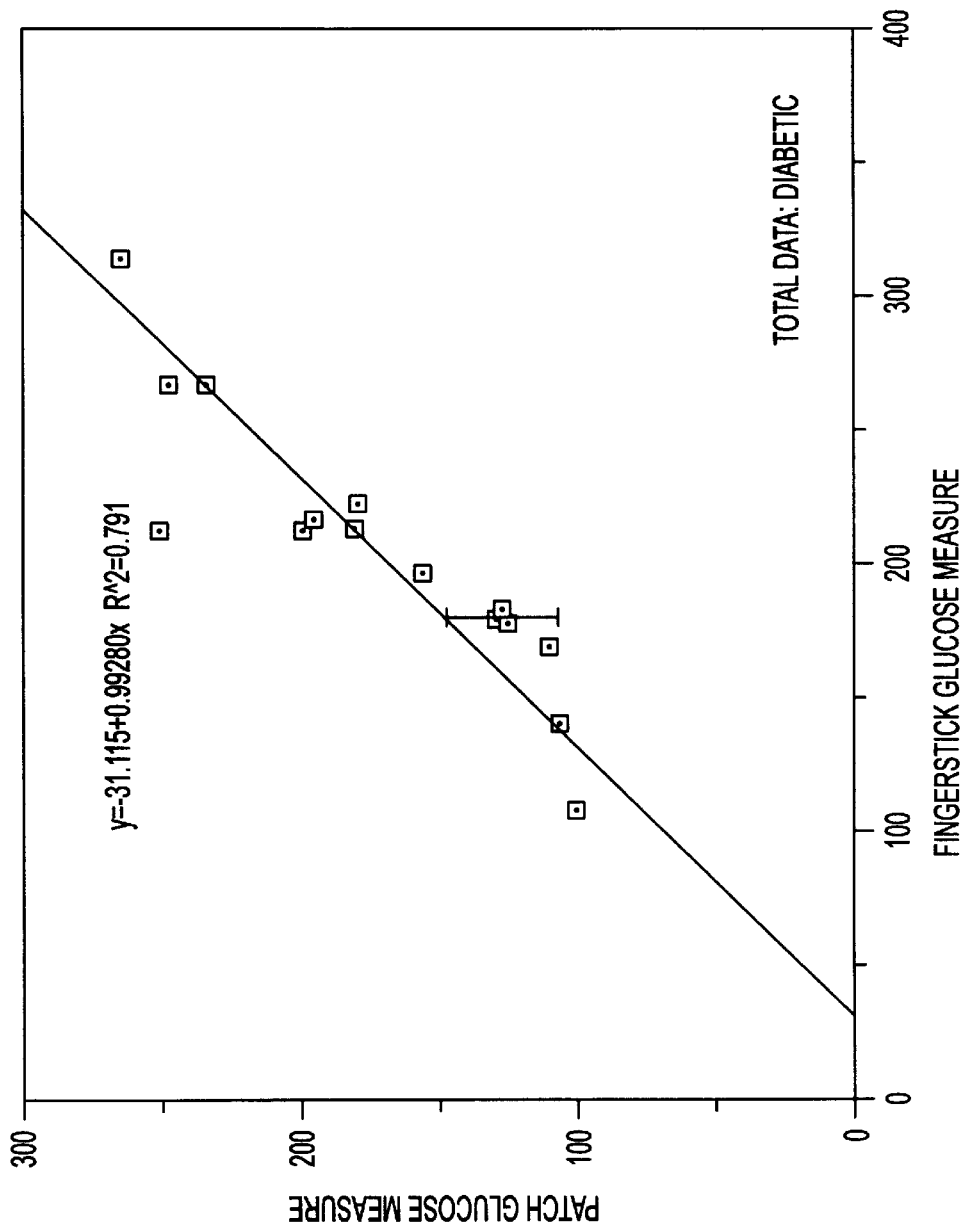
FIG. 20 is a plot of data which shows the correlation of results obtained from a noninvasive transdermal patch of the present invention with results obtained from capillary blood glucose utilizing a standard method.
Figure 21:
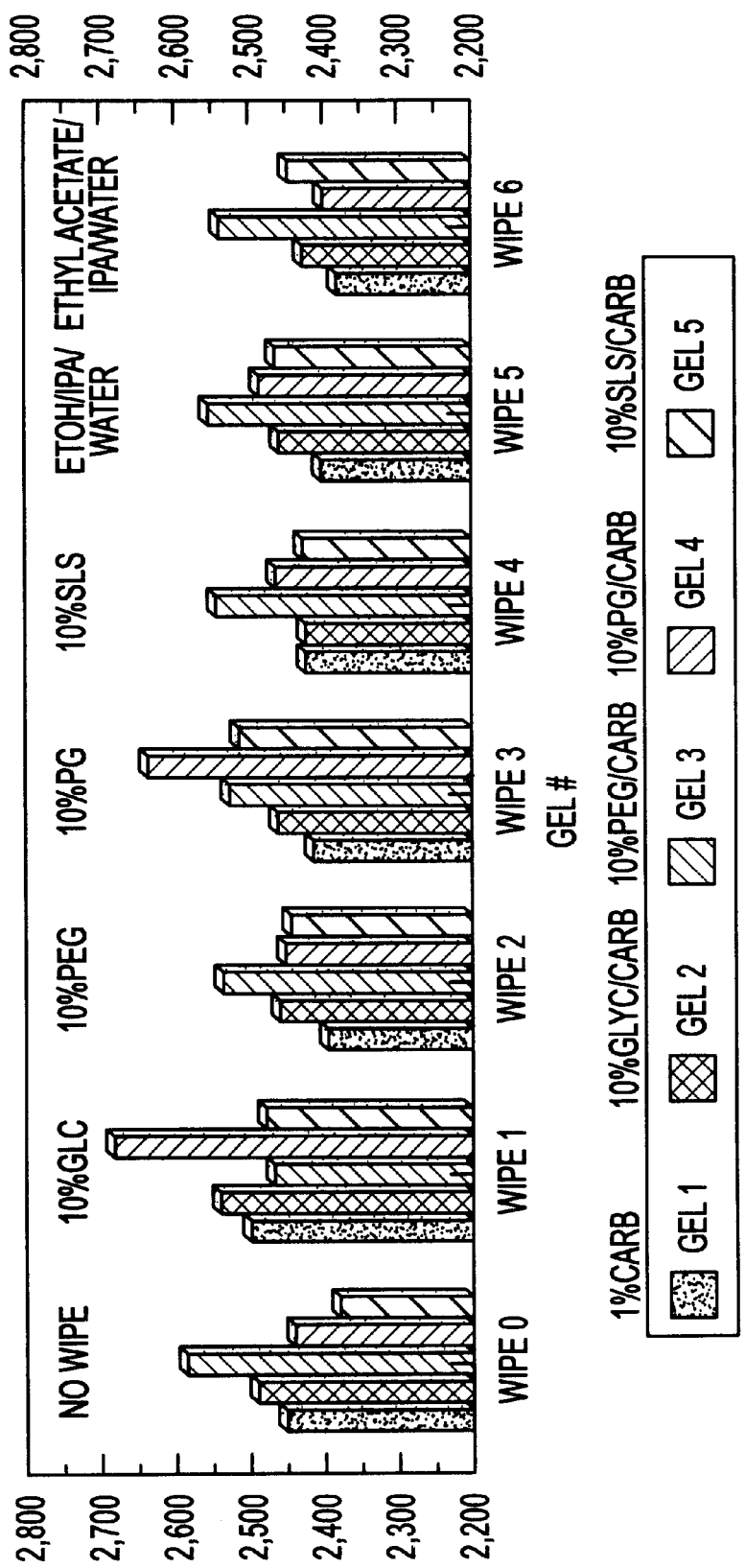
FIG. 21 is a bar graph of data which shows the results obtained from noninvasive transdermal patches of the present invention constructed with different gels which are tested with different wipes.
Figure 22:
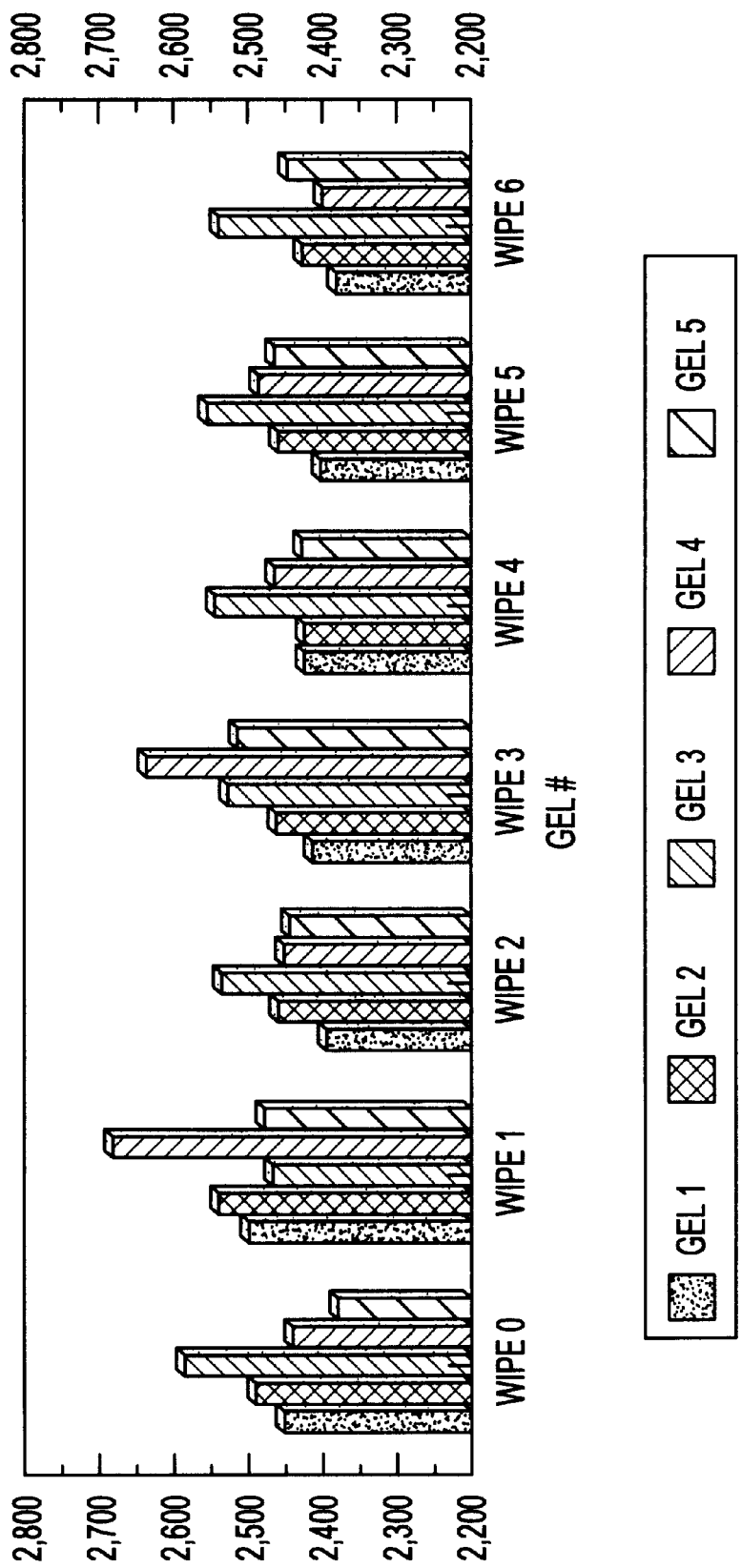
FIG. 22 is a bar graph of data which shows the results obtained from noninvasive transdermal patches of the present invention constructed with different gels which are tested with different wipes.
Figure 23:
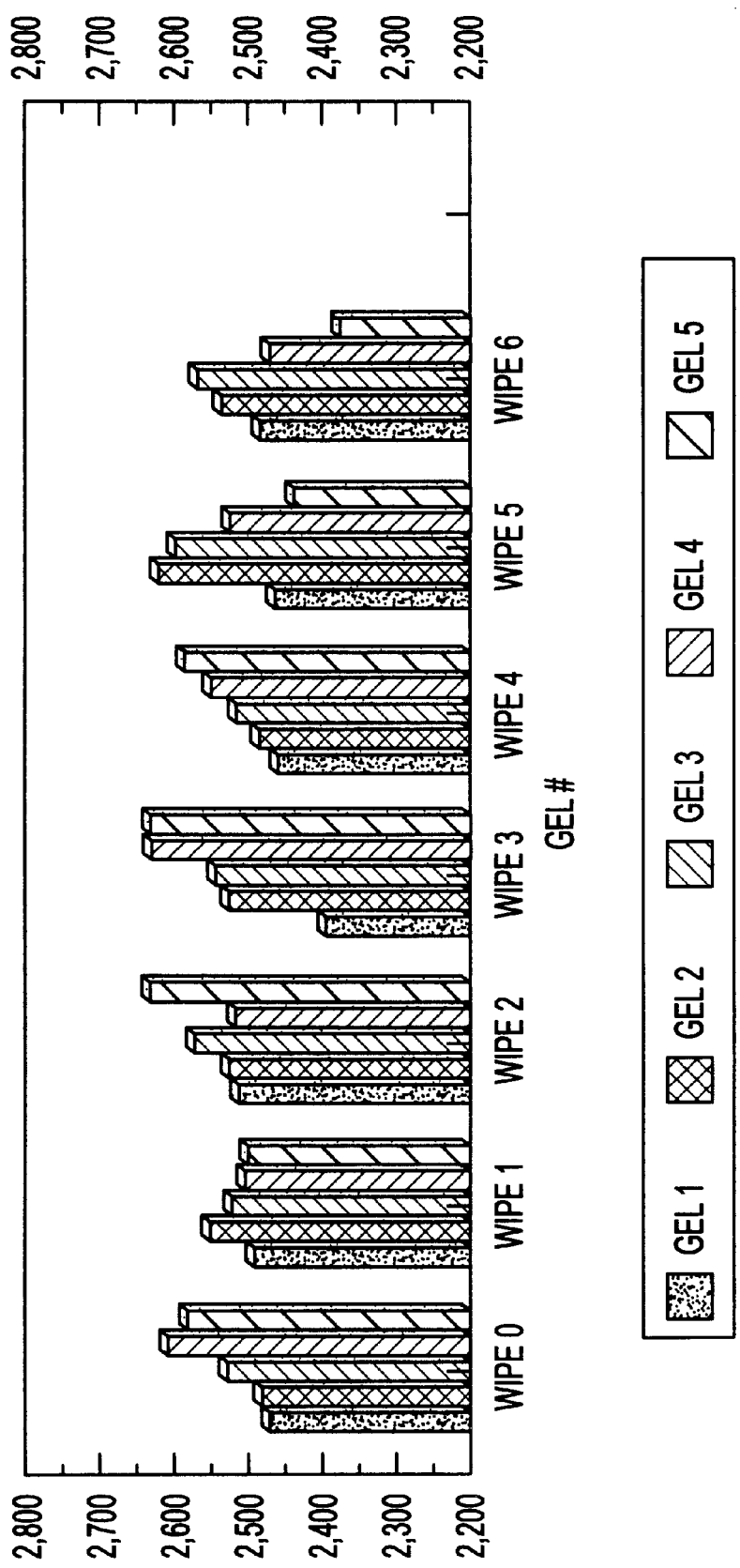
FIG. 23 is a bar graph of data which shows the results obtained from noninvasive transdermal patches of the present invention constructed with different gels which are tested with different wipes.
Figure 24:
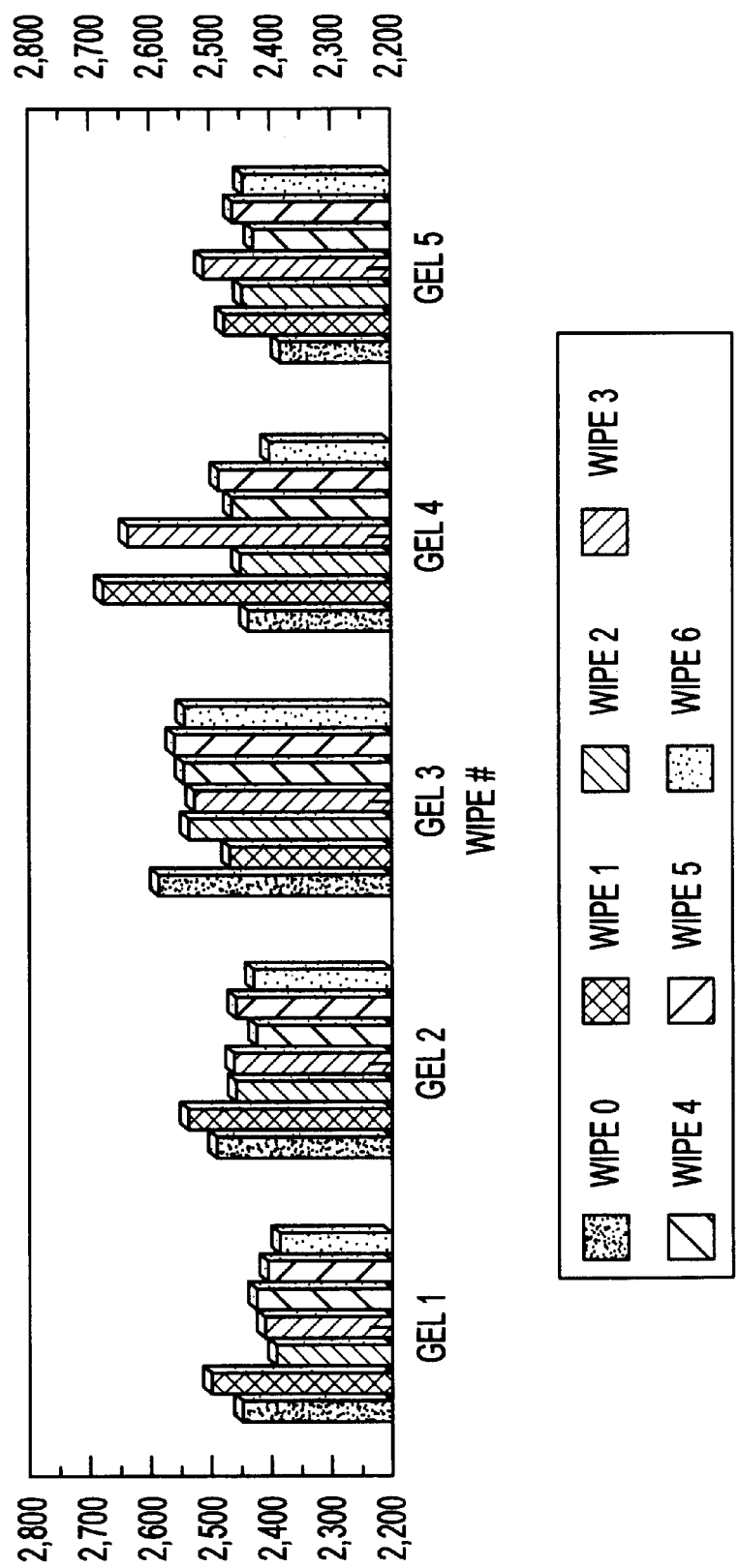
FIG. 24 is a bar graph of data which shows the results obtained from noninvasive transdermal patches of the present invention constructed with different gels which are tested with different wipes.
Figure 25:
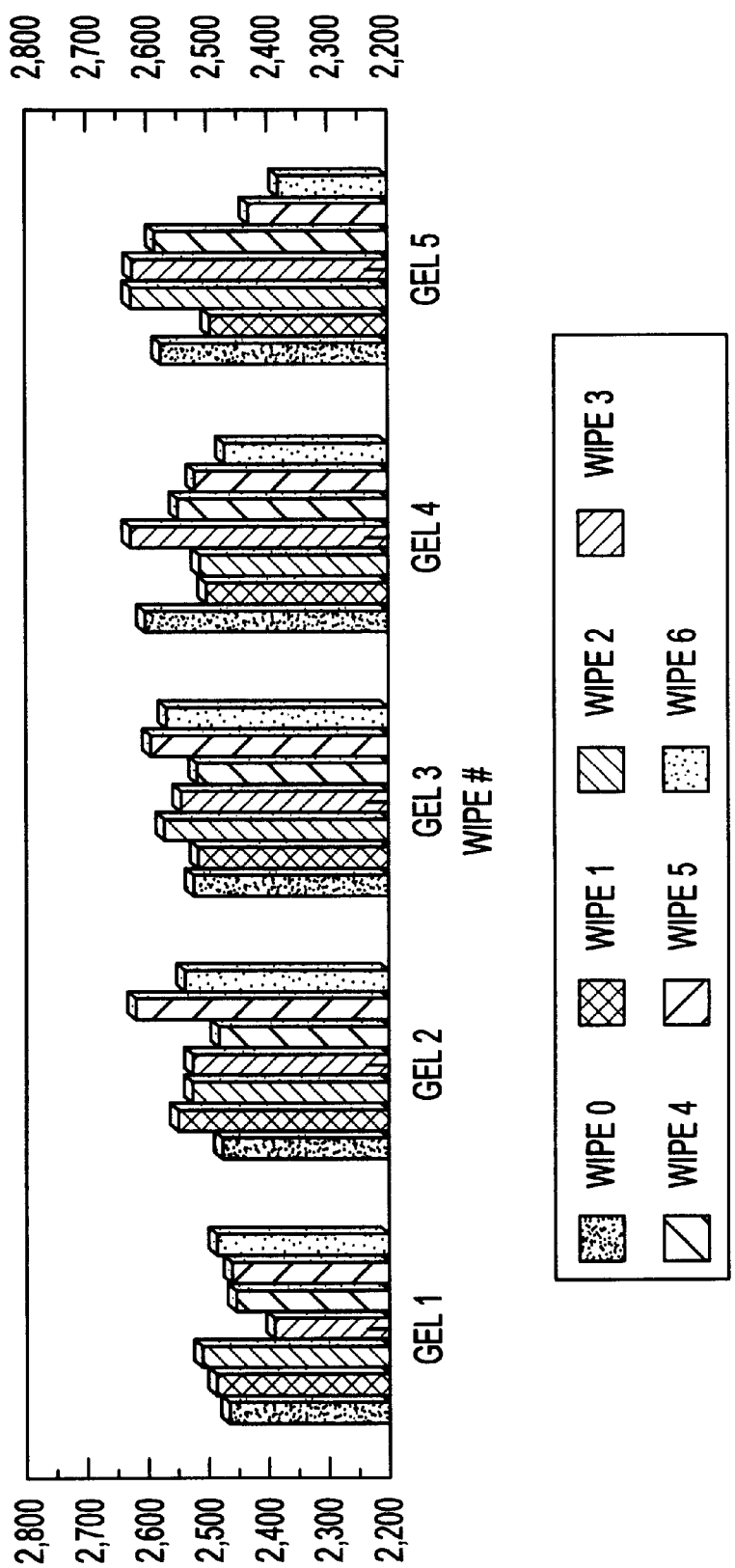
FIG. 25 is a bar graph of data which shows the results obtained from noninvasive transdermal patches of the present invention constructed with different gels which are tested with different wipes.

A similar series of experiments are performed with a diabetic subject (See FIG. 20). FIG. 20 shows that the patch and finger stick blood glucose levels correlate in a highly significant fashion with a coefficient of determination $r^2=0.791$ and significant level of $p=0.001$. These results are obtained on one subject over several months. This data demonstrates good correlation over a glucose range of 100–300 mg/dl. There are no changes in diabetic therapy or insulin dosages throughout the testing period.

EXAMPLE 7

Two individuals, MM and JM, volunteered to test 5 different gels and 6 different wipes in combination with a super sensitive or conditioned glucose membrane in accordance with the present invention.

Prototype glucose membranes are made as described earlier herein with respect to the alternative glucose reactive membrane.

The glucose patch, into which the glucose membrane was placed, is similar to the patch depicted in FIG. 3.

Gels

The five gels are as follows:
1. About 1% carbopol in deionized water;
2. About 10% glycerin and about 1% carbopol in deionized water;
3. About 10% polyethylene glycol and about 1% carbopol in deionized water;
4. About 10% propylene glycol and about 1% carbopol in deionized water
5. About 10% sodium lauryl sulfate and about 1% carbopol.

The gels are made by simply mixing the components together thoroughly as described herein.

Wipes

The six wipes are as follows:
1. About 10% glycerin in deionized water;
2. About 10% polyethylene glycol in deionized water (18 meg ohm);
3. About 10% propylene glycol in deionized water (18 meg ohm);
4. About 10% sodium lauryl sulfate in deionized water (18 meg ohm);
5. 1:1:1 ethyl alcohol:isopropyl alcohol:deionized water
6. 1:1:1 ethyl acetate:isopropyl alcohol:deionized water (18 meg ohm).

The wipes are made as follows: mixed and thoroughly stirred and stored in an amber bottle with a teflon lined cap to minimize contamination and evaporation.

Each individual's blood glucose is determined by LSII method at the time of testing. MM's blood glucose measured as 96 mg/dl, and JM's blood glucose is 100 mg/dl. In detailing the reflectance from the glucose patches, a reflectometer having the specification described herein is used.

In carrying out the procedure, each individual's targeted skin area, to which the patch is applied, is first thoroughly cleansed by wiping with deionized water. Following cleansing, in one test the five different gels glucose patches are applied directly to the cleansed skin area without first wiping with a wipe. In all other tests, the cleansed skin area is first pretreated with one of the six wipes. In pre-treating the skin area, a liberal amount of a wipe is applied by a Chem Wipe™. If too much is applied, the excess amount is removed with a dry Chem Wipe™.

The five different gel glucose patches are then applied to the wiped skin area within ten seconds after wiping. Before applying the gel to the cleansed skin area, the dry chemical glucose membrane is brought into continuous contact with the gel to uniformly wet the dry chemical glucose membrane. The patch is in contact with the cleansed skin area for about 5 minutes, at which time the color change of the membrane is read by reflectance by the meter to detect the glucose in the interstitial fluid of MM and JM. The reflectance values for MM and JM with respect to each gel and wipe are recited in the bar graphs depicted in FIGS. 21, 22, 23, 24, and 25 on the following tables, respectively. The numbers for the gels and wipes designated herein correspond to the numbers in FIGS. 21, 22, 23, 24 and 25.

| WIPE/GEL | 1 | 2 | 3 | 4 | 5 | 6 | 7 |
|---|---|---|---|---|---|---|---|
| | | | MM | | | | |
| 1 | 2504 | 2399 | 2415 | 2428 | 2411 | 2388 | 2456 |
| 2 | 2542 | 2463 | 2465 | 2428 | 2463 | 2433 | 2494 |
| 3 | 2471 | 2542 | 2529 | 2549 | 2561 | 2545 | 2590 |
| 4 | 2684 | 2454 | 2640 | 2467 | 2493 | 2405 | 2443 |
| 5 | 2480 | 2449 | 2516 | 2431 | 2468 | 2452 | 2385 |
| | | | JM | | | | |
| 1 | 2495 | 2519 | 2398 | 2463 | 2468 | 2481 | 2478 |
| 2 | 2557 | 2532 | 2532 | 2488 | 2628 | 2545 | 2486 |
| 3 | 2526 | 2578 | 2551 | 2525 | 2604 | 2578 | 2532 |
| 4 | 2507 | 2520 | 2635 | 2556 | 2528 | 2478 | 2613 |
| 5 | 2502 | 2636 | 2633 | 2593 | 2438 | 2386 | 2585 |

EXAMPLE 8

The following skin permeation enhancers are tested for permeation enhancing power. The skin is first wiped with a pad wetted with one of the following permeation enhancer formulations. A glass cylinder is then secured by o-ring seal against the wiped area of skin and a defined volume of distilled water is added to the inside of the glass cylinder (see FIG. 26). After five minutes of water contact with the skin, the water is removed and its glucose concentration analyzed by High Performance Liquid Chromatography with a Bioanalytical Systems, Inc. Enzymatic detector system. The ratio of glucose detected relative to the amount detected using a distilled water wipe (control) is used to evaluate the permeation enhancing power of each formulation. HPLC results are as follows:

| | Skin Permeation Enhancer | Ratio to Water Results |
|---|---|---|
| 1) | 20% Salicylic Acid in 50:50-Isopropyl Alcohol:Deionized Water | 7.02 → 10.9 |
| 2) | Tween 80 | 3.5 → 6.5 |
| 3) | Limonane | 1 → 5.7 |
| 4) | Isopropyl Alcohol | 1.1 → 1.8 |
| 5) | Acetone | 1.1 → 1.8 |
| 6) | 1:1:1-Ethyl Acetone:Isopropyl Alcohol:Water | 1 → 2.3 |
| 7) | 90:5:5-Isopropyl Alcohol:Tween 80:Limonene | 1.7 → 8 |
| 8) | 10% Lactic Acid in Isopropyl Alcohol | 4 → 11 |
| 9) | 90% Lactic Acid and 10% Tween 80 | 7 → 16 |

In parallel with the chromatographic studies of Example 7, a certain permeation enhancer formulation is evaluated by auditioning it as a prewipe in conjunction with actual glucose monitoring patches. The performance of a certain permeation enhancer formulation is evaluated by comparing to the results obtained with a distilled water prewipe. The formulation gave reproducible results in replicate determinations, as shown in FIG. 27.

EXAMPLE 9

Next, patient results obtained with various transdermal patches are compared to those obtained using a commercial fingerstick blood glucose monitor. Oral glucose tolerance tests are performed (i.e., baseline readings are performed on fasting volunteers who drank 50–75 grams of glucose and who are then retested periodically over the course of three hours). Both the baseline and the subsequent measurements are made with the glucose patch and with a commercial fingerstick blood glucose system. (See FIG. 28) The glucose patch gels in this experiment are 1% Carbopol® and 10% propylene glycol in deionized water (18 meg ohm).

EXAMPLE 10

Once the glucose from the interstitial fluid diffuses into the patch matrix material, it is quantitated enzymatically using glucose oxidase and peroxidase on preferably, a polyethersulphone membrane. The colored product of the peroxidase reaction, o-tolidine, is then measured by optical reflectometry. This measurement may be performed either kinetically by measuring the change in optical density at timed intervals, or else may be determined at a single fixed-time endpoint of five minutes. The latter method is the one utilized herein. The enzyme cascade and color development system is well-characterized herein. This chemistry system gives accurate and reproducible results when evaluated either by eye or by reflectometry, and the stability is shown to exceed one year. Reproducible slopes are obtained for standard curves, indicated that stored calibrations may be used to convert photometer millivolt readings into glucose concentrations expressed as mg/dl. The sensitivity of the device appears to be approximately 20 mcg/dl or 1 mcg/5 ml or 0.005 mcg/25 mcl, as shown in FIG. 29.

The glucose concentrations tested and shown in FIG. 29 are prepared as follows. A stock glucose solution of 1000 mg/dl is first prepared, as illustrated in FIG. 29. A sample of this stock solution is then diluted in $dH_2O$ (18 meg ohm) to achieve a desired glucose concentration. Each glucose concentration made is tested and illustrated in FIG. 29. The individual glucose concentrations are then diluted 1:50 in a 1% carboxy polymethylene and 10% propylene gel of the present invention for testing. According to FIG. 29, the sensitivity of the glucose systems of the present invention appears to be at about 20 mcg/dl or 1 mcg/5 ml or 0.005 mcg/25 mcl meg/ml as indicated above and shown in FIG. 29.

EXAMPLE 11

The results of the comparison of a standard finger prick method with glucose patch subjects are depicted in FIGS. 30–33. The gels are a 1% Carbopol® gel. Prior to application of the glucose patch, the targeted skin area is wiped with propylene glycol.

The subject in FIG. 30 receives a glucose load approximately 10 minutes after the first glucose level test is performed. As expected, after the glucose load, this subject's glucose level rises, as indicated in FIG. 30 by both the standard finger prick method and the glucose patch.

The subject in FIG. 31 intakes a high sugar meal approximately 20 minutes after the first glucose level test is performed. As shown in FIG. 31, there is an elevation in this subject's glucose level after consumption of the high sugar meal.

In FIG. 32, the subject receives a meal at about 50 minutes after the first glucose level tests. Slight elevation in glucose level is observed in FIG. 32.

In FIG. 33, a subject receives a glucose load at about 20 minutes after the first glucose tests. In spite of glycol load, little elevation in glucose level is observed, probably due to the hard work in which the subject was engaged during the testing, as shown by both the glucose patch and the standard finger prick method in FIG. 33.

These results demonstrate good correlation between the glucose patch and the standard prick method over a glucose range of 50–200 mg/dl.

EXAMPLE 12

The results of the comparison of two standard finger stick methods, i.e., Blood LSP and Blood LSII, with glucose patch subjects are depicted in FIGS. 34–35. In all subjects, except the subjects depicted in FIGS. 37 and 44–45, no wipe is sued. The subjects in FIGS. 37 and 44–45 prewiped with a propylene wipe. The gels loaded into the glucose patches of this Example 12 are a 1% Carbopol® and 10% propylene glycol gel in deionized water (18 meg ohm). Th(e results show good correlation between the two standard finger stick methods, i.e., Blood LSP and Blood LSII, with the glucose patches over a glucose range of about 75 mg/dl to about 350 mg/dl.

EXAMPLE 13

Three distinct gels are tested in six subjects for permeation and diffusion enhancement. The three gels are 1% Carbopol® (CAR), 1% Carbopol® and 10% propylene glycol in deionized water (18 meg ohm) (CARPG) and 1%

Carbopol® and 10% sodium lauryl sulfate in deionized water (18 meg ohm). In testing the gels, they are loaded into glucose patches and placed in contact with skin for about 5 minutes for glucose diffusion to the membrane for chemical reaction and detection. The results are shown in FIG. 46 while all three gels are effective, FIG. 46 depicts that, in all but one subject, the 1% Carbopol and 10% propylene glycol gel is more effective.

Having described our invention, we claim:

1. A noninvasive transdermal system for detecting an analyte in extracted from or underneath the skin of a subject, said noninvasive transdermal system comprising:

a dry chemistry component for interacting with the analyte, said dry chemistry component having a sensitivity which enables it to detect the analyte extracted from or underneath the skin within about 6 minutes or less following application of said noninvasive transdermal system to the skin of the subject, and a wet chemistry component for wetting said dry chemistry component and for transferring the analyte from or underneath the skin to said dry chemistry component in an amount sufficient, so that said dry chemistry component can detect the analyte within about about 6 minutes or less following application of said noninvasive transdermal system to the skin of the subject, wherein said dry chemistry component and said wet chemistry component are stored separate from one another prior to application of said noninvasive transdermal system to the skin of the subject, and wherein said dry chemistry component is in communication with said wet chemistry component following application of said noninvasive transdermal system to the skin of the subject, so that said wet chemistry component can continuously wet said dry chemistry component while said noninvasive transdermal system is applied to the skin of the subject to enable the analyte to interact with the wetted dry chemistry component.

2. A noninvasive transdermal system of claim 1 where said wet chemistry component is a gel.

3. A noninvasive transdermal system of claim 2 wherein said gel comprises carboxy polymethylene and propylene glycol.

4. A noninvasive transdermal system of claim 2 wherein said gel consists essentially of about 1% carboxy polymethylene and about 10% propylene glycol.

5. A non-toxic and non-flammable, noninvasive transdermal system for detecting an analyte which has diffused from or underneath the skin of a subject, said noninvasive transdermal system comprising:

a single layered dry chemistry component for interacting with the analyte to detect the analyte, said dry chemistry component having a sensitivity which enables it to detect the analyte diffused from the biological fluid within about 15 minutes or less following application of said noninvasive transdermal system to the skin of the subject, and a single layered wet chemistry component for transferring the analyte from or underneath the skin to said dry chemistry component in an amount sufficient, so that said dry chemistry component can detect the analyte within about 15 minutes or less following application of said noninvasive transdermal system to the skin of the subject, wherein said single layered dry chemistry component and said single layered wet chemistry component are stored separate from one another prior to application of said noninvasive transdermal system to the skin of the subject, and wherein said single layered dry chemistry component is in communication with said single layered wet chemistry component following application of said noninvasive transdermal system to the skin of the subject, so that said single layered wet chemistry component can continuously wet said single layered dry chemistry component while said noninvasive transdermal system is applied to the skin of the subject.

6. A noninvasive transdermal system of claim 5 wherein the biological fluid is interstitial fluid.

7. A noninvasive transdermal system of claim 5 wherein the analytic is glucose.

8. A noninvasive transdermal system of claim 5 wherein said wet chemistry component is a gel which includes carboxy polymethylene and propylene glycol.

9. A noninvasive transdermal patch for detecting an analyte extracted from or underneath the skin of a subject, said noninvasive transdermal patch comprising:

a first housing having a dry chemistry component for interacting with the analyte, said dry chemistry component having a sensitivity for reliable detection and quantification of the analyte, when wetted, which enables it to detect the analyte extracted from or underneath the skin of a subject, said first housing having an outer top surface and an inner bottom, surface and an aperture therethrough in which said dry chemistry component is adapted to be positioned permit the analyte to interact with the dry chemistry component when wetted, so that the interaction between the analyte and said dry chemistry component, when wetted, can be visualized and the analyte can be detected;

a second housing having a wet chemistry component for wetting said dry chemistry component and for transferring the analyte from or underneath the skin to said dry chemistry component in an amount sufficient, so that said dry chemistry component, when wetted, can interact with the analyte to detect the analyte, said second housing having an inner top surface and an outer bottom surface and an aperture therethrough in which said wet chemistry component is adapted to be positioned;

said noninvasive transdermal patch having an unassembled form prior to application of wherein noninvasive transdermal patch to the skin of the subject, said first and second housings are stored separate from one another; and whereby, when said noninvasive transdermal patch is in an assembled form, said inner top surface of said second housing is positioned adjacent said inner bottom surface of said first housing and said outer bottom surface of said second housing of said noninvasive transdermal patch is positioned against the skin of the subject, so that said wet chemistry component is in continuous contact with both the skin and said dry chemistry component during use to enable said wet chemistry component to wet said dry chemistry component and to transfer the analyte in the biological fluid extracted from or underneath the skin of a subject to said wetted dry chemistry component to enable the analyte to interact with said wetted dry chemistry component, so that the analyte can be reliably and quantitatively detected within about 15 minutes or less following the positioning of said assembled noninvasive transdermal patch against the skin of the subject and while said noninvasive transdermal patch is positioned on the skin of the subject.

10. A noninvasive transdermal patch of claim 9, wherein said first and second housings are comprised of a moisture-impervious, cross-linked closed cell sponge.

11. A noninvasive transdermal patch of claim 10, wherein said moisture-impervious, cross-linked closed cell sponge is a polyethylene foam.

12. A noninvasive transdermal patch of claim 9, wherein said noninvasive transdermal patch, when in an unassembled form, further includes an outer top pulltab layer removably positioned on the inner bottom surface of said first housing and the inner top surface of said second housing.

13. A noninvasive transdermal patch of claim 12, wherein a pressure sensitive adhesive is affixed to one surface of said outer top pull tab, so that said outer top pull tab can be removably positioned adjacent the inner bottom surface of said first housing and the inner top surface of said second housing.

14. A noninvasive transdermal patch of claim 9, wherein said noninvasive transdermal patch further includes a moisture-impervious sheet positioned adjacent the outer top surface of said first housing and the outer bottom surface of said second housing, said moisture-impervious sheet including first and second through-holes, wherein the first through-hole is in alignment with the aperture in said first housing and the second through-hole is in alignment with the aperture in said second housing.

15. A noninvasive transdermal patch of claim 14, wherein said moisture-impervious sheet has top and bottom surfaces and a pressure sensitive adhesive affixed to both said top and bottom surfaces of said moisture-impervious sheet.

16. A noninvasive transdermal patch of claim 9, wherein said noninvasive transdermal patch, when in an unassembled form, further includes an outer bottom pulltab layer removably positioned on said moisture-impervious sheet.

17. A noninvasive transdermal patch of claim 9, wherein the skin of the subject is the right or left volar skin portion of the forearm of the subject.

18. A noninvasive transdermal patch of claim 9, wherein said dry chemistry component includes dry chemical reagents for reaction with the analyte to release or form a reporter or indicator molecule, which is indicative of the presence of the analyte in the biological fluid, so that the analyte can be reliably and quantitatively detected.

19. A noninvasive transdermal patch of claim 18, wherein said first housing includes a membrane conditioned with the dry chemical reagents.

20. A noninvasive transdermal patch of claim 19, wherein said membrane is comprised of a polyether sulfone.

21. A noninvasive transdermal patch of claim 18, wherein the dry chemical reagents include an enzyme and a chromophore.

22. A noninvasive transdermal patch of claim 18, wherein the dry chemical reagents include a chromophore, an enzyme, peroxidase, albumin, polyvinyl pyrrolidinone, dioctylsulfosuccinate and 2-butendioic acid.

23. A noninvasive transdermal patch of claim 21, wherein the chromophore is O-tolidine.

24. A noninvasive transdermal patch of claim 22, wherein the chromophore is O-tolidine.

25. A noninvasive transdermal patch of claim 21, wherein the chromophore is tetra-methyl benzidine.

26. A noninvasive transdermal patch of claim 22, wherein the chromophore is tetra-methyl benzidine.

27. A noninvasive transdermal patch of claim 21, wherein the enzyme is glucose oxidase.

28. A noninvasive transdermal patch of claim 22, wherein the enzyme is glucose oxidase.

29. A noninvasive transdermal patch of claim 21, wherein the enzyme is cholesterol oxidase and cholesterol esterase.

30. A noninvasive transdermal patch of claim 22, wherein the enzyme is cholesterol oxidase and cholesterol esterase.

31. A noninvasive transdermal patch of claim 9, wherein the analyte is glucose.

32. A noninvasive transdermal patch of claim 9, wherein the analyte is cholesterol.

33. A noninvasive transdermal patch of claim 9, wherein the analyte is selected from the group consisting of a triglyceride, bilirubin, creatinine, urea, alpha-amylase, lactate, lactic acid, alanine aminotransferase (ALT/GPT), aspartate aminotransferase (AST/GOT), albumin, uric acid, fructose amine, potassium, sodium, chloride, pyruvate dehydrogenase, phenylalaninehydroxylase, purine nucleotide enzymes and phenylalanine hydroxylase, phenylalanine, phenyl-pyruvate and phenyl-lactate.

34. A noninvasive transdermal patch of claim 9, wherein said detection occurs within about 3 to about 15 minutes or less.

35. A noninvasive transdermal patch of claim 9, wherein said detection occurs within about 4 to about 6 minutes or less.

36. A noninvasive transdermal patch of claim 9 wherein said wet chemistry component is a gel.

37. A noninvasive transdermal patch of claim 32 wherein said gel is a hydrophobic gel.

38. A noninvasive transdermal patch of claim 32 wherein said gel includes carboxy polymethylene.

39. A noninvasive transdermal patch of claim 32 wherein said gel includes a skin permeation enhancer.

40. A noninvasive transdermal patch of claim 35 wherein said skin permeation enhancer is propylene glycol.

41. A noninvasive transdermal patch of claim 32 wherein said gel comprises carboxy polymethylene and propylene glycol.

42. A noninvasive transdermal patch of claim 32 wherein said gel consists essentially of about 1% carboxy polymethylene and about 10% propylene glycol.

43. A noninvasive transdermal patch of claim 32 wherein said gel is present in said second housing in an amount of between about 20 mcls and 35 mcls.

44. A noninvasive transdermal patch of claim 32 wherein said gel is present in said second housing in an amount of about 25 mcls.

45. A noninvasive transdermal patch of claim 9, wherein said noninvasive transdermal patch has the ability to detect an analyte in a concentration which is at least as low as about 5 mcg/ml.

46. A noninvasive transdermal patch of claim 9, wherein the biological fluid is interstitial fluid.

47. A noninvasive transdermal system of claim 5, wherein said detection occurs within about 4 to about 6 minutes or less.

48. A noninvasive transdermal system of claim 5, wherein said wet chemistry component is a gel.

49. A noninvasive transdermal system of claim 44, wherein said gel is present in an amount of about 25 mcls.

50. A noninvasive transdermal system of claim 5, wherein said noninvasive transdermal system has the ability to detect the analyte in a concentration which is at least as low as about 5 mcg/ml.

51. A noninvasive transdermal system of claim 2, wherein said gel is present in an amount of about 25 mcls.

52. A noninvasive transdermal system of claim 1, wherein said noninvasive transdermal system has the ability to detect the analyte in a concentration which is at least as low as about 5 mcg/ml.

53. A noninvasive transdermal system of claim 1, wherein the biological fluid is interstitial fluid.

54. A noninvasive transdermal system of claim 1, wherein the analyte is glucose.

\* \* \* \* \*